United States Patent [19]

Corbett et al.

[11] 4,278,686

[45] Jul. 14, 1981

[54] CARBAPENUM DERIVATIVES, A PROCESS FOR THEIR PREPARATION AND THEIR USE IN PHARMACEUTICAL COMPOSITIONS AND INTERMEDIATES

[75] Inventors: David F. Corbett, Dorking; Alfred J. Eglington, Betchworth, both of England

[73] Assignee: Beecham Group Limited, England

[21] Appl. No.: 33,825

[22] Filed: Apr. 27, 1979

[30] Foreign Application Priority Data

May 6, 1978 [GB] United Kingdom ............... 18101/78
May 30, 1978 [GB] United Kingdom ............... 24358/78

[51] Int. Cl.$^3$ .................... C07D 487/04; A61K 31/40
[52] U.S. Cl. ............................. 424/274; 260/245.2 T; 424/114
[58] Field of Search .................... 260/326.31, 245.2 T; 424/274

[56] References Cited

U.S. PATENT DOCUMENTS

| | | | |
|---|---|---|---|
| 4,141,986 | 2/1979 | Cassidy et al. | 260/326.31 |
| 4,162,323 | 7/1979 | Kahan | 260/326.31 |
| 4,181,733 | 1/1980 | Christensen et al. | 424/274 |

OTHER PUBLICATIONS

Merck & Co.; Derwent Abstract 40383y/23, 2/6/77 & 40281y, 2/6/77.

*Primary Examiner*—Mary C. Lee
*Attorney, Agent, or Firm*—Jacobs & Jacobs

[57] ABSTRACT

The present invention provides antibiotic compounds of the formula:

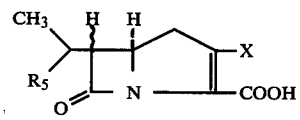

and salts and cleavable esters thereof wherein X is a $SCH_2CH_2NH_2$ or $YNH\text{-}COCH_3$ group where Y is a $SCH_2CH_2$, trans $-SO-CH=-$ or cis or trans $-S-CH=CH-$ group and R is a lower alkyl, aryl, aralkyl, lower alkenyl, or substituted lower alkyl.

90 Claims, No Drawings

CARBAPENUM DERIVATIVES, A PROCESS FOR THEIR PREPARATION AND THEIR USE IN PHARMACEUTICAL COMPOSITIONS AND INTERMEDIATES

British Patent Specifications Nos. 1467413, 1489235 and 1483142 disclose carbapenem antibiotics designated MM4550, MM13902 and MM17880. U.S. Pat. No. 3,950,375 discloses a further carbapenem antibiotic designated thienamycin. Belgium Patent Specification No. 864570 discloses substantially pure carbapenem antibiotics containing 6-hydroxyethyl substituents. A group of carbapenem antibiotics which were produced semi-synthetically have now been found.

The present invention provides the compounds of the formula (I):

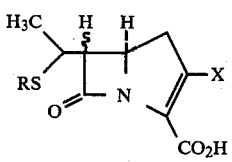

and salts and cleavable esters thereof wherein X is a $SCH_2CH_2NH_2$ or Y $NH.CO.CH_3$ group where Y is a $SCH_2CH_2$, trans $-SO-CH=CH-$ or cis or trans $-S-CH=CH-$ group and R is a lower alkyl, aryl, aralkyl, lower alkenyl or substituted lower alkyl group.

When used herein the term "lower" means that the group contains up to 4 carbon atoms. When used herein the term "aryl" means phenyl or phenyl substituted by nitro, fluoro, chloro, bromo, lower alkyl or lower alkyloxy. When used herein "aralkyl" means a lower alkyl group substituted by an aryl group. When used herein "substituted lower alkyl" means a lower alkyl group substituted by a lower alkoxy, acyloxy, lower esterified carboxyl, carboxyl, amino or acylamino group.

Suitable compounds of the formula (I) include those of the formulae (II)–(VI):

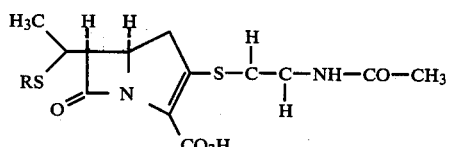

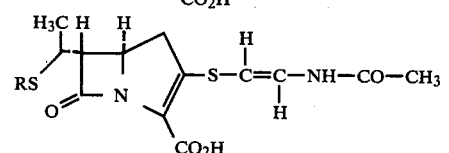

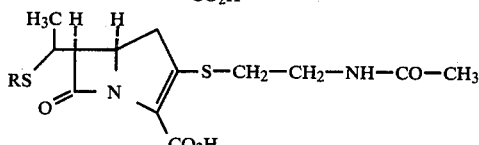

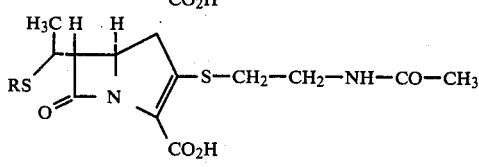

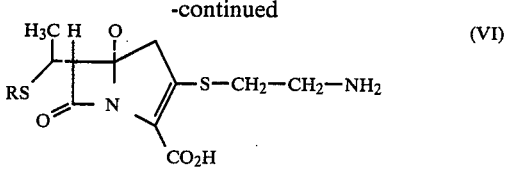

and salts and cleavable esters thereof wherein R is as defined in relation to formula (I).

Suitable groups R in the compounds (I)–(VI) include lower alkyl, aryl and aralkyl groups and lower alkyl groups substituted by a lower alkyl, lower esterified carboxyl or carboxyl group.

The compounds of the formula (I)–(VI) may have the 8S configuration. The compounds of the formulae (I)–(VI) may alternatively have the 8R configuration. If desired mixtures of 8R and 8S forms may be used.

Suitable values for R include the methyl, ethyl, n-propyl, n-butyl, benzyl, 2-phenylethyl, phenyl, p-methylphenyl, p-methoxyphenyl, p-chlorophenyl, methoxycarbonylmethyl, ethoxycarbonylmethyl and the like groups.

R may also be a 2-aminoethyl, 2-benzyloxycarbonylaminoethyl, 2-p-nitrobenzyloxycarbonylaminoethyl, 2-p-methoxybenzyloxycarbonylaminoethyl, allyl, p-nitrobenzyl, p-chlorobenzyl, p-bromobenzyl, p-methoxybenzyl, p-methylbenzyl, 2-acetamidoethyl, benzyloxycarbonylmethyl, p-nitrobenzyloxycarbonylmethyl, 2-methoxyethyl, 2-acetoxyethyl and the like groups.

Certain favoured values for R include the methyl, ethyl, benzyl and phenyl groups.

The compounds of the formulae (I)–(VI) may be presented in the form of the free acid. More suitably the compounds of the formula (I)–(VI) may be in the form of a salt such as an alkali metal salt, an alkaline earth metal salt or an ammonium or substituted ammonium salt. Suitable salts thus include the sodium, potassium, calcium, magnesium, ammonium, trimethylammonium and like salts. Preferred salts include the sodium and potassium salts. The lithium salt may also be prepared.

The compounds of the formulae (I)–(VI) may be presented in the form of an ester, for example an ester which is convertible by chemical or biological means to the corresponding compounds of the formulae (I)–(VI) or a salt thereof.

In relation to the preceding compounds the term ester includes those compounds wherein C2 ester moiety is of the sub-formulae (a)–(d):

$$-CO-O-A_1 \qquad \text{(a)}$$

$$-CO-O-CA_2A_3A_4 \qquad \text{(b)}$$

$$-CO-O-CHA_5-O.CO.A_6 \qquad \text{(c)}$$

$$\begin{array}{c}-CO-O-CH-A_7\\ \phantom{-CO-O-}|\phantom{A}\phantom{-}|\\ \phantom{-CO-O-}O\!-\!\!-\!\!CO\end{array} \qquad \text{(d)}$$

wherein $A_1$ is an alkyl group of up to 4 carbon atoms, an alkenyl group of up to 4 carbon atoms, an alkynyl group of up to 4 carbon atoms, or an alkyl group of up to 6 carbon atoms substituted by an alkoxyl group of up to 4 carbon atoms, a benzyloxyl group, a phenoxyl group, an acyl group of up to 4 carbon atoms, an alkoxycarbonyl group of up to 4 carbon atoms, a benzyloxycarbonyl group or by up to three halogen atoms; $A_2$ is a hydrogen atom, a methyl group, a phenyl group or a methoxyphenyl group; $A_3$ is a hydrogen atom, a methyl group, a phenyl group, a methoxyphenyl group or a nitrophenyl group; $A_4$ is a phenyl, halophenyl, nitrophenyl or methoxyphenyl group; $A_5$ is a hydrogen atom or methyl group; $A_6$ is an alkyl group of up to 6 carbon atoms, an alkoxyl group of up to 6 carbon atoms, a phenyl group, a phenoxy group, a benzyl group or a benzyloxy group; and $A_7$ is a $CH_2CH_2$ group, a $CH=CH$ group, an o-phenylene group or an o-phenylene group substituted by one or two methyl or methoxyl groups.

Favoured values for $A_1$ include the methyl, ethyl, propyl, butyl, allyl, ethynyl, methoxymethyl and benzyloxymethyl groups.

Favoured values for $CA_2A_3A_4$ include the benzyl, p-nitrobenzyl, 2-p-nitrophenylpropyl, benzhydryl and trityl groups.

Favoured values for $A_6$ include the methyl, t-butyl and ethoxy groups.

Favoured values for $A_7$ include the o-phenylene and dimethoxy-o-phenylene groups.

Certain preferred esters may be selected from the methyl ester, the methoxymethyl ester, the benzyl ester, the p-nitrobenzyl ester, the acetoxymethyl ester, the pivaloyloxymethyl ester, the phthalidyl ester and the α-ethoxycarbonyloxyethyl ester.

A particularly preferred ester is the phthalidyl ester.

A further particularly preferred ester is the p-nitrobenzyl ester.

Many of the preceding esters may be converted to the free acid or its salt by chemical methods such as hydrolysis or hydrogenolysis. For example esters of the sub-formulae (b)–(d) may be subjected to hydrogenation and esters of the sub-formula (a), (c) and (d) may be subjected to hydrolysis. Similarly esters, particularly those of the sub-formulae (c) and (d) are biologically hydrolysed, for example in-vivo.

In addition to those esters described above in relation to the preceding compounds the term ester includes these compounds wherein the C-2 ester moiety is of the sub-formula (e):

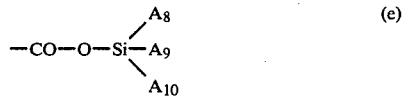

wherein $A_8$ is an alkyl group of up to 4 carbon atoms or a phenyl group, $A_9$ is an alkyl group of up to 4 carbon atoms or a phenyl group and $A_{10}$ is an alkyl group of up to 4 carbon atoms.

One particularly suitable value for the $SiA_8A_9A_{10}$ moiety is the trimethylsilyl group.

A further particularly suitable value for the $SiA_8A_9A_{10}$ moiety is the tertbutyldimethylsilyl group.

Another particularly suitable value for the $SiA_8A_9A_{10}$ moiety is the tertbutyldiphenylsilyl group.

In general the esters may be prepared by the reaction of a carboxylate salt with the appropriate silyl chloride.

The silyl esters are useful in that they can be readily removed, for example by mild hydrolysis or by reaction with anhydrous fluoride ion.

A further group of useful esters are those wherein the esterified carboxyl group is of the sub-formula (f):

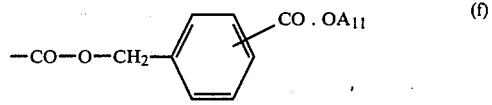

wherein $A_{11}$ is a lower alkyl group, preferably methyl.

Preferably, the alkoxycarbonyl group $CO_2A_{11}$ in the sub-formula (f) is at the 2- or 4-position in the benzene ring, more preferably at the 4-position.

Esters of the compounds of the formula (I) wherein the esterified carboxyl group is of the sub-formula (f) may be de-esterified by electrolysis as hereinafter described.

p-Nitrobenzyl esters may also be conveniently de-esterified by electrolysis.

This invention also provides a process for the preparation of a compound of the formula (I) as hereinbefore defined or a salt or cleavable ester thereof, which process comprises the addition of a thiolate of a thiol of the formula (VII):

$$R-SH \qquad (VII)$$

wherein R is as defined in relation to formula (I) to a compound of the formula (VIII) or (IX) or a mixture thereof:

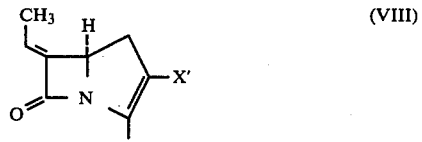

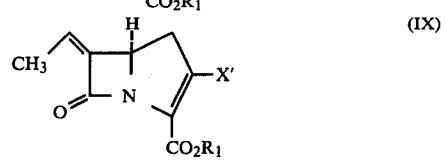

wherein X' is a group X as defined in relation to formula (I) in which any primary amino group is protected and $CO_2R_1$ is a cleavable ester group, and thereafter, if desired, converting the resulting ester to the free acid or a salt thereof.

The thiolate of the compound of the formula (VII) may be preformed or may be generated in situ, for example by the action of a base on the compound of the formula (VII). Such bases are most suitably anhydrous, and are generally alkali metal or alkaline earth metal bases such as carbonates or bicarbonates, for example, sodium or potassium carbonate.

The addition of the thiol is generally effected in an organic solvent at an ambient or depressed temperature. Suitable solvents include dimethylformamide, hexamethylphosphoramide and the like. The reaction is suitably carried out at a temperature of $-50°$ C. to $+20°$ C. and more suitably from $-40°$ to $0°$ C., for example at about $-20°$ to $10°$ C.

The product may be obtained from the reaction mixture by evaporation of the solvents. It is frequently convenient to remove water-soluble impurities prior to evaporation, for example by adding a water-immiscible solvent and then washing the mixed solvents with water. The initial crude product from the reaction may be purified by chromatographic techniques such as column chromatography on a mild support such as silica using gradient elution with solvent such as ethyl acetate and hexane or petroleum ether. The desired fractions may be identified using tlc and potassium permanganate spray.

In general the preceding reaction provides a preponderance of the compounds having the trans stereochemistry about the β-lactam ring.

The compounds produced by addition to a mixture of E- and Z-ethylidene compounds are in the form of a mixture of C8 isomers. It has been found that use of an isolated E- or isolated Z-ethylidene compound also leads to the mixture of C8 isomers. Such isomers may be separated chromatographically for example by column chromatography.

If the compound of the formula (I) per se or a salt thereof is required it may be prepared from a hydrogenolysable or hydrolysable ester by mild hydrogenation or mild hydrolysis. In general, it is preferred to hydrogenate a p-nitrobenzyl ester in order to produce the parent acid or its salt. Such hydrogenation is conveniently effected using an atmospheric pressure of hydrogen and a palladium on charcoal catalyst. Suitable solvents include aqueous dioxane and other similar solvents. If a salt is required, this may be generated in conventional manner by the addition of the desired amount of a base, for example an aqueous solution of a bicarbonate, carbonate or the like. The desired product may be obtained by evaporation of the solvents.

The salts of a compound of the formula (I) may be purified by chromatography, for example over a gel-filtration agent such as Biogel P2 (Biogel P2 is a registered trade mark which refers to a polyacrylamide gel supplied by Biorad). Suitable solvents for use include water or aqueous lower alkanols such as aqueous methanol aqueous ethanol or the like.

The addition of a thiolate of the compound of the formula (VII) to a compound of the formula (VIII) or (IX) produces predominantly a compound of the formula (I) having the trans configuration about the β-lactam ring.

Thus, this process is most suitably adapted to the preparation of a compound of the formula (III), (V) or (VI) or a salt thereof.

When it is desired to prepare a compound of the formula (I) or a salt or ester thereof wherein X is a SCH$_2$CH$_2$NH$_2$ group or there is a NH$_2$ substituent in the group R, the amino group will be protected in conventional manner during the reaction. Suitable protecting groups include benzyloxycarbonyl and p-nitrobenzyloxycarbonyl groups. The protecting group may be removed in conventional manner after the thiolate/ethylidene addition reaction has been carried out, for example, by hydrogenation in the presence of a transition metal catalyst, such as palladium on carbon.

The protected amino compounds may be prepared in conventional manner by the reaction of the amino compound with, for example, benzyl or p-nitrobenzyl chloroformate.

Further details of suitable protection/deprotection processes may be found in Danish Patent Application 4880/77.

This invention further provides a process for the preparation of a compound of the formula (I) or a salt thereof which process comprises the electrolysis of a corresponding ester, wherein the esterified carboxyl group is a group of the sub-formula (f) as hereinbefore defined or a p-nitrobenzyloxycarbonyl group.

Preferably, the electrolysis is carried out on a p-methoxycarbonylbenzyl ester.

The electrolysis will be effected using standard conditions, for example, in an inert aprotic solvent, using mercury, lead, platinum or carbon as the cathode and lead, platinum or carbon as the anode, and using a tetraalkylammonium halide or tetrafluoroborate as electrolyte.

We have found it particularly convenient to carry out the electrolysis in the cathodic compartment of a divided cell with a mercury pool electrode using DMF as solvent, 0.1 M tetrabutylammonium iodide or tetrafluoroborate as electrolyte, in the presence of acetic acid to quench any radical anions formed in the electrolysis, at a potential of about $-1.9$ v relative to the standard calomel electrode for cleavage of p-methoxycarbonylbenzyl esters, or about $-1.3$ v for p-nitrobenzyl esters.

The product of the electrolysis reaction may be recovered in conventional manner, for example by converting the compound to the sodium salt using an ion exchange resin (e.g. Amberlite IR 120, Na form) and further purifying the salt by, for example, gel chromatography on a material such as Biogel P-2. Alternatively, the product of the electrolysis may be adsorbed on a resin such as Amberlite IRA 458, then eluted with sodium chloride solution, the eluate being de-salted to provide a solution of the sodium salt of the compound of the formula (I). The salt of the compound of the formula (I) may be obtained in solid form by removing the solvent (for example, by freeze-drying or spray-drying) or by solvent precipitation.

This invention provides a further process for the preparation of the compounds of the formula (I) and salts and esters thereof, which process comprises the reaction of a compound of the formula (X):

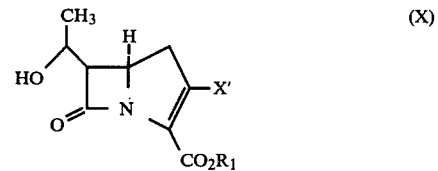

wherein R$_1$ and X' are as defined in relation to formulae (VIII) and (IX) with a compound of the formula (XI):

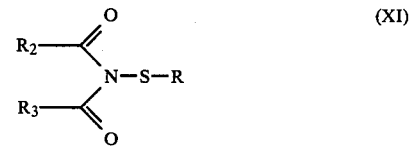

and a compound of the formula (XII):

in which R is as defined in relation to formula (I); R$_2$ and R$_3$ are moieties such that the compound of the formula (XI) is a sulfenimide; and R$_4$, R$_5$ and R$_6$ are groups such that the compound of the formula (XII) is a phosphine; and thereafter removing any amino protecting group; and thereafter if desired converting the thus-formed ester of the compound of the formula (I) to a corresponding free acid or salt.

The groups $R_2$ and $R_3$ will normally be selected from hydrocarbon groups which may be linked together. Particularly apt groups $R_2$ and $R_3$ include lower alkyl groups optionally linked to form part of a 5- or 6-membered ring.

Preferred compounds of the formula (XI) include those of the formulae (XIII) and (XIV):

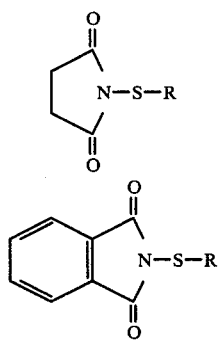

(XIII)

(XIV)

wherein R is as defined in relation to formula (I).

The compounds of the formula (XIII) are particularly suitable, as a by-product of the reaction is water soluble and may thus be readily removed by washing with water.

Suitable values for $R_4$, $R_5$ and $R_6$ include hydrocarbon groups of up to 7 carbon atoms and hydrocabon groups substituted by a group of the sub-formulae $OR^{11}$ or $O.CO.R^{11}$ where $R^{11}$ is a lower alkyl group.

Most suitably $R_4$, $R_5$ and $R_6$ each have the same meaning. Favoured values for $R_4$, $R_5$ and $R_6$ include methyl, ethyl, n-propyl, n-butyl, phenyl, 4-methoxyphenyl and benzyl.

A particularly suitable compound of the formula (XII) is tri-n-butyl phosphine.

The reaction of the compounds of the formulae (X), (XI) and (XII) may take place at any convenient non-extreme temperature, for example $-10°$ to $50°$ C., more usually $0°$ to $40°$ C., generally $10°$ to $30°$ C. and very conveniently at ambient (about $15°$–$25°$ C.). The reaction is generally carried out in an aprotic medium. Suitable solvents include hydrocarbon or ether solvents such as benzene, tetrahydrofuran, toluene and the like.

If desired the reaction may be carried out under an inert gas such as nitrogen.

Once the reaction is complete, for example as indicated by tlc, the mixture may be washed with water to remove the water-soluble products, and the organic layer dried and evaporated. The initial product may be further purified by chromatography if desired, for example over silica eluting with ethyl acetate/petroleum ether or the like.

Once formed the ester of the thioether may be converted to the corresponding acid or salt in conventional manner, for example as hereinbefore described.

The configuration at the 6-position in the product of this process will, of course, be determined by the configuration in the compound of the formula (X), little or no inversion of configuration at C-6 occurring during this process.

Inversion of configuration at C-1 in the 6-substituent ("C-8") often occurs in this process, so that the configuration at C-8 in the product is often opposite to the configuration at C-8 in the compound of the formula (X).

The present invention also provides a pharmaceutical composition which comprises a compound of the formula (I) as hereinbefore defined or a salt or in-vivo hydrolysable ester thereof and a pharmaceutically acceptable carrier.

If the compound of the invention present in such a composition is in the form of a salt then naturally it will be in the form of a pharmaceutically acceptable salt such as a pharmaceutically acceptable alkali metal salt, pharmaceutically acceptable alkaline earth metal salt or salt with a pharmaceutically acceptable nitrogenous base. Particularly suitable salts include the sodium salt and the potassium salt.

One group of preferred compounds for inclusion in the compositions of this invention include those of the formulae (II)–(VI) and salts and in-vivo hydrolysable esters thereof.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit dose composition adapted for administration by injection.

Unit-dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 kg adult is about 200 to 2000 mg, for example about 400, 600, 750, 1000 or 1500 mg.

The compositions of this invention may be used to treat infections of the respiratory tract, urinary tract or soft tissues in humans, mastitis in cattle or the like.

The carriers used in the compositions of this invention may include diluents, binders, disintegrants, lubricants, colours, flavoring agents, preservatives or the like in conventional manner. Thus suitable agents include lactose, starch, sucrose, calcium phosphate, sorbitol of the like, polyvinylpyrrolidone, acacia, gelatin, tragacanth or the like, potato starch or polyvinylpolypyrrolidone, magnesium stearate, sodium lauryl sulphate or the like.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin, mezlocillin or the like.

Particularly suitable penicillins for inclusion in orally administrable compositions of this invention include, ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride, bacampicillin hydrochloride and the like; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred pencillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred pencillin for inclusion in the injectably administrable compositions of this invention is sodium amoxycillin. A further preferred pencillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusions in the injectably administrable compositions of this invention include cephaloridine, cefazolin and cephradine, generally as their pharmaceutically acceptable salt such as the sodium salt.

The weight ratio between compound of this invention and pencillin or cephalosporin is generally from 10:1 to 1:10, for more usually from 5:1 to 1:5 and normally from 3:1 to 1:3.

The pencillin or cephalosporin is generally utilised in its conventionally administered amount.

This invention also provides processes for the preparation of a compound of the formula (VIII) or (IX) as hereinbefore defined, which processes comprise either:
(a) the elimination of the elements of a compound of the formula (XV):

$R_7$—$(O)_a$—$SO_3$—H  (XV)

wherein $R_7$ is a lower alkyl, aryl or lower aralkyl group and n is 0; or $R_7$ is a lower alkyl, aryl or lower aralkyl group or a cation and n is 1, from a compound of the formula (XVI):

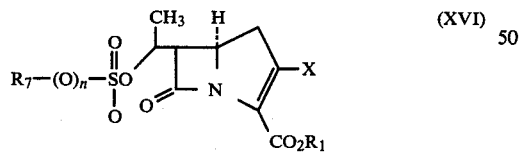

(XVI)

wherein X and $R_1$ are as defined in relation to formulae (VIII) and (IX) and $R_7$ and n are as defined in relation to formula (XV).

The elimination of the elements of a compound of the formula (XV) is most conveniently brought about by treatment of a compound of the formula (XVI) with a base in an aprotic medium. The base employed will be a base of low nucleophilicity so that in general primary and secondary amines will not be suitable. Suitable bases include powdered inorganic bases such as alkali metal carbonates, bicarbonates or hydroxides, for example powdered potassium carbonate, or hydrides or 1,5-diazabicyclo[5.4.0]undec-5-ene. Suitable solvents for use in this reaction include dimethylformamide, hexamethylphosphoramide, dichloromethane, tetrahydrofuran and the like.

The elimination may be effected at a non-extreme temperature such as −20°–70° C., for example 10° to 25° C. The reaction may be conveniently effected at ambient temperature.

Elimination of a compound of the formula (XV) from an ester of a trans compound of the formula (XVI) leads to the preparation of a Z- or EZ-isomer of the ethylidene compound whereas elimination from an ester of a cis-compound of the formula (XVI) leads to the preparation of the corresponding E- or EZ-isomer.

The desired product may be obtained from the reaction mixture by concentrating in vacuo, diluting with a water-immiscible organic solvent such as ethyl acetate, and removing impurities by washing with water. The organic layer may be re-evaporated in vacuo to yield the compound of the formula (VIII) or (IX) or a mixture thereof. These compounds may then be purified and/or separated chromatographically if desired, for example on silica gel using ethyl acetate, petroleum ether, chloroform, ethanol or the like or mixtures thereof as eluant.

Or (b) the elimination of the elements of water from a compound of the formula (XVII):

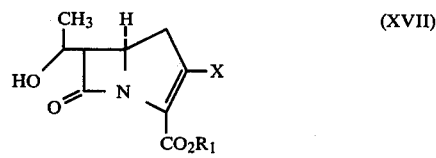

(XVII)

wherein X is as defined in relation to formula (I) and $CO_2R_1$ is a cleavable ester group, in the presence of a compound of the formula (XVIII):

$R_8O_2C$—N=N—$CO_2R_9$  (XVIII)

wherein $R_8$ and $R_9$ are independently lower alkyl, aryl or lower alkyl-aryl, and a compound of the formula (XIX):

(XIX)

wherein a, b and c are independently 0 or 1, and $R_{10}$, $R_{11}$ and $R_{12}$ are independently lower alkyl, aryl or lower alkyl-aryl.

In the compounds of the formula (XVIII) $R_8$ and $R_9$ are preferably selected from methyl, ethyl, propyl, butyl, phenyl and benzyl, the ethyl and t-butyl groups being preferred.

It is often convenient that $R_8$ and $R_9$ represent the same group.

Preferred compounds of the formula (XIX) include triarylphosphines and trialkylphosphites. Preferred groups $R_{10}$, $R_{11}$ and $R_{12}$ include methyl, ethyl, n-propyl, n-butyl, benzyl, phenyl and methoxyphenyl. Conveniently, $R_{10}$, $R_{11}$ and $R_{12}$ represent the same group. A particularly preferred compound of the formula (XIX) is triphenylphosphine.

Generally, approximately two equivalents of the compounds of the formulae (XVII), (XVIII) and (XIX) are used per mole of compound (XVII).

The elimination reaction is generally carried out at a non-extreme temperature, such as −20° to +100° C. We have found it convenient to begin the reaction at a depressed temperature, such as 0° C., and then to allow the temperature to rise to about room temperature.

The reaction is performed in an inert aprotic organic solvent. Suitable solvents include tetrahydrofuran, dioxane, ethyl acetate, benzene and the like.

Once the reaction is complete, the product may be obtained by washing with water, evaporation of the solvent and chromatography as hereinbefore described.

The compounds of the formula (XVI) wherein n is 0 may be prepared by the reaction of a compound of the formula (XVIII) with a compound of the formula (XX):

$$R_7-SO_2-Cl \qquad (XX)$$

or the chemical equivalent thereof wherein $R_7$ is as defined in relation to formula (XVI).

Suitable chemical equivalents of the compounds of the formula (XX) include the corresponding bromide, anhydride and the like.

In general, the reaction is performed in the presence of an acid acceptor to take up the acid generated by the reaction. Suitable acid acceptors include tertiary amines such as triethylamine and the like and powdered solid inorganic bases such as potassium carbonate or the like.

The reaction is normally carried out in a non-hydroxylic medium such as a halohydrocarbon such as dichloromethane or the like at a depressed temperature such as −20° to 10° C., for example −10° to 0° C.

When the reaction is over, the desired product may be obtained by washing the organic phase to remove water-soluble impurities and then evaporating the dried organic phase. The product may be further purified chromatographically if desired.

The di-esters within formula (XVI) wherein n is 1 may be prepared by the esterification of a salt of the formula (XXI):

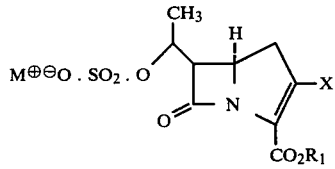

(XXI)

wherein X and $R_1$ are as defined in relation to formulae (VIII) and (IX) and $M^{\oplus}$ is a cation.

Conveniently, $M^{\oplus}$ is an alkali metal ion, such as a sodium ion, or a quaternary ammonium ion.

The esterification is generally carried out using a powerful esterifying agent such as a compound of the formula (XXII):

$$(R_7)_3O^{\oplus} BF_4^{\ominus} \qquad (XXII)$$

in a non-hydroxylic solvent, such as dichloromethane.

Compounds (I) where Y is a cis

$$-S-CH=CH-$$

group may be prepared by the isomerisation of a corresponding compound wherein Y is a trans —S—CH═ CH— group by contacting the compound with a mercuric salt in the presence of an inert solvent.

Suitable mercuric salts include the chloride, bromide, iodide, sulphate and acetate.

Suitable solvents include acetonitrile, acetone, dichloromethane, chloroform and water.

The reaction is generally carried out at a moderate temperature, such as −30° to +50° C., room temperature being convenient.

EXAMPLE 1 p-Nitrobenzyl (5R,6S)-3-[(E)-2-acetamidoethenylthio]-6-[(S)-1-methylsulphonyloxyethyl]-7-oxo-1-azabicyclo[3.2.0-]hept-2-ene-2-carboxylate

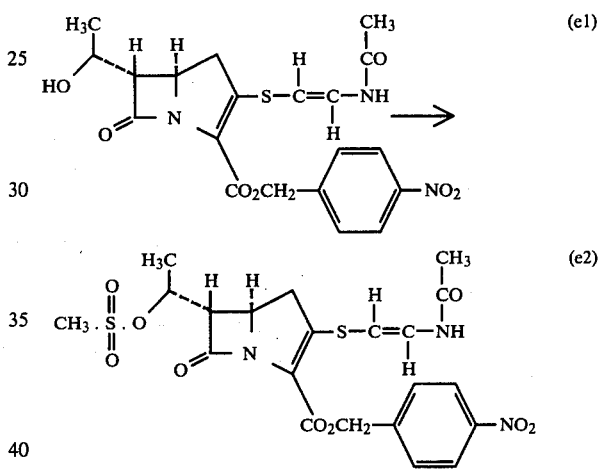

p-Nitrobenzyl (5R,6S)-3-[(E)-2-acetamidoethenylthio]-6-[(S)-1-hydroxyethyl]-7-oxo-1-azabicyclo[3.2.0-]hept-2-ene-2-carboxylate (e1) (147 mg) was suspended in dichloromethane (5 ml) containing triethylamine (100 mg), and the mixture was cooled to 0°. Whilst stirring the mixture at 0°, methanesulphonyl chloride (75 mg in 2.6 ml dichloromethane) was added dropwise over 5 minutes and the solution then stirred at a temperature of between 0° and −10° C. for a further 25 minutes. The solution was diluted with dichloromethane (10 ml) and washed with cold water (20 ml) phosphate buffer (pH 3.1) (20 ml) and 5% NaHCO$_3$ solution (20 ml). The organic layer was dried (MgSO$_4$) and evaporated down to afford a solid which was triturated with ether and collected by filtration to yield p-nitrobenzyl (5R,6S)-3-[(E)-2-acetamidoethenylthio]-6-[(S)-1-methylsulphonyloxyethyl]-7-oxo-1-azabicyclo[3.2.0]hept-2-ene-2-carboxylate (e2) (130 mg); $\nu_{max}$ (KBr) 1775, 1690, 1620, 1520, 1340, 1270 and 1175 cm$^{-1}$.

EXAMPLE 2 p-Nitrobenzyl (5R,6Z)-3-[(E)-2-acetamidoethenylthio]-6-ethylidene-7-oxo-1-azabicyclo[3.2.0]hept-2-ene-2-carboxylate

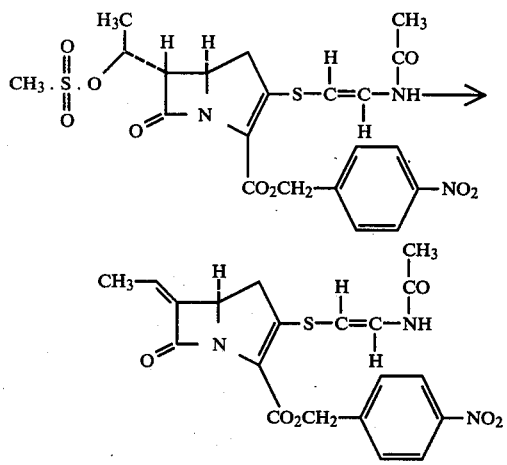

p-Nitrobenzyl (5R,6S)-3-[(E)-2-acetamidoethenylthio]-6-[(S)-1-methylsulphonyloxyethyl]-7-oxo-1-azabicyclo[3.2.0]hept-2-ene-2-carboxylate (e2) (100 mg) and powdered anhydrous potassium carbonate (62 mg) were stirred in dimethylformamide (2 ml) at room temperature for 30 minutes. The mixture was concentrated in vacuo, and the product was then partitioned between ethyl acetate (20 ml) and water (20 ml). The organic layer was washed with water (2×20 ml) and brine (20 ml), then dried (MgSO₄) and evaporated in vacuo. The residue was rapidly chromatographed on silica gel using ethyl acetate as eluant to afford p-nitrobenzyl (5R,6Z)-3-[(E)-2-acetamidoethenylthio]-6-ethylidene-7-oxo-1-azabicyclo[3.2.0]hept-2-ene-2-carboxylate (e3) (39 mg) as a foam; $\nu_{max}$ (CH$_2$Cl$_2$) 1770, 1705 and 1625 cm$^{-1}$; δ(CDCl$_3$) 2.05 (6H, br, s+d, CH$_3$CO and C$\underline{H}_3$CH), 3.04 (2H, m, centre of AA'X, 4-CH$_2$) 4.61 (1H, br t, J 8.5 Hz, 5-C$\underline{H}$), 5.18 and 5.46 (each 1H, d, J 14 Hz, C$\underline{H}_2$Ar), 5.82 (1H, d, J 13.5 Hz, =CH.S), 5.90 (1H, m, CH$_3$C$\underline{H}$), 7.15 (1H, dd, J 10.5 and 13.5 Hz, NHC$\underline{H}$=), 7.58 and 8.13 (each 2H, d, J, 9 Hz, ArCH$_2$), and about 8.05 (1H, br d, N$\underline{H}$).

EXAMPLE 3 p-Nitrobenzyl (5R,6R)-3-[(E)-2-acetamidoethenylthio]-6-[(S)-1-methylsulphonyloxyethyl]-7-oxo-1-azabicyclo[3.2.0]hept-2-ene-2-carboxylate

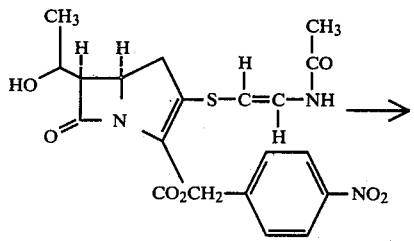

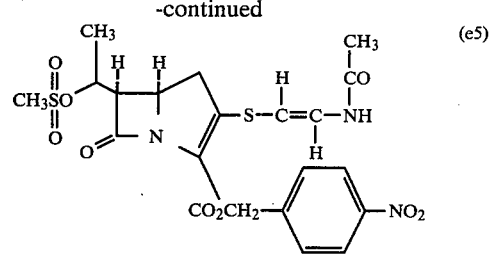

p-Nitrobenzyl (5R,6R)-3-[(E)-2-acetamidoethenylthio]-6-[(S)-1-hydroxyethyl]-7-oxo-1-azabicyclo[3.2.0]hept-2-ene-2-carboxylate (e4) (100 mg) was suspended in dichloromethane (6 ml) containing triethylamine (45 mg). The mixture was cooled to 0° and methanesulphonyl chloride (38.4 mg in 1.3 ml dichloromethane) was added dropwise over 5 minutes. After 25 minutes at 0° further quantities of triethylamine (15 mg) and methanesulphonyl chloride (13 mg) were added to the solution. After a further 10 minutes the solution was diluted with dichloromethane (10 ml) and was washed with cold water (20 ml), phosphate buffer (pH 3.1) (20 ml) and 5% NaHCO$_3$ solution (20 ml). The organic layer was dried (MgSO$_4$) and evaporated in vacuo to afford p-nitrobenzyl (5R,6R)-3-[(E)-2-acetamidoethenylthio]-6-[(S)-1-methylsulphonyloxyethyl]-7-oxo-1-azabicyclo[3.2.0]hept-2-ene-2-carboxylate (e5) as a yellow foam (107 mg); $\nu_{max}$ (CH$_2$Cl$_2$) 1780, 1700, 1625, 1525, 1350, 1330 and 1175 cm$^{-1}$.

EXAMPLE 4 p-Nitrobenzyl (5R,6E)-3-[(E)-2-acetamidoethenylthio]-6-ethylidene-7-oxo-1-azabicyclo[3.2.0]hept-2-ene-2-carboxylate

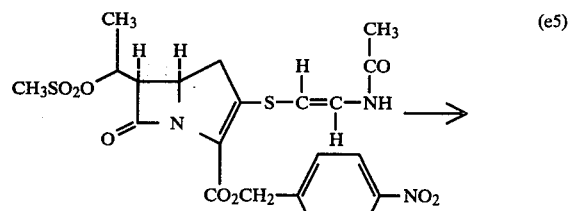

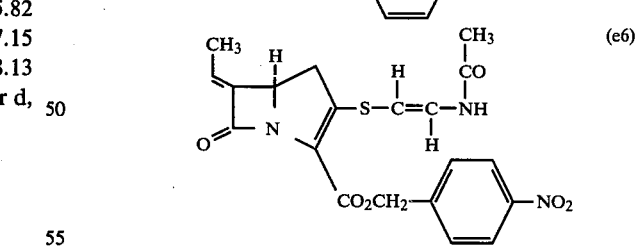

p-Nitrobenzyl (5R,6R)-3-[(E)-2-acetamidoethenylthio]-6-[(S)-1-methylsulphonyloxyethyl]-7-oxo-1-azabicyclo[3.2.0]hept-2-ene-2-carboxylate (e5) (100 mg) was treated with potassium carbonate in dimethylformamide as described in Example 2. The product (18 mg) was p-nitrobenzyl (5R,6E)-3-[(E)-2-acetamidoethenylthio]-6-ethylidene-7-oxo-1-azabicyclo[3.2.0]hept-2-ene-2-carboxylate (e6); $\nu_{max}$ (CH$_2$Cl$_2$) 1775, 1700 and 1625 cm$^{-1}$; δ(CDCl$_3$) 1.81 (3H, d, J 7 Hz, CH$_3$C$\underline{H}$), 2.05 (3H, s, C$\underline{H}_3$CO), 3.05 (2H, m, centre of ABX, 4-C$\underline{H}_2$), 4.70 (1H, br t, J 9 Hz, 5-C$\underline{H}$), 5.20 and 5.48 (each 1H, d, J 14 Hz, C$\underline{H}_2$Ar), 5.85 (1H, d, J 13.5 Hz, S.C$\underline{H}$=), 6.37 (1H, qd, J 7 and ca. 1 Hz, CH₃C$\underline{H}$), 7.15 (1H, dd, J 13.5 and 10 Hz, NH.C$\underline{H}$=), ca. 7.6 (1H, NH), 7.60 and 8.15 (each 2H, d, J 9 Hz ArCH₂).

EXAMPLE 5 p-Nitrobenzyl (5R,6S)-3-(2-acetamidoethylthio)-6-[(S)-1-methylsulphonyloxyethyl]-7-oxo-1-azabicyclo[3.2.0]hept-2-ene-2-carboxylate

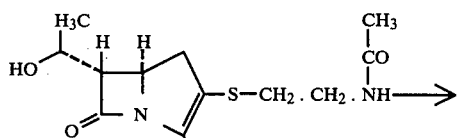

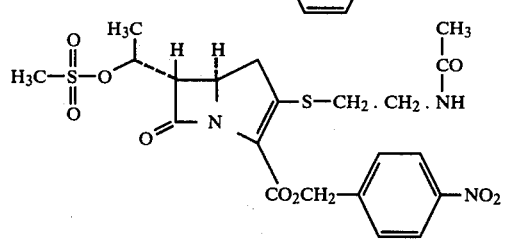

p-Nitrobenzyl (5R,6S)-3-(2-acetamidoethylthio)-6-[(S)-1-hydroxyethyl]-7-oxo-1-azabicyclo[3.2.0]hept-2-ene-2-carboxylate (e7) (100 mg) was treated with methanesulphonyl chloride and triethylamine in dichloromethane as described in Example 1. After work-up, evaporation of the dichloromethane solution afforded p-nitrobenzyl (5R,6S)-3-(2-acetamidoethylthio)-6-[(S)-1-methylsulphonyloxyethyl]-7-oxo-1-azabicyclo[3.2.0]hept-2-ene-2-carboxylate (e8) (112 mg) as a foam; ν$_{max}$ (CH₂Cl₂) 1785, 1700 sh, 1680, 1525, 1350, 1335 and 1175 cm⁻¹.

EXAMPLE 6 p-Nitrobenzyl (5R,6Z)-3-(-2-acetamidoethylthio)-6-ethylidene-7-oxo-1-azabicyclo[3.2.0]hept-2-ene-2-carboxylate

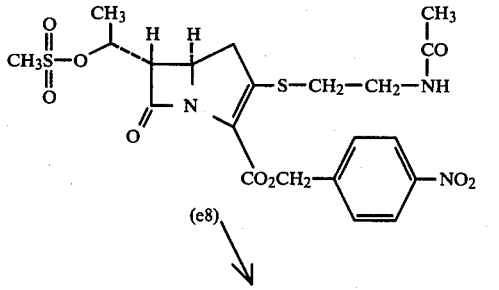

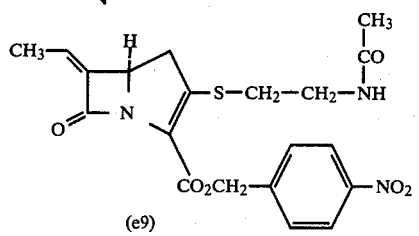

p-Nitrobenzyl (5R,6S)-3-(-2-acetamidoethylthio)-6-[(S)-1-methylsulphonyloxyethyl]-7-oxo-1-azabicyclo[3.2.0]hept-2-ene-2-carboxylate (e8) (110 mg) was treated with K₂CO₃ (100 mg) in dimethylformamide (3 ml) for 1 hour. Work-up and chromatography as described in Example 2 afforded p-nitrobenzyl (5R,6Z)-3-(-2-acetamidoethylthio)-6-ethylidene-7-oxo-1-azabicyclo[3.2.0]hept-2-ene-2-carboxylate (e9) as a gum (33 mg); ν$_{max}$ (CH₂Cl₂) 1770, 1700 and 1680 cm⁻¹; δ(CDCl₃) 1.92 (3H, s, CH₃CO), 2.04 (3H, d, J 7 Hz, CH₃CH), ca. 2.9–3.5 (6H, m, NC$\underline{H}_2$C$\underline{H}_2$S and 4-C$\underline{H}_2$), 4.67 (1H, br t, J 8.5 Hz, 5-C$\underline{H}$), 5.17 and 5.46 (each 1H, d, J 14 Hz, ArC$\underline{H}_2$), 5.92 (1H, q, J 7 Hz, CH₃C$\underline{H}$) ca. 6.05 (1H, br, N$\underline{H}$), 7.58 and 8.13 (each 2H, d, J 9 Hz, ArCH₂).

EXAMPLE 7 p-Nitrobenzyl (5R,6R)-3-(-2-acetamidoethylthio)-6-[(S)-1-methylsulphonyloxyethyl]-7-oxo-1-azabicyclo[3.2.0]hept-2-ene-2-carboxylate

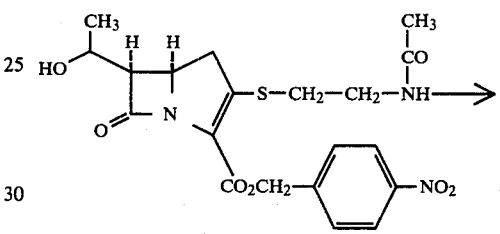

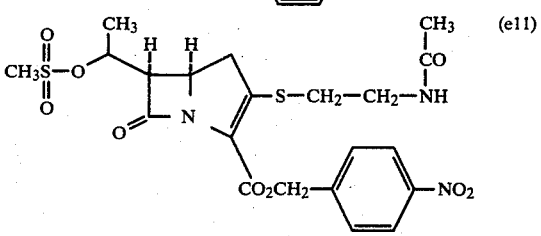

p-Nitrobenzyl (5R,6R)-3-(2-acetamidoethylthio)-6-(1-hydroxyethyl)-7-oxo-1-azabicyclo[3.2.0]hept-2-ene-2-carboxylate (e10) (80 mg) was treated with methanesulphonyl chloride and triethylamine in dichloromethane as described in Example 1. After work-up, evaporation of the dichloromethane solution afforded p-nitrobenzyl (5R,6R)-3-(2-acetamidoethylthio)-6-[(S)-1-methylsulphonyloxyethyl]-7-oxo-1-azabicyclo[3.2.0]hept-2-ene-2-carboxylate (e11) as a pale-yellow foam (67 mg); ν$_{max}$ (CH₂Cl₂) 1780, 1700, 1675, 1425, 1245 and 1175 cm⁻¹.

EXAMPLE 8 p-Nitrobenzyl (5R,6E)-3-(2-acetamidoethylthio)-6-ethylidene-7-oxo-1-azabicyclo[3.2.0]hept-2-ene-2-carboxylate

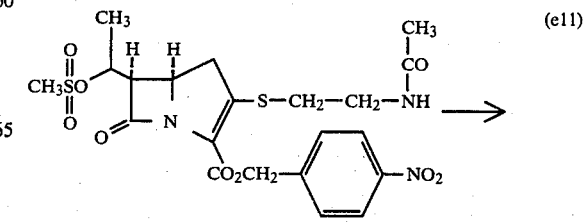

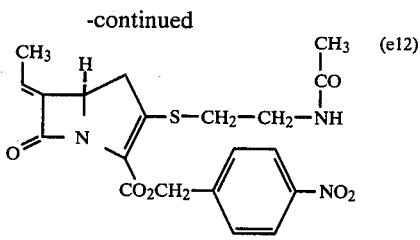

p-Nitrobenzyl (5R,6R)-3-(2-acetamidoethylthio)-6-[(S)-1-methylsulphonyloxyethyl]-7-oxo-1-azabicyclo[3.2.0]hept-2-ene-2-carboxylate (e11) (67 mg) was stirred with $K_2CO_3$ (70 mg) in dimethylformamide (2 ml) at room temperature for 1 hour. Work-up as in Example 2 gave a residue which was triturated with ethyl acetate/ether to afford a solid which was collected by filtration. The solid (10 mg) was identified as p-nitrobenzyl (5R,6E)-3-(2-acetamidoethylthio)-6-ethylidene-7-oxo-1-azabicyclo[3.2.0]hept-2-ene-2-carboxylate (e12); δ(DMF-d7) ca. 1.85 (3H, d, CH$_3$CH), 1.87 (3H, s, C$\underline{H}_3$CO) ca. 2.7–3.5 (6H, m, NCH$_2$CH$_2$S and 4-CH$_2$), 4.85 (1H, br t, J 9 Hz, 5-C$\underline{H}$), 5.29 and 5.53 (each 1H, d, J 14 Hz, C$\underline{H}_2$Ar), 6.38 (1H, br q, J 7 Hz, CH$_3$C$\underline{H}$), 7.76 and 8.20 (each 2H, d, J 9 Hz, ArCH$_2$), and ca. 8.0 (1H, NH).

EXAMPLE 9

Methyl (5R,6S)-3-[(E)-2-acetamidoethenylthio]-6-ethyl-7-oxo-1-azabicyclo[3.2.0]hept-2-ene-2-carboxylate and methyl (5R,6R)-3-[(E)-2-acetamidoethenylthio]-6-ethyl-7-oxo-1-azabicyclo[3.2.0]hept-2-ene-2-carboxylate

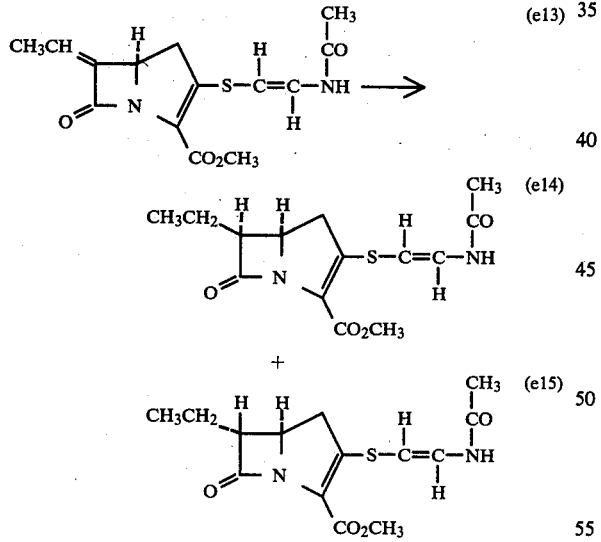

Methyl (5R,)-3-[(E)-2-acetamidoethenylthio]-6-ethylidene-7-oxo-1-azabicyclo[3.2.0]hept-2-ene-2-carboxylate (e13) (200 mg) was dissolved in tetrahydrofuran (20 ml), and the solution was hydrogenated at room temperature and atmospheric pressure for 15 hours in the presence of platinum oxide catalyst (200 mg). The mixture was filtered over Celite, and the filtrate was evaporated in vacuo. The residue was chromatographed on silica gel using ethyl acetate/cyclohexane mixtures to elute. The major product consisted of a mixture of methyl (5R,6S)-3-[(E)-2-acetamidoethenylthio]-6-ethyl-7-oxo-1-azabicyclo[3.2.0]hept-2-ene-2-carboxylate (e14) and the (5R,6R)-isomer (e15) (ca. 4:1); νmax (CHCl$_3$) 3300 br, 1775, 1700 and 1625 cm$^{-1}$; $\nu_{max}$ (EtOH) 322 and 225 nm; δ(CDCl$_3$) [(5R,6R)isomer]0.98 (3H, t, J 7.5 Hz, CH$_3$CH$_2$), ca. 1.75 (2H, m, CH$_3$C$\underline{H}_2$CH), 2.04 (3H, s, CH$_3$CO) 2.90 (2H, d, J 9 Hz, 4-CH$_2$), 3.46 (1H, m, 6-C$\underline{H}$) 3.78 (3H, s, CO$_2$CH$_3$), 4.20 (1H, dt, J 9 and 6 Hz, 5-CH), 5.87 (1H, d, J 14 Hz, S.C$\underline{H}$=CH), 7.18 (1H, dd, J 14 and 10 Hz, CH=C$\underline{H}$.NH), 8.25 (1H, broad d, J 10 Hz, NH). δ(CDCl$_3$) [(5R,6S)-isomer] as for (5R,6R)-isomer except 1.01 (3H, t, J 7.5 Hz, C$\underline{H}_3$CH$_2$), CA. 3.05 (3H, m, 4-C$\underline{H}_2$ and 6-C$\underline{H}$), 3.85 (1H, td, J 9 and 3 Hz, 5-C$\underline{H}$) and 5.85 (1H, d, J 14 Hz, SC$\underline{H}$=CH).

EXAMPLE 10

Benzyl (5R,6S)-3-[(E)-2-acetamidoethenylthio]-6-ethyl-7-oxo-1-azabicyclo[3.2.0]hept-2-ene-2-carboxylate and benzyl (5R,6R)-3-[(E)-2-acetamidoethenylthio]-6-ethyl-7-oxo-1-azabicyclo[3.2.0]hept-2-ene-2-carboxylate

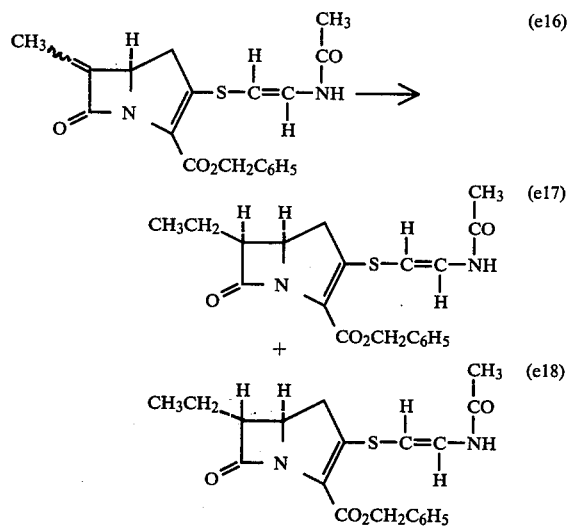

Benzyl (5R)-3-[(E)-2-acetamidoethenylthio]-6-ethylidene-7-oxo-1-azabicyclo[3.2.0]hept-2-ene-2-carboxylate (e16) (159 mg) was hydrogenated over platinum oxide catalyst (160 mg) in ethyl acetate (20 ml) for 18 hours. The mixture was filtered, and the filtrate was evaporated in vacuo to afford a gum which was chromatographed on silica gel using petroleum ether-ethyl acetate in a gradient elution. The first eluted product was benzyl (5R,6S)-3-[(E)-2-acetamidoethenylthio]-6-ethyl-7-oxo-1-azabicyclo[3.2.0]hept-2-ene-2-carboxylate (e17) as a colourless oil (41 mg); $\nu_{max}$ (CHCl$_3$) 3300 br, 1775, 1695 and 1625 cm$^{-1}$; $\lambda_{max}$ (EtOH) 322 and 226 nm, (CDCl$_3$) 0.94 (3H, t, J 7 Hz, C$\underline{H}_3$CH$_2$), 1.3–1.9 (2H, m, CH$_3$C$\underline{H}_2$CH), 1.98 (3H, s, CH$_3$CO), 2.85 (2H, d, J 9 Hz, 4-C$\underline{H}_2$), 3.40 (1H, m, 6-CH), 4.14 (1H, dt, J 6 and 9 Hz, 5-C$\underline{H}$), 5.20 (2H, centre of AA', wings at δ5.05 and 5.35, C$\underline{H}_2$Ph), 5.81 (1H, d, J 14, SC$\underline{H}$=), 7.03 (1H, dd, J 14 and 11 Hz, NHC$\underline{H}$=), 7.28 (5H, m, PhCH$_2$) and 8.03 (1H, broad d, J 11 Hz, NH).

Later fractions from the column were combined to afford a mixture of the (5R,6S)-isomer (e17) and the (5R,6R)-isomer (e18), (ca. 1:1) as an oil (48 mg). The p.m.r. spectrum of the mixture showed the following signals due to (e18) as well as those characteristic of (e17); δ(CDCl$_3$) inter alia 0.97 (3H, t, J 7 Hz, CH$_2$CH$_3$), ca. 3.0 (2H, m, 6-CH and 4-CH$_2$), 3.81 (1H, dt, J 2.5 and 9 Hz, 5-CH), and 5.78 (1H, d, J 14 Hz, S.C$\underline{H}$=).

EXAMPLE 11

Methyl (5R,6R)-3-[(E)-2-acetamidoethenylthio]-6-[(S)-1-methoxysulphonyloxyethyl]-7-oxo-1-azabicyclo[3.2.0-]hept-2-ene-2-carboxylate

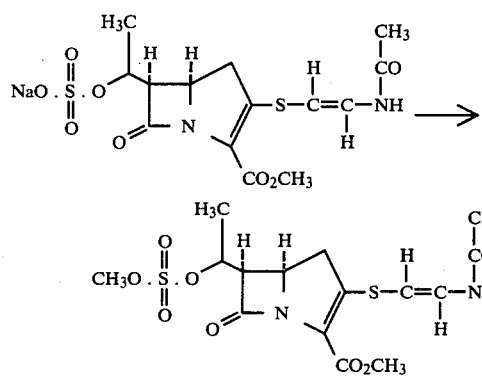

Sodium (5R,6R)-3-[(E)-2-acetamidoethenylthio]-6-[(S)-1-sulphonatooxyethyl]-7-oxo-2-methoxycarbonyl-1-azabicyclo[3.2.0]hept-2-ene (e19) (100 mg) in water (2 ml) was treated with cetylbenzyldimethylammonium chloride (93 mg) in dichloromethane (2 ml). After shaking and separating, the dichloromethane layer was dried (MgSO$_4$) and the dichloromethane removed by evaporation. Toluene was added to the residue and the toluene then evaporated to leave the dry benzyldimethyl-n-hexadecylammonium (5R,6R)-3-[(E)-2-acetamidoethenylthio]-6-[(S)-1-sulphonatooxyethyl]-7-oxo-2-methoxycarbonyl-1-azabicyclo[3.2.0]hept-2-ene (e21). This was then taken up in dry dichloromethane (2 ml) and treated with trimethyloxonium tetrafluoroborate (42 mg) and the mixture stirred. The trimethyloxonium tetrafluoroborate slowly dissolved, and after about 1 hour a solid was deposited from the reaction mixture. The dichloromethane was then removed by evaporation; ethyl acetate (10 ml) was added to the residue and the mixture triturated and filtered. The ethyl acetate was subsequently washed with water (5 ml), followed by brine (5 ml) and then dried (MgSO$_4$) and evaporated. The residue was chromatographed on silica gel, using ethyl acetate as eluting solvent to give methyl (5R,6R)-3-[(E)-2-acetamidoethenylthio]-6-[(S)-1-methoxysulphonyloxyethyl]-7-oxo-1-azabicyclo[3.2.0]hept-2-ene-2-carboxylate (e20) (10 mg). [$\nu_{max}$ (CHCl$_3$) 1785, 1705, 1625 cm$^{-1}$.]

In a further experiment the intermediate cetylbenzyldimethylammonium salt was dissolved in dry dichloromethane (2 ml) and treated with trimethyloxonium hexafluorophosphate (50 mg). After stirring for 1½ hours tlc indicated the formation of the dimethyl ester (e20).

EXAMPLE 12

Methyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate

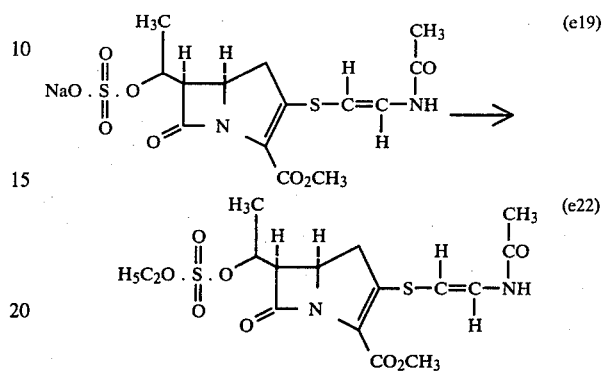

The benzyldimethyl-n-hexadecylammonium salt (e21) was prepared from the sodium salt (e19) as described in Example 11. This was taken up in dry dichloromethane (2 ml), cooled in an ice bath and triethyloxonium tetrafluoroborate under ether (55 mg) was added. The mixture was stirred in the cold for 30 minutes. The dichloromethane was then evaporated. Ethyl acetate (1 ml) was added to the residue and the resultant suspension was placed on a silica gel (230-400 mesh ASTM) column (6 g). The column was eluted with ethyl acetate. Early fractions yielded the required product, contaminated by a material which would not redissolve in ethyl acetate. The impurity was filtered off, and the resultant ethyl acetate solution was evaporated to yield methyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e22) (50 mg). $\nu_{max}$ (CHCl$_3$) 1785, 1700, 1625, 1260 and 1195 cm$^{-1}$; $\nu_{max}$ (CH$_2$Cl$_2$) 1790, 1705, 1625, 1200 cm$^{-1}$; δ(CDCl$_3$) 1.44 (3H, t, J 7 Hz, C$\underline{H}_3$CH$_2$), 1.64 (3H, d, J 6 Hz, 9-C$\underline{H}_3$CH), 2.08 (3H, s, C$\underline{H}_3$CO), 3.01 (1H, dd, J 18 and 9 Hz, 4-C$\underline{H}_A$H$_B$-CH), 3.23 (1H, dd, J 18 Hz and 9 Hz, 4-CH$_A$H$_B$-CH), 3.84 (3H, s, CO$_2$C$\underline{H}_3$), 3.73-3.91 (1H, m, 6-C$\underline{H}$), 4.35 (2H, q, J 7 Hz, OC$\underline{H}_2$CH$_3$), 4.28-4.47 (1H, m, 5-C$\underline{H}$), 5.03 (1H, dq, J 9 and 6 Hz, 8-C$\underline{H}$), 5.85 (1H, d, J 14 Hz, S.CH=CH), 7.30 (1H, dd, J 14 and 10 Hz, NH.C$\underline{H}$=CH), 8.18 (1H, d, J 10 Hz, CON$\underline{H}$CH=) p.p.m.

In an alternative experiment the sodium salt (e19) (110 mg) in suspension in dichloromethane (5 ml) was dreated with triethyloxonium tetrafluoroborate in dichloromethane (0.5 ml of a 100 mg/ml solution).

After 45 minutes a further 0.1 ml of the triethyloxonium tetrafluoroborate solution was added, and then after a further 10 minutes 0.1 ml of the solution was added. After another 1 minute the reaction mixture was diluted to 10 ml, washed with brine (5 ml), dried (MgSO$_4$) and evaporated to leave methyl (5R,6R)-3-[(E)-2-acetamidoethenylthio]-6-[(S)-1-ethoxysulphonyloxyehtyl]-7-oxo-1-azabicyclo[3.2.0]hept-2-ene-2-carboxylate (e22) (75 mg).

EXAMPLE 13

Benzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate

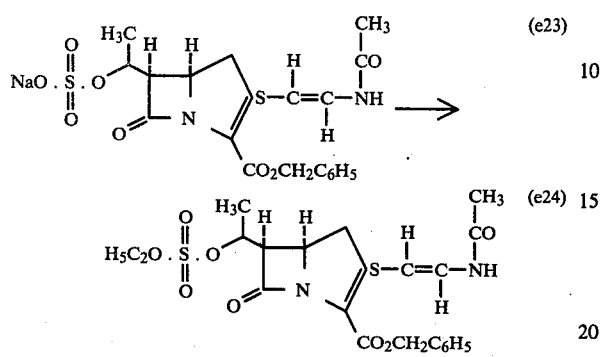

Sodium (5R,6R)-3-[(E)-2-acetamidoethenylthio]-6-[(S)-1-sulphonatooxyethyl]-7-oxo-2-benzyloxycarbonyl-1-azabicyclo[3.2.0]hept-2-ene (e23) (580 mg; containing some inorganic impurities) in water (10 ml) was treated with cetylbenzyldimethylammonium chloride (440 mg) in dichloromethane. After shaking and separating the dichloromethane layer was dried (MgSO$_4$) and evaporated to gvie cetylbenzyldimethylammonium (5R,6R)-3-[(E)-2-acetamidoethenylthio]-6-[(S)-1-sulphonatooxyethyl]-7-oxo-2-benzyloxycarbonyl-1-azabicyclo[3.2.0]hept-2-ene (e25). This was dissolved in dry dichloromethane (10 ml), cooled to 0° and triethyloxonium tetrafluoroborate under ether (250 mg) and dichloromethane (2 ml) added. The mixture was stirred at 0° for 30 minutes and then at room temperature for 1½ hours. The solvent was removed by evaporation and the residue chromatographed on silica gel (230–400 mesh ASTM) (6 g) using ethyl acetate as eluant. This failed to effect complete purification so the product was rechromatographed on silica gel (230–400 mesh ASTM) (30 g) eluting with dichloromethane (5 ml), followed by ethyl acetate/petroleum ether (b.p. 60°–80°) mixtures; 1:1 (100 ml), 3:1 (100 ml) and then with neat ethyl acetate. Combination and evaporation of relevant fractions yielded benzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e24) (153 mg). $\nu_{max}$ (CH$_2$Cl$_2$) 1785, 1705, 1620 and 1200 cm$^{-1}$. δ(CDCl$_3$), 1.38 (3H, t, J 7 Hz, CH$_3$CH$_2$), 1.63 (3H, d, J 6 Hz, 9-CH$_3$CH), 2.03 (3H, s, COCH$_3$), 2.95 (1H, dd, J 18 and 9 Hz, 4-CH$_A$H$_B$CH), 3.27 (1H, dd, J 18 and 9 Hz, 4CH$_A$H$_B$CH), 3.76 (1H, dd, J 10 and 6 Hz, 6-CH), ca. 4.1–4.4 (1H, m, S-CH), 4.28 (2H, q, J 7 Hz, OCH$_2$CH$_3$), 4.8–5.15 (1H, m, 8-CH), 5.23 (2H, s, OCH$_2$Ph), 5.78 (1H, d, J 14 Hz, SCH=CH), 7.08–7.50 (6H, m, NHCH=CH, 5 x Ar-H), 8.22 (1H, d, J 11 Hz, CONH).

In a further experiment the sodium salt (e21) (100 mg) in dry dichloromethane (5 ml) was treated with a solution of triethyloxonium tetrafluoroborate in dichloromethane (0.40 ml of a 100 mg/ml solution). After 20 minutes a further 0.1 ml aliquot of the triethyloxonium tetrafluoroborate solution was added and the mixture stirred for a further 15 minutes. The mixture was then washed with brine, dried (MgSO$_4$) and evaporated to give the mono benzyl monoethyl diester (e25) (90 mg).

EXAMPLE 14 p-Nitrobenzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate

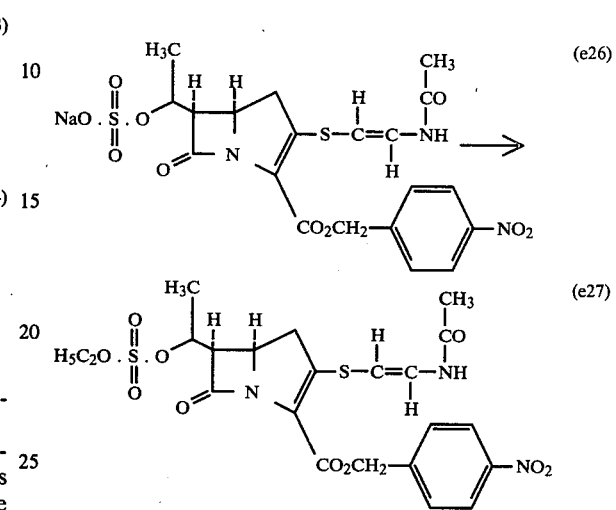

Sodium (5R,6R)-3-[(E)-2-acetamidoethenylthio]-6-[(S)-1-sulphonatoxyethyl]-7-oxo-2-p-nitrobenzyloxycarbonyl-1-azabicyclo[3.2.0]hept-2-ene (e26) (210 mg) and cetylbenzyldimethylammonium chloride (160 mg) were shaken together in dichloromethane (10 ml) and water (10 ml), the dichloromethane layer was separated, dried (MgSO$_4$) and evaporated to give cetylbenzyldimethylammonium (5R,6R)-3-[(E)-2-acetamidoethenyl-thio]-6-[(S)-1-sulphonatooxyethyl]-7-oxo-2-p-nitrobenzyloxycarbonyl-1-azabicyclo[3.2.0]hept-2-ene (e28). This was taken up in dry dichloromethane (2 ml) and treated with triethyloxonium tetrafluoroborate (0.7 ml of a 100 mg/ml solution in CH$_2$Cl$_2$). After 30 minutes a further 0.1 ml of the tetrafluoroborate solution was added and then after 5 minutes the resultant mixture was chromatographed on silica gel (230–400 mesh ASTM) (10 g) eluting with ethyl acetate/cyclohexane. This gave the required diester. Some of the fractions were evaporated and residual oil was crystallised from ethyl acetate/cyclohexane to give p-nitrobenzyl (5R,6R)-3-[(E)-2-acetamidoethenylthio]-6-[(S)-1-ethoxysulphonylethoxyl]-7-oxo-1-azabicyclo[3.2.0]hept-2-ene-2-carboxylate (e27) (61 mg), m.p. 125°–128° (dec). $[\alpha]_{20}^{D}$ −183.9° (C 1.0%, CHCl$_3$). (Found: C, 47.56, H, 4.54; N, 7.59. C$_{22}$H$_{25}$N$_3$O$_{10}$S$_2$ requires C, 47.56; H, 4.54; N, 7.56%), $\nu_{max}$ (CH$_2$Cl$_2$) 1780, 1700 and 1620 cm$^{-1}$; δ(CDCl$_3$) 1.38 (3H, t, J 7 Hz, CH$_3$CH$_2$), 1.62 (3H, d, J 6 Hz, CH$_3$CH), 2.04 (3H, s, CH$_3$CO), 2.99 (1H, dd, J 19 and 10 Hz, H$_A$ of ABX), 3.25 (1H, dd, J 19 and 9 Hz, H$_B$ of ABX), 3.78 (1H, d, J 10 and 5.5 Hz, CH.CH.CH), 4.28 (2H, q, J 7 Hz, CH$_3$CH$_2$) ca. 5.2 (1H, m, CHCH$_2$), 4.98 (1H, m, CH$_3$CHCH), 5.16 and 5.42 (each H, d, J 14 Hz, CH$_2$Ar), 5.78 (1H, d, J 13.5 Hz, CH=CHS), 7.20 (1H, dd, J 13.5 and 10 Hz, NHCH=C), 7.53 and 8.11 (each 2H, d, J 9 Hz, aromatic protons), and 8.26 (1H, d, J 101 NH), ppm.

EXAMPLE 15 p-Bromobenzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate

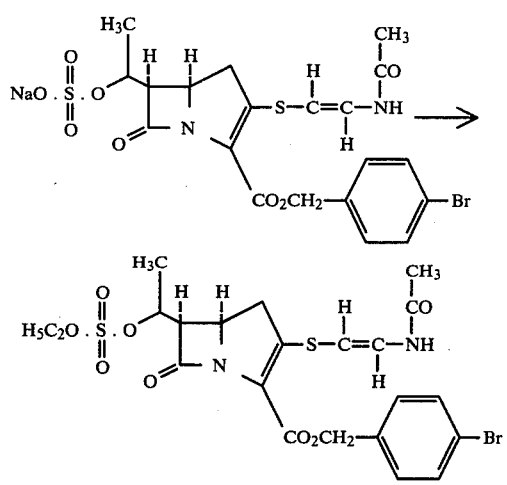

Sodium (5R,6R)-3-[(E)-2-acetamidoethenylthio]-6-[(S)-1-sulphonatooxyethyl]-7-oxo-2-p-bromobenzyloxycarbonyl-1-azabicyclo[3.2.0]hept-2-ene (e29) (200 mg), suspended in dichloromethane (10 ml), was stirred and a solution of triethyloxonium tetrafluoroborate in dichloromethane (0.65 ml of a 100 mg/ml solution) was added. The mixture was stirred for 35 minutes when a further 0.1 ml aliquot of the triethyloxonium tetrafluoroborate solution was added, and after stirring for a further 10 minutes the reaction mixture was placed on a silica gel (230-400 mesh ATSM) column (10 g) and eluted with ethyl acetate/cyclohexane (8:2). Evaporation yielded p-bromobenzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e30) (92 mg) which was crystallized from ethylacetate/cyclohexane to give crystals, m.p. 121°-124° (dec); Found: C,44.79; H,4.40, N,4.86. $C_{22}H_{25}BrN_2O_8S_2$ requires C, 44.82; H, 4.27; N, 4.76%), $[\alpha]_D^{20}$ −124.9 (CHCl$_3$ c. 1.0) $\nu_{max}$ (EtOH) 325 ($\epsilon_{max}$ 17340), 227 (24,300)nm, $\nu_{max}$ (CH$_2$Cl$_2$) 1785, 1705, 1625, 1195 cm$^{-1}$, δ (CDCl$_3$) 1.41 (3H, t, J 7 Hz, C$\underline{H}_3$CH$_2$), 1.63 (3H, d, J 6 Hz, C$\underline{H}_3$CH), 2.04 (3H, s, COC$\underline{H}_3$), 2.98 (1H, dd, J 18.5 and 10 Hz, $\underline{H}_A$ of ABX system), 3.24 (1H, dd, J 18.5 and 9 Hz, $\underline{H}_B$ of ABX system), 3.76 (1H, dd, J 10 and 5.5 Hz, CH.C$\underline{H}$CH), 4.1–4.4 (1H, m, CH.C$\underline{H}$.CH$_2$) 4.28 (2H, q, J 7 Hz, OC$\underline{H}_2$CH$_3$), 4.7–5.2 (1H, m, CH$_3$.C$\underline{H}$.CH), 5.07 and 5.24 (2H, AB$_q$, J 13 Hz), 5.76 (1H, d, J 13.5 Hz, SC$\underline{H}$=CH), 7.08–7.5 (1H, m, NHC$\underline{H}$=CH), 7.22 (2H, d, J 9 Hz, 2 x Ar-$\underline{H}$), 7.41 (2H, d, J 9 Hz, 2 x Ar-$\underline{H}$), 7.98 (1H, d, J 10 Hz, CON$\underline{H}$CH=) p.p.m.

EXAMPLE 16 p-Nitrobenzyl (5R,6R)-3-(2-acetamidoethylthio)-6-[(S)-1-ethoxysulphonyloxyethyl]-7-oxo-1-azabicyclo[3.2.0]hept-2-ene-2-carboxylate

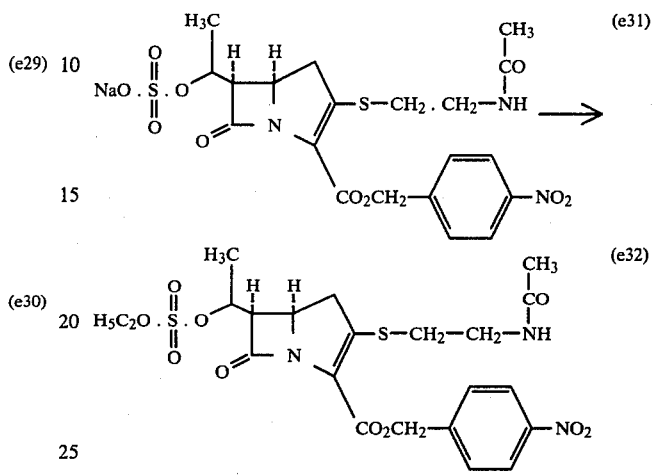

p-Nitrobenzyl (5R,6R)-3-(2-acetamidoethylthio)-6-[(S)-1-ethoxysulphonyloxyethyl]-7-oxo-1-azabicyclo[3.2.0]hept-2-ene-2-carboxylate (e32) was prepared (31% yield) by a process analogous to that described in Example 14. The diester (e32) was crystallised from hot ethanol to afford small needles m.p. 126°–128° (Found: C, 47.5; H, 5.0; N, 7.5%. $C_{22}H_{27}N_3O_{10}S_2$ requires C, 47.4; H, 4.9; N, 7.5%); $\lambda_{max}$ (EtOH) 318 ($\epsilon_{max}$ 13,600) and 270 (11,900) nm; $\nu_{max}$ (KBr) 1765, 1690 and 1645 cm$^{-1}$.

EXAMPLE 17

Benzyl (5R,6R)-3-[(E)-2-acetamidoethenylthio]-6-[(R)-1-ethylthioethyl]-7-oxo-1-azabicyclo[3.2.0]hept-2-ene-carboxylate and benzyl (5R,6-R)-3-[(E)-2-acetamidoethenylthio]-6-[(S)-1-ethylthioethyl]-7-oxo-1-azabicyclo[3.2.0]hept-2-ene-carboxylate

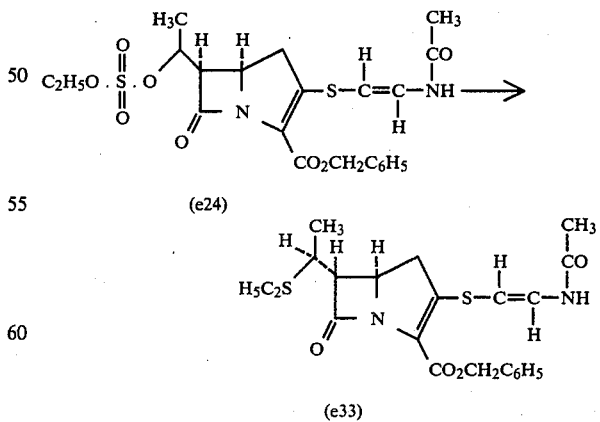

Benzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e24) (235 mg) in dimethylformamide (4 ml) was treated with finely powdered potassium carbonate (32 mg) and cooled to −60°. Ethane thiol in dimethylformamide (1.43 ml of a 20 mg/ml solution) was added to the mixture and stirring was continued as the reaction mixture was allowed to reach room temperature. After 4 hours at room temperature the solution was added to ethyl acetate (50 ml) and washed with a mixture of water (15 ml) and brine (30 ml) (3 x). The organic layer was dried (MgSO₄) and evaporated to leave a gum which was chromatographed on silica gel (230–400 mesh ASTM) (20 g), eluting with ethyl acetate/cyclohexane mixtures thus: 3:7 (100 ml); 4:6 (50 ml), 1:1 (200 ml), 3:1 (200 ml) and finally ethyl acetate. Eventually one isomer of the title compound (e33) (17 mg) was eluted followed by a mixture of 2 isomers of the title compound (e33) (25 mg) and then the second isomer of the title compound (e33) (21 mg).

EXAMPLE 18

Methyl (5R,6E)-3-[(E)-2-acetamidoethenylthio]-6-ethylidene-7-oxo-1-azabicyclo[3.2.0]hept-2-ene-2-carboxylate

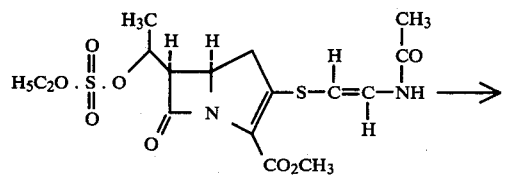

(e22)

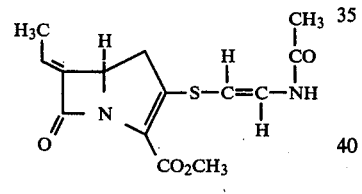

(e34)

Methyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e22) (42 mg) was taken up in ethanol (2 ml) and treated with anhydrous potassium acetate (50 mg). After 90 minutes the solvent was removed by evaporation and the product dissolved in ethyl acetate (10 ml) and washed with water (10 ml), and with brine (10 ml) and then dried (MgSO₄) and evaporated. The i.r. and u.v. spectra of crude material showed that the ethylidene compound had been formed. This was purified by chromatography on silica gel to give methyl (5R,6E)-3-[(E)-2-acetamidoethenylthio]-6-ethylidene-7-oxo-1-azabicyclo[3.2.0]hept-2-ene-2-carboxylate (e34) (14 mg). ν$_{max}$ (CH₂Cl₂) 1780, 1705, 1625 cm⁻¹. δ[CDCl₃+1 drop (CD₃)₂CO] 1.79 (3H, d, J 7 Hz, C$\underline{H}$₃CH=), 2.02 (3H, s, C$\underline{H}$₃CO), 2.90 (1H, dd, J 18 Hz and 8.5 Hz, $\underline{H}_A$ of ABX), 3.16 (1H, dd, J 18 and 9.5 Hz, $\underline{H}_B$ of ABX), 3.78 (3H, s, OC$\underline{H}$₃), 4.69 (1H, broad t, C$\underline{H}$.CH₂), 5.84 (1H, d, J 14 Hz SC$\underline{H}$:CH), 6.33 (1H, broad q, J 7 Hz, CH₃C$\underline{H}$=), 7.18 (1H, dd, J 14 and 10 Hz, NH.C$\underline{H}$=CH), 8.86 (1H, broad d, J 10 Hz, CON$\underline{H}$.CH) p.p.m.

EXAMPLE 19

Methyl (5R,6E)-3-[(E)-2-acetmidoethenylthio]-6-ethylidene-7-oxo-1-azabicyclo[3.2.0]hept-2-ene-2-carboxylate and methyl (5R,6Z)-3-[(E)-2-acetamidoethenylthio]-6-ethylidene-7-oxo-1-azabicyclo[3.2.0]hept-2-ene-2-carboxylate

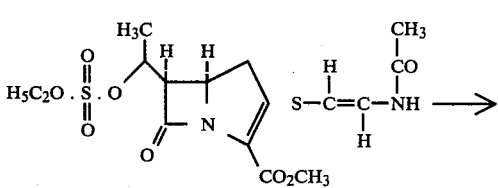

(e22)

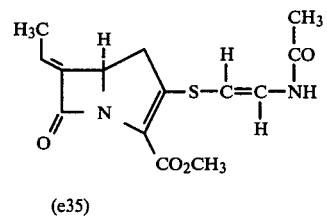

(e35)

+

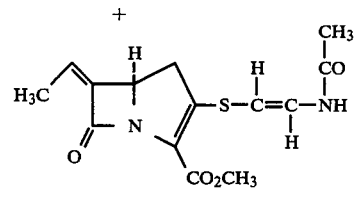

(e36)

Methyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e22) (86 mg) was taken up in dichloromethane (3 ml) and treated with 1,5-diazabicyclo[5.4.0]undec-5-ene (DBU) (33 mg) in dichloromethane (3.3 ml) added dropwise. After 15 minutes more DBU (3 mg) in dichloromethane (0.3 ml) was added and stirring was continued for 10 minutes. The solution was then washed with water (5 ml) and then chromatographed on silica gel to give methyl (5R,6E)-3-[(E)-2-acetamidoethenylthio]-6-ethylidene-7-oxo-1-azabicyclo[3.2.0]hept-2-ene-2-carboxylate and methyl (5R,6Z)-3-[(E)-2-acetamidoethenylthio]-6-ethylidene-7-oxo-1-azabicyclo[3.2.0]hept-2-ene-2-carboxylate as a mixture of isomers (e35 and e36) (21 mg), ν$_{max}$ (CH₂Cl₂) 1775 (broad), 1705, 1620 cm⁻¹.

EXAMPLE 20

Benzyl (5R,6E)-3-[(E)-2-acetamidoethenylthio]-6-ethylidene-7-oxo-1-azabicyclo[3.2.0]hept-2-ene-2-carboxylate and benzyl (5R,6Z)-3-[(E)-2-acetamidoethenylthio]-6-ethylidene-7-oxo-1-azabicyclo[3.2.0]hept-2-ene-2-carboxylate

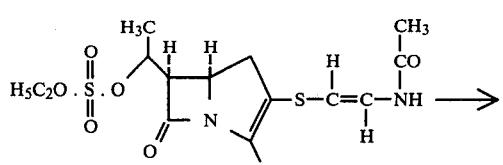

(e24)

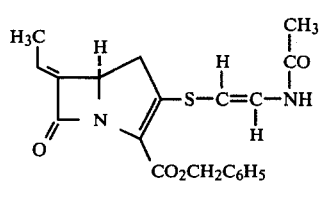

(e45)

+

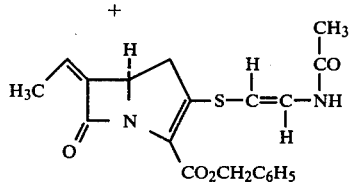

(e37)

Benzyl (5R,6R)-3-[(E)-2-acetamidoethenylthio]-6-[(S)-1-ethoxysulphonyloxyethyl]-7-oxo-1-azabicyclo[3.2.0]hept-2-ene-2-carboxylate (e24) prepared from sodium (5R,6R)-3-[(E)-2-acetamidoethenylthio]-6-[(S)-1-sulphonatooxyethyl]-7-oxo-2-benzyloxycarbonyl-1-azabicyclo[3.2.0]hept-2-ene (e23) (100 mg) as described in Example 13 was treated with 1,5-diazabicyclo[5.4.0]-undec-5-ene (35 mg) in an analogous manner to that described in Example 19 to give benzyl (5R,6E)-3-[(E)-2-acetamidoethenylthio]-6-ethylidene-7-oxo-1-azabicyclo[3.2.0]hept-2-ene-2-carboxylate and benzyl (5R,6Z)-3-[(E)-2-acetamidoethenylthio]-6-ethylidene-7-oxo-1-azabicyclo[3.2.0]hept-2-ene-2-carboxylate (e45 and e37) (30 mg). The n.m.r. spectrum [CDCl₃+(CD₃)₂SO]indicated that the ethylidene group was largely in the E-form (e45) but that some Z-form (e37) was also present.

EXAMPLE 21

Benzyl (5R,6E)-3-[(E)-2-acetamidoethenylthio]-6-ethylidene-7-oxo-1-azabicyclo[3.2.0]hept-2-ene-2-carboxylate and benzyl (5R,6Z)-3-(E)-2-acetamidoethenylthio-6-ethylidene-7-oxo-1-azabicyclo[3.2.0]hept-2-ene-2-carboxylate

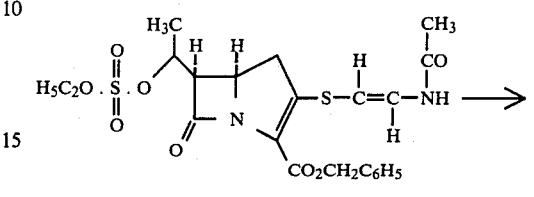

(e24)

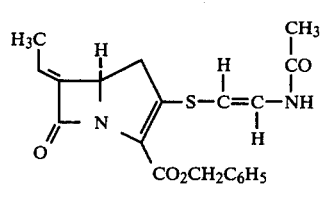

(e45)

+

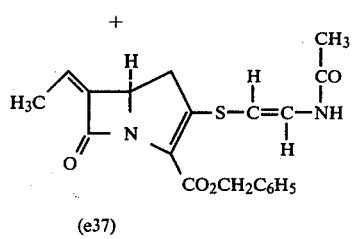

(e37)

Benzyl (5R,6R)-3-[(E)-2-acetamidoethylenylthio]-6-[(S)-1-ethoxysulphonyloxyethyl]-7-oxo-1azabicyclo[3.2.0]hept-2ene-2-carboxylate (18 mg) in dichloromethane (0.75 ml) was treated with a total of 0.16 ml of a 100 mg/ml solution of triethylamine in dichloromethane, added in equal aliquots over 90 minutes. The mixture was stirred for a further 90 minutes, washed with water (5 ml) and dried (MgSO₄). The solvent was then removed by evaporation to give benzyl (5R,6E)-3-[(E)-2-acetamidoethenylthio]-6-ethylidene-7-oxo-1-azabicyclo[3.2.0]hept-2-ene-2-carboxylate and benzyl (5R,6Z)-3-[(E)-2-acetamidoethenylthio]-6-ethylidene-7-oxo-1-azabicyclo[3.2.0]hept-2-ene-2-carboxylate (e45 and e37) (12 mg) as a 1:2 mixture.

EXAMPLE 22 p-Nitrobenzyl (5R,6E)-3-[(E)-2-acetamidoethenylthio]-6-ethylidene-7-oxo-1-azabicyclo[3.2.0]hept-2-ene-2-carboxylate

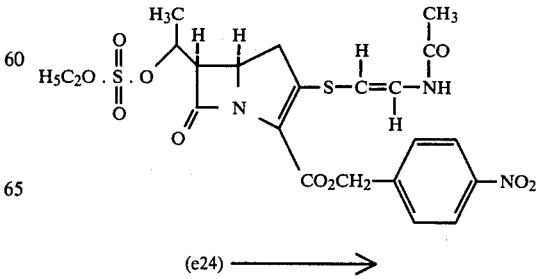

(e24) ⟶

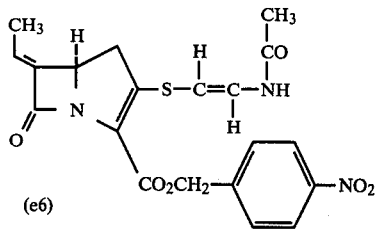
(e6)

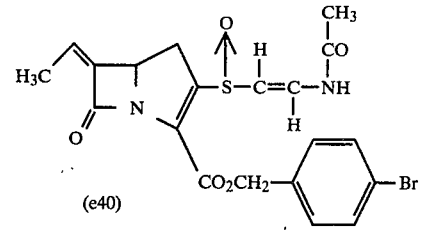
(e40)

p-Nitrobenzyl (5R,6R)-3-[(E)2-acetamidoethenylthio]-6-[(S)-1-ethoxysulphonyloxyethyl]-7-oxo-1-azabicyclo[3.2.0]hept-2-ene-2-carboxylate (e32) (109 mg) in dimethylformamide (2 ml) was treated with potassium carbonate (100 mg) for 90 minutes.

The solvent was removed by evaporation, the residue dissolved in ethyl acetate (10 ml) and washed with water (10 ml). The organic layer was dried (MgSO$_4$) and the solvent removed by evaporation. The residue was chromatographed on silica gel (230–400 mesh ASTM) to give p-nitrobenzyl (5R,6E)-3-[(E)-2-acetamidoethenylthio]-6-ethylidene-7-oxo-1-azabicyclo[3.2.0]hept-2-ene-2-carboxylate (e6) (60 mg). $\nu_{max}$ (CHCl$_3$) 1770 (br), 1700, 1625 cm$^{-1}$. $\delta$(DMF-d$_7$), 1.82 (3H, d, J 7 Hz, C$\underline{H}_3$CH), 1.98 (3H, s, C$\underline{H}_3$CO), 3.0–3.5 (2H, ABX, C$\underline{H}_2$CH), 4.83 (1H, broad t, J 9 Hz, CH$_2$C$\underline{H}$), 5.30 and 5.54 (each 1H, d, J 14 Hz, C$\underline{H}_2$Ar), 5.96 (1H, d, J 13.5 Hz, CH=C$\underline{H}$S), 6.38 (1H, dq, J 1 and 7 Hz, CH$_3$C$\underline{H}$=), 7.16 (1H, dd, J 13.5 and 10 Hz, C$\underline{H}$=CHNH), 7.77 and 8.21 (each 2H, d, J 9 Hz, aromatic protons).

The above conversion of (e27) into (e6) was also carried out by a method analogous to that of Example 18 with a yield of 67%.

EXAMPLE 23 p-Bromobenzyl (5R,6E)-3-[(E)-2-acetamidoethenylsulphinyl]-6-ethylidene-7-oxo-1-azabicyclo[3.2.0]hept-2-ene-2-carboxylate and p-bromobenzyl (5R,6Z)-3-(E)-2-acetamidoethenylsulphinyl-6-ethylidene-7-oxo-1-azabicyclo[3.2.0]hept-2-ene-2-carboxylate

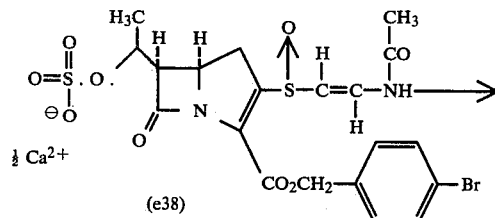
(e38)

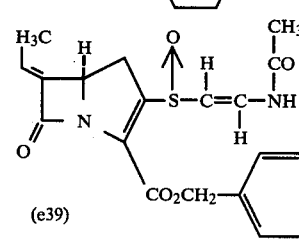
(e39)

+

Calcium (5R,6R)-3-[(E)-2-acetamidoethenylsulphinyl]-6-[(S)-1-sulphonatoxyethyl]-7-oxo-2-p-bromobenzyloxycarbonyl1-azabicyclo[3.2.0]hept-2-ene (e-38) (180 mg) was heated under reflux in dioxan (20 ml) containing AMBERLITE IRC 50 (Na) (the sodium form of a carboxylate ion exchange resin) (3.0 g) for 1¾ hours. The solution was then cooled and filtered and the solvent evaporated to leave a gum (80 mg). This was chromatographed on silica gel (10 g), eluting with chloroform/ethanol mixtures to yield a mixture of p-bromobenzyl (5R,6E)-3-[(E)-2-acetamidoethenylsulphinyl-6-ethylidene-7-oxo-1-azabicyclo[3.2.0]hept-2-ene2-carboxylate and p-bromobenzyl (5R,6Z)-3-[(E)-2-acetamidoethenylsulphinyl-6-ethylidene-7-oxo-1-azabicyclo[3.2.0]hept-2-ene-2-carboxylate (e39 and e40) (5 mg); $\nu_{max}$ (CDCl$_3$)1785, 1710, 1630 cm$^{-1}$. ppm (CDCl$_3$) 1.85 (3H, d, J 8 Hz), 2.08 (3H, s,), 2.9–3.8[2H, m(AB of an ABX system)], 4.8 (1H, broad t, J ca. 9 Hz), 5.22 (2H, s), 6.2 (1H, d, J 15 Hz), 6.48 (1H, broadened q, J ca 8 Hz, 7.1–7.6 (5H, m), 8.35 (1H, d, J 9 Hz).

A mass spectrum of the product showed an ion at m/e 363.01034 corresponding to C$_{16}$H$_{14}$BrNO$_4$ (requires m/e 363.01066), i.e. (M$^+$-SCH:CHNHCOCH$_3$+H).

The n.m.r. spectrum quoted is that of the (E)-isomer which is the major product of the reaction.

EXAMPLE 24

Methyl (5R,6E)-3-[(E)-2-acetamidoethenylthio]-6-ethylidene-7-oxo-1-azabicyclo[3.2.0]hept-2-ene-2-carboxylate and methyl (5R,6Z)-3-[(E)-2-acetamidoethenylthio]-6-ethylidene-7-oxo-1-azabicyclo[3.2.0]hept-2-ene-2-carboxylate

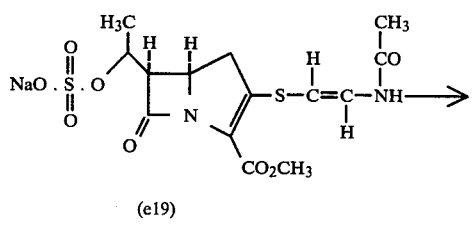
(e19)

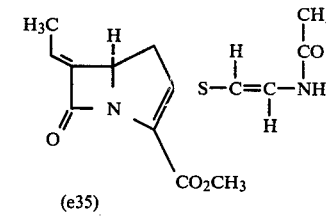
(e35)

+

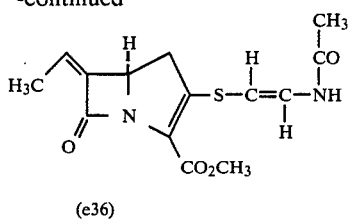

(e36)

Sodium (5R,6R)-3-[(E)-2-acetamidoethenylthio]-6-[(S)-1-sulphonatooxyethyl]-7-oxo-2-methoxycarbonyl-1-azabicyclo[3.2.0]hept-2-ene (e19) (370 mg) in dimethylformamide (6 ml) was stirred with anhydrous potassium carbonate (560 mg) at room temperature for 20 hours. Most of the dimethylformamide was removed by evaporation and the product partitioned between chloroform (25 ml) and water (25 ml). The organic layer was washed with water (3×ml) dried (MgSO$_4$) and evaporated. Chromatography of the product on silica gel (petrol-ethyl acetate as eluant) afforded a mixture of methyl (5R,6E)-3-[(E)-2-acetamidoethenylthio]-6-ethylidene-7-oxo1-azabicyclo[3.2.0]hept-2-ene-2-carboxylate and methyl (5R,6Z)-3-[(E)-2-acetamidoethylthio]-6-ethylidene-7-oxo-1-azabicyclo[3.2.0]hept-2-ene-2-carboxylate (e35 and e36) (160 mg) (ca 3:1) (e35 and e36). $\nu_{max}$ (CHCl$_3$) 1770 (B-lactam CO), 1700 and 1625 cm$^{-1}$, δ(CDCl$_3$) 1.79 (3H, d, J 7.5 Hz, C$\underline{H}_3$CH), 1.98 and 2.04 (3H, each s, CH$_3$CO for Z- and E-isomer, respectively), 3.00 and 3.05 (2H, each d, J 9 and 10 Hz, 4-CH$_2$ for E- and Z-isomer, respectively), 3.80 (C$\underline{H}_3$O$_2$C), 4.65 (1H, M, 5-CH), 5.85 (1H, d, J 14 Hz, SC$\underline{H}$=), ca 5.85 and 6.33 (1H, each qd, J 7.5 and ca 1 Hz, CH$_3$.C$\underline{H}$ for 7 and E-isomer, respectively), 7.15 (1H, dd, J 14 and 10 Hz, NHC$\underline{H}$=) and 8.02 br (1H, d, J 10 Hz, NH). [Found: M$^+$, 308.08288. C$_{14}$H$_{16}$N$_2$O$_4$S requires 308.08307].

EXAMPLE 25 p-Bromobenzyl (5R,6E)-3-[(E)-2-acetamidoethenylthio]-6-ethylidene-7-oxo-1-azabicyclo[3.2.0]hept-2-ene-2-carboxylate and p-bromobenzyl (5R,6Z)-3-[(E)-2-acetamidoethenylthio]-6-ethylidene-7-oxo-1-azabicyclo[3.2.0]hept-2-ene-2-carboxylate

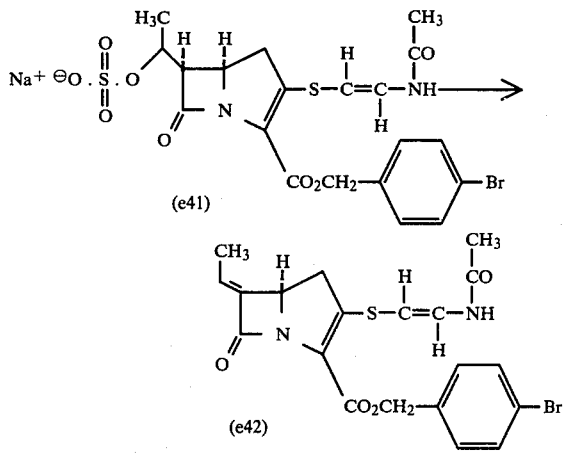

Sodium (5R,6R)-3-[(E)-2-acetamidoethenylthio]-6-[(S)-1-sulphonatooxyethyl]-7-oxo-2-p-bromobenzyloxycarbonyl-1-azabicyclo[3.2.0]hept-2-ene (e41) (300 mg) in dimethylformamide (10 ml) was stirred at room temperature with anhydrous potassium carbonate (400 mg) for 20 hours. Most of the dimethylformamide was removed by evaporation and the product was diluted with ethyl acetate. The organic extract was washed with water (3×20 ml) and brine (20 ml), and then dried (MgSO$_4$). Evaporation gave a product which was fractionated on silica gel (petrol-ethyl acetate as eluant) to afford a mixture of p-bromobenzyl (5R,6E)-3-[(E)-2-acetamidoethenylthio]-6-ethylidene-7-oxo-1-azabicyclo[3.2.0]hept-2-ene-2-carboxylate and p-bromobenzyl (5R,6Z)-3-[(E)-2-acetamidoethenylthio]-6-ethylidene-7-oxo-1-azabicyclo[3.2.0]hept-2-ene-2-carboxylate (e42) (ca. 2:7) (104 mg) $\nu_{max.}$ (CHCl$_3$) 1770, 1700 and 1625 cm$^{-1}$; (CDCl$_3$) 1.77 (3H, d, J 7.5 Hz, C$\underline{H}_3$CH), 2.02 (3H, s, CH$_3$CO), 2.98 and 3.03 (2H, each d, J 8 and 9 Hz, 4-CH$_2$ for E and Z-isomer, respectively), 4.60 (1H, m, 5-CH), 5.08 and 5.17 (2H, ABq, J 13 Hz CO$_2$C$\underline{H}_2$), 5.82 (1H, d, J 14 Hz, SC$\underline{H}$=), 5.88 and 6.34 (1H, each qd, J 7.5 and ca. 1 Hz, for Z and E-isomer, respectively), 7.0-7.5 (5H, m, NHC$\underline{H}$= and C$_6$$\underline{H}_4$Br), and 7.85 br (1H, d, J 11 Hz, NH). [Found: M$^+$, 462.02042 C$_{20}$H$_{19}$N$_2$O$_4$SBr requires 462.02493].

EXAMPLE 26

Benzyl (5R,6E)-3-[(E)-2-acetamidoethenylthio]-6-ethylidene-7-oxo-1-azabicyclo[3.2.0]hept-2-ene-2-carboxylate and benzyl (5R,6Z)-3-[(E)-2-acetamidoethenylthio]-6-ethylidene-7-oxo-1-azabicyclo[3.2.0]hept-2-ene-2-carboxylate

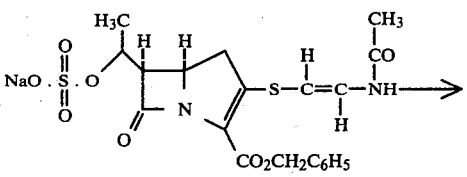

(e23)

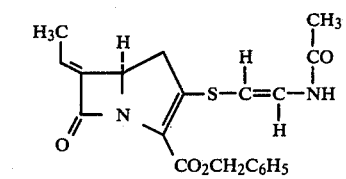

(e45)

+

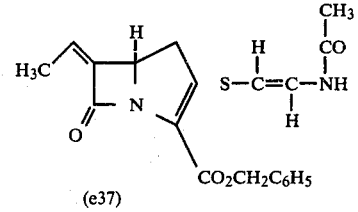

(e37)

Benzyl (5R,6R)-3-[(E)-2-acetamidoethenylthio]-6-[sodio (S)-1-sulphonatooxyethyl]-7-oxo-1-azabicyclo[3.2.0]hept-2-ene-2-carboxylate (e23) was stirred vigorously with potassium carbonate (750 mg) in dimethylformamide (10 ml) for 20 hours. The mixture was concentrated in vacuo, and the residue extracted with chloroform. The organic solution was washed with water (5×20 ml), dried (MgSO$_4$) and evaporated to give the crude product as a foam. The product was chromatographed on silica (ethyl acetate as eluant) to give benzyl (5R,)-3-[(E)-2-acetamidoethylthio]-6-ethylidene-7-oxo-1-azabicyclo[3.2.0]hept-2-ene-2-carboxylate (e45 and e37) (122 mg) in which the ratio of E- to Z-isomer was approximately 3.5:1. $\nu_{max}$. (CHCl$_3$) 3300 (br), 1770, 1700 and 1630 cm$^{-1}$; $\nu_{max}$. (EtOH) ca. 332 sh and 311 nm; δ(COCl$_3$) E-isomer, 1.76 (3H, d, J 8 Hz, C$\underline{H}_3$CH), 2.00 (3H, s, CH$_3$CO), 2.98 (2H, d, J 9 Hz, 4-CH$_2$), 4.60 (1H, m, 5-CH), 5.24 (2H, centre of AA', wings at 5.09 and 5.39, C$\underline{H}_2$Ph), 5.81 (1H, d, J 14 Hz, SC$\underline{H}$=), 6.32 (1H dq, J 8 and 1 Hz, C$\underline{H}_3$CH), 7.14 (1H, dd, J 14 and 10 Hz, NHC$\underline{H}$=), 7.30 (5H, m, PhCH$_2$) and 7.96 (1H, br, d, J 10 Hz, NH), Z-isomer as E-isomer except for 2.0 (3H, d, J 8 Hz, C$\underline{H}_3$CH), 302 (2H, d, J 9 Hz, 4-CH$_2$) and ca. 5.85 (1H, dq, J 8 and 1 Hz, CH$_3$C$\underline{H}$). Found: M+, 384.1153, C$_{20}$H$_{20}$N$_2$O$_4$S requires 384.1144.

EXAMPLE 27 p-Nitrobenzyl (5R,6Z)-3-[(E)-2-acetamidoethenylthio]-6-ethylidene-7-oxo-1-azabicyclo[3.2.0]hept-2-ene-2-carboxylate and p-Nitrobenzyl (5R,6E)-3-[(E)-2-acetamidoethenylthio]-6-ethylidene-7-oxo-1-azabicyclo[3.2.0]hept-2-ene-2-carboxylate

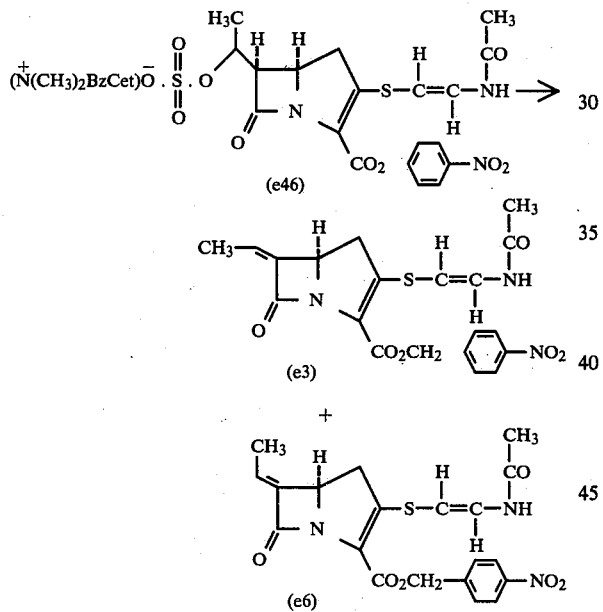

Benzyldimethyl-n-hexadecylammonium (5R,6R)-3-[(E)-2-acetamidoethenylthio]-6-[(S)-1-sulphonatooxyethyl]-7-oxo-2-p-nitrobenzyloxycarbonyl-1-azabicyclo[3.2.0]hept-2-ene (e46) (1.85 mg) was dissolved in methylene chloride (40 ml) and the solution cooled to −15°. A solution of DBU (0.634 g) in methylene chloride (10 ml) was added, and stirring was continued at −10° for 3.5 hours. The organic solution was washed with 3 portions of brine (20 ml), then dried (MgSO$_4$) and evaporated. The residue was chromatographed on silica gel eluting first with petrol/ethyl acetate (1:4) and then with ethyl acetate to yield p-nitrobenzyl (5R,6Z)-3-[(E)-2-acetamidoethenylthio]-6-ethylidene-7-oxo-1-azabicyclo[3.2.0]hept-2-ene-2-carboxylate and p-nitrobenzyl (5R,6E)-3-[(E)-2-acetamidoethenylthio]-6-ethylidene-7-oxo-1-azabicyclo[3.2.0]hept-2-ene-2-carboxylate (e3 and e6) (0.46 g) in which the E- to Z-isomer ratio was about 1:1.2. Trituration of the mixed products under ethyl acetate gave a pale yellow solid; (Found; C, 55.8; H, 4.5, N, 9.7%, M+, 429.0999. C$_{20}$H$_{19}$N$_3$O$_6$S requires C, 55.9; H, 4.5; N, 9.8%, M+ 429.0994). $\nu_{max}$ (KBr) 1760, 1690 and 1620 cm$^{-1}$; $\lambda_{max}$ (EtOH) 340sh (11,000), 310 (13,400) and 268 nm (17,400); δ (DMF-d$_7$) 1.82 and 2.00 (Total 3H, each d, J 7 Hz, C$\underline{H}_3$CH for E- and Z-isomer, respectively), ca. 1.98 (3H, s, CH$_3$CO), ca. 3.2 (2H, m, C$\underline{H}_2$C.S), 4.60–5.00 (1H, m, C$\underline{H}$.CH$_2$), 5.31 and 5.54 (each 1H, d, J 14, C$\underline{H}_2$Ar), 5.95 (1H, d, J 13.5, S.C$\underline{H}$=CH), 6.12 (dq, J 7 and 0.5 Hz, C$\underline{H}_3$CH for Z-isomer), 6.38 (dq, J 7 and 1 Hz, C$\underline{H}_3$CH for E-isomer), 7.15 (1H, dd, J 13.5 and 10.5 Hz; NH.C$\underline{H}$=CH), 7.77 and 8.22 (each 2H, d, J 9 Hz, aromatic protons).

EXAMPLE 28

Methyl (5R,6E)-3-[(E)-2-acetamidoethenylthio]-6-ethylidene-7-oxo-1-azabicyclo[3.2.0]hept-2-ene-2-carboxylate and methyl (5R,6Z)-3-[(E)-2-acetamidoethenylthio]-6-ethylidene-7-oxo-1-azabicyclo[3.2.0]hept-2-ene-2-carboxylate Separation of Isomers

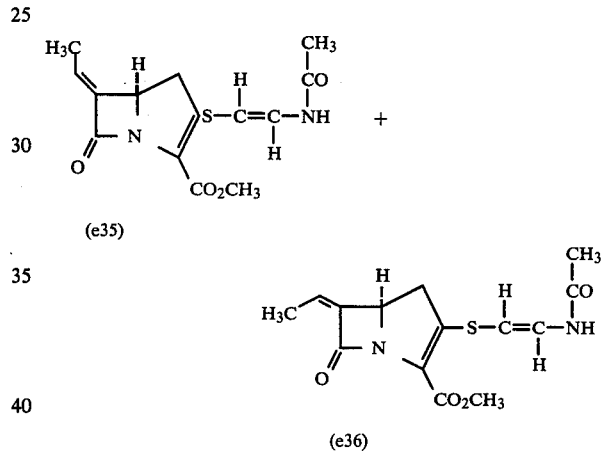

A mixture of methyl (5R,6E)-3-[(E)-2-acetamidoethenylthio]-6-ethylidene-7-oxo-1-azabicyclo[3.2.0]hept-2-ene-2-carboxylate and methyl (5R,6Z)-3-[(E)-2-acetamidoethenylthio]-6-ethylidene-7-oxo-1-azabicyclo[3.2.0]hept-2-ene-2-carboxylate (e35 and e36) (150 mg) was chromatographed on silica gel (30 g) using a gradient elution starting with chloroform and finishing with chloroform/ethanol (3:2). The product was collected in 3 separate batches. The first batch (0.02 g) consisting of the early fractions comprised of only the Z-isomer (e36) δ (CDCl$_3$) 2.03 (3H, d, C$\underline{H}_3$CH), 2.05 (3H, s, CH$_3$CO), 3.04 (2H, broad d, J 8 Hz, C$\underline{H}_2$CH), 3.80 (3H, s, CH$_3$O$_2$C), 4.62 (1H, broad t, J 8 Hz, C$\underline{H}$.CH$_2$), 5.90 [2H, m, consisting of (d, J 14 Hz, CH=C$\underline{H}$.S) and (q, CH$_3$C$\underline{H}$=)], 7.17 (1H, dd, J 14 and 10.5 Hz, CH=C$\underline{H}$.NH) and 8.25 (1H, broad d, J 10.5 Hz, NH).

The second batch of product, obtained by combining the middle fractions, was a mixture of E- and Z-isomers (e35 and e36) (0.07 g) whilst the third batch, comprising the late fractions, consisted only of the E-isomer (e35), (0.028 g), δ(CDCl$_3$) 1.81 (3H, d, J 7.5 Hz, C$\underline{H}_3$CH), 2.05 (3H, s, CH$_3$CO), 2.93 (1H, dd, J 17 and 8.5 Hz, H$_A$ of ABX), 3.17 (1H, dd, J 17 and 10 Hz, H$_B$ of ABX), 3.80 (3H, s, C$\underline{H}_3$O$_2$C), 4.70 (1H, broad t, J 9 Hz, H$_X$ of ABX), 5.87 (1H, d, J 14 Hz, S.C$\underline{H}$=CH), 6.36 (1H, dq, J 7.5 and 1 Hz, CH$_3$C$\underline{H}$.NH) and 8.23 (1H, broad d, J 10 Hz, NH).

EXAMPLE 29

Methyl (5R,6E)-3-(2-acetamidoethylthio)-6-ethylidene-7-oxo-1-azabicyclo[3.2.0]hept-2-ene-2-carboxylate and methyl (5R,6Z)-3-(2-acetamidoethylthio)-6-ethylidene-7-oxo-1-azabicyclo[3.2.0]hept-2-ene-2-carboxylate

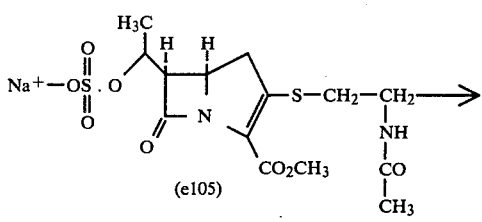

(e105)

Methyl (5R,6R)-2-(2-acetamidoethylthio)-6-[sodium(S)-1-sulphonyloxyethyl]-7-oxo-1-azabicyclo[3.2.0-]hept-2-ene-2-carboxylate (e105) (340 mg) was stirred at room temperature with potassium carbonate in dimethylformamide (10 ml) for 24 hours. The solvent was removed by evaporation, and the residue partitioned between ethyl acetate (40 ml) and water (40 ml). The organic layer was washed with water (3×20 ml) and brine (20 ml) and then dried (MgSO$_4$) and evaporated, to afford a gum (74 mg) which consisted largely of the ethylidene derivatives (e43 and e44). This material was chromatographed on silica gel using ethyl acetate to elute. Elution gave the ethylidene derivatives (e43 and e44) (40 mg)

(about 1:1); (Found: M+, 310.0979; C$_{14}$H$_{18}$N$_2$O$_4$S requires 310.0987), max (CHCl$_3$) 3450 br, 1770, 1705 and 1670 cm$^{-1}$; (CDCl$_3$) (E-isomer) 1.84 (3H, d, J 7.5 Hz, CH$_3$.CH), 1.98 (3H, s, CH$_3$CO), 2.8–3.6 (6H, m, CH$_2$.C.S.C$\underline{H}_2$C$\underline{H}_2$N), 3.87 (3H, s, CH$_3$O$_2$C), 4.77 (1H, m, CH.CH$_2$.CS), 6.25 (1H, broad, NH) and 6.45 (1H, dq, J 7.5 and 1.5 Hz, CH$_3$C$\underline{H}$=), (Z-isomer) as for E-isomer except 2.07 (3H, dd, J 7.5 and 1 Hz, C$\underline{H}_3$.CH=) and 6.01 (1H, dq, J 7.5 and 0.5 Hz, CH$_3$C$\underline{H}$=).

EXAMPLE 30

Methyl (5R,6R)-3-[(E)-2-acetamidoethenylthio]-6-[(R)-1-phenylthioethyl]-7-oxo-1-azabicyclo[3.2.0]hept-2-ene carboxylate and methyl (5R,6R)-3-[(E)-2-acetamidoethenylthio]-6-[(S)-1-phenylthioethyl]-7-oxo-1-azabicyclo[3.2.0]hept-2-ene-carboxylate

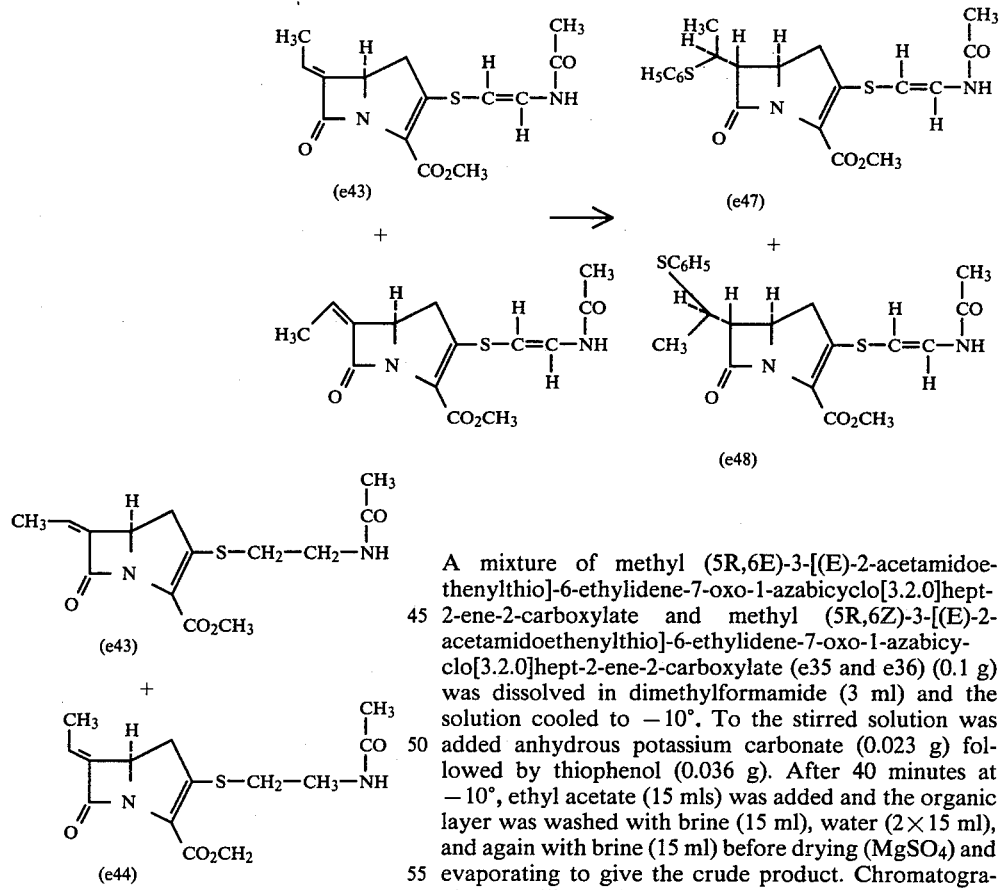

A mixture of methyl (5R,6E)-3-[(E)-2-acetamidoethenylthio]-6-ethylidene-7-oxo-1-azabicyclo[3.2.0]hept-2-ene-2-carboxylate and methyl (5R,6Z)-3-[(E)-2-acetamidoethenylthio]-6-ethylidene-7-oxo-1-azabicyclo[3.2.0]hept-2-ene-2-carboxylate (e35 and e36) (0.1 g) was dissolved in dimethylformamide (3 ml) and the solution cooled to −10°. To the stirred solution was added anhydrous potassium carbonate (0.023 g) followed by thiophenol (0.036 g). After 40 minutes at −10°, ethyl acetate (15 mls) was added and the organic layer was washed with brine (15 ml), water (2×15 ml), and again with brine (15 ml) before drying (MgSO$_4$) and evaporating to give the crude product. Chromatography on silica gel using ethylacetate/petrol mixtures (gradient elution from ethyl acetate/petrol 3:7 to neat ethyl acetate) yielded a mixture of methyl (5R,6R)-3-[(E)-2-acetamidoethenylthio]-6-[(R)-1-phenylthioethyl]-7-oxo-1-azabicyclo[3.2.0]hept-2-ene-carboxylate and the corresponding 6-[(S)-1-phenylthioethyl] stereoisomer (e48 and e47) (0.02 g). Found: M+, 418.1024; C$_{20}$H$_{22}$N$_2$O$_4$S$_2$ requires 418.1021; max. (CHCl$_3$) 1780, 1700 and 1625 cm$^{-1}$; max (EtOH) 321 and 221 nm.; (CDCl$_3$) 1.35 and 1.42 (total 3H, each d, J 6 Hz, C$\underline{H}_3$CH), 2.05 (3H, s, CH$_3$CO), 2.6 4.2 (5H, m, CH$_3$.C$\underline{H}$.C$\underline{H}$.C$\underline{H}$.C$\underline{H}_2$), 3.77 (3H, s, CH$_3$O$_2$C), (1H, d, J 13.5, CH=C$\underline{H}$.S), 7.17 (1H, dd, J 13.5 and 10.5 Hz, CH=CHNH), 7.28 (5H, br, m, PhS) and 8.27 (1H, broad d, J 10.5 Hz, NH).

EXAMPLE 31

Benzyl (5R,6R)-3-[(E)-2-acetamidoethenylthio]-6-[(R)-1-ethylthioethyl]-7-oxo-1-azabicyclo[3.2.0]hept-2-ene-2-carboxylate and benzyl (5R,6R)-3-[(E)-2-acetamidoethenylthio]-6-[(S)-1-ethylthioethyl]-7-oxo-1-azabicyclo[3.2.0]hept-2-ene carboxylate

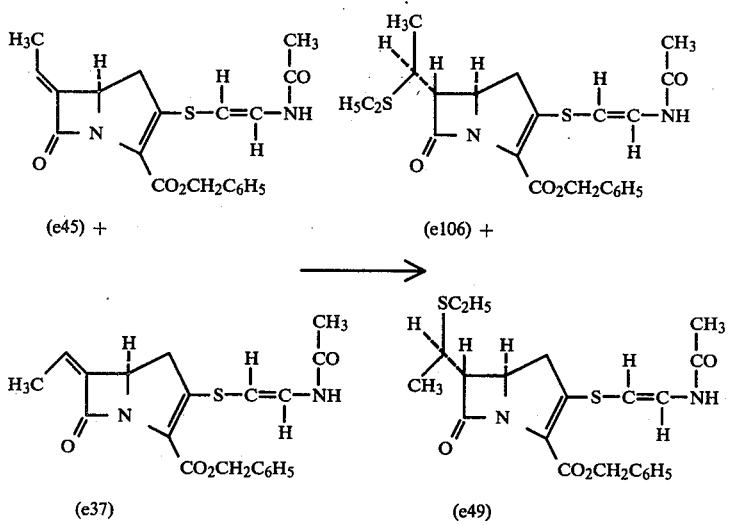

A mixture of benzyl (5R,6E)-3-[(E)-2-acetamidoethenylthio]-6-ethylidene-7-oxo-1-azabicyclo[3.2.0]hept-2-ene-2-carboxylate and benzyl (5R,6Z)-3-[(E)-2-acetamidoethenylthio]-6-ethylidene-7-oxo-1-azabicyclo[3.2.0]hept-2-ene-2-carboxylate (e45 and e37) (0.30 g) was dissolved in dimethylformamide ((5 ml) and the solution cooled to −20°. To the stirred solution was added anhydrous potassium carbonate (0.054 g) followed by ethanethiol (4 drops, estimated 1 equiv) After 25 minutes at −20°, the solution was diluted with ethyl acetate (30 ml) and the organic layer was washed with aqueous potassium carbonate (10 ml), water (30 ml) and brine (30 ml). Evaporation of the dried (MgSO$_4$) solution gave a residue which was chromatographed on silica gel using petrol/ethyl acetate as eluant. The major product (0.169 g) was an isomeric mixture of the ethylthio derivative (e106) and (e49).

The 2 isomers were separated by a combination of further chromatography on silica gel (using a gradient elution beginning with ethyl acetate/petrol, 2:3 and finishing with ethyl acetate) and crystallisation from ethyl acetate/petrol. The least polar isomer was obtained as a white crystalline solid; m.p. 191–193. [Found: C, 58.9; H, 5.7; N, 6.1%. $C_{22}H_{26}N_2O_4S_2$ requires C, 59.2 H, 5.9; N, 6.3%] $\lambda_{max}$ (EtOH) 325 (15,400) and 229 (14,900) nm $\nu_{max}$ (KBr) 1780, 1710, 1680 and 1620 cm$^{-1}$; δ(DMF-d$_7$) 1.19 (3H, t, J 7 Hz, CH$_3$CH$_2$), 1.37 (3H, d, J 6.5 Hz, CH$_3$CH), 1.98 (3H, s, CH$_3$CO), 2.60 (2H, q, J 7 Hz, CH$_2$CH$_3$), 3.20 (2H, d, J 9 Hz, CHCH$_2$). ca. 3.5 (2H, m, CH$_3$CH.CH.CH), 4.07 (1H, dt, J 3 and 9 Hz, CHCHCH$_2$), 5.24 (2H, centre of AB, wings at 5.09 and 5.38, PhCH$_2$), 5.92 (1H, d, J 14 Hz, S.CH=ch), 7.13 (1H, dd, J 10 and 14 Hz, NH.CH=CH), 7.25–7.55 (5H, m, PhCH$_2$).

The more polar isomer was isolated as a gum; $\nu_{max}$ (CHCl$_3$), 1780, 1700 and 1625 cm$^{-1}$, δ(CDCl$_3$) 1.22 (3H, t, J 7 Hz, CH$_3$C) 1.33 (3H, d, J 6.5 Hz, CH$_3$CH), 2.00 (3H, s, CH$_3$CO), 2.54 (2H, q, J 7 Hz, CH$_2$CH$_3$), 2.7–3.4 (3H, m, CH$_2$CH and CH.SEt), 3.38 (1H, dd, J 3 and 6 Hz, CH.CHCH), 4.03 (1H, m, CHCH$_2$), 5.23 (2H, centre of AB with wings at 5.08 and 5.38, CH$_2$Ph), 5.80 (1H, d, J 13.5 Hz, CH=CHS) 7.0–7.5 (6H, m, PhCH$_2$+CH=CH.NH) and 7.92 (1H, d, J 10 Hz, NH).

EXAMPLE 32 p-Nitrobenzyl (5R,6R)-3-[(E)-2-acetamidoethenylthio]-6-[(R)-1-ethylthioethyl]-7-oxo-1-azabicyclo[3.2.0]hept-2-ene-2-carboxylate and p-nitrobenzyl (5R,6R)-3-[(E)-2-acetamidoethenylthio]-6-[(S)-1-ethylthioethyl]-7-oxo-1-azabicyclo[3.2.0]hept-2-ene-carboxylate

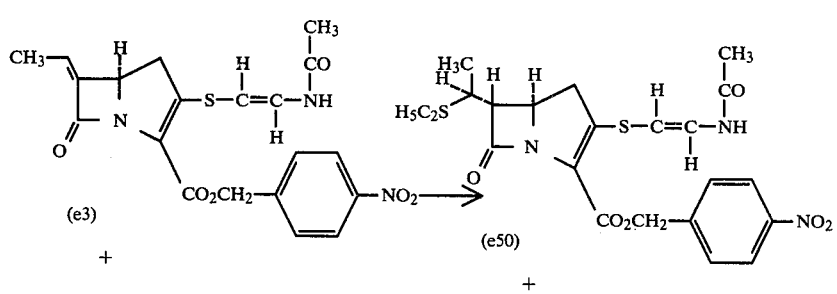

-continued

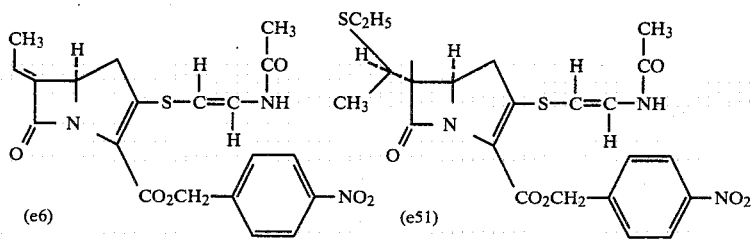

A mixture of p-nitrobenzyl (5R,6Z)-3-[(E)-2-acetamido-ethenylthio]-6-ethylidene-7-oxo-1-azabicyclo[3.2.0-]hept-2-ene-2-carboxylate and p-nitrobenzyl (5R,6E)-3-[(E)-2-acetamidoethenylthio]-6-ethylidene-7-oxo-1-azabicyclo[3.2.0]hept-2-ene-2-carboxylate (e3 and e6) (0.420 g) were dissolved in dimethylformamide (5 ml) and the solution cooled to −20°. Anhydrous potassium carbonate (0.068 g) followed by ethanethiol (0.058 g) were added to the solution which was then stirred at −20° for 20 minutes. The solution was diluted with ethyl acetate, and the organic layer was washed with aqueous potassium carbonate (10 ml), water (3×30 ml) and brine (30 ml). Evaporation of the dried (MgSO$_4$) solution gave a crude product which was chromatographed on silica gel using petrol/ethyl acetate 1:1→1:4 to elute.

The first eluted component from the column was the least polar isomer of the ethylthio-derivative which was obtained as a pale-yellow crystalline solid from ethyl acetate/petrol (0.099 g) m.p. 195°-198°. [Found: C, 53.6; H, 5.1; N, 8.6%. C$_{22}$H$_{25}$N$_3$O$_6$S$_2$ requires C, 53.8; H, 5.1; N, 8.6%. ]. λ$_{max}$ (EtOH) 327 (13,800), 266 (14,100) and 220 (14,00); ν$_{max}$ (KBr) 1775, 1690 broad and 1620 cm$^{-1}$; δ(DMF-d$_7$) 1.20 (3H, t, J 7 Hz, CH$_3$CH$_2$), 1.39 (3H, d, J 6.5 CH$_3$ CH), 1.99 (3H, s, CH$_3$CO), 2.62 (2H, q, CH$_2$CH$_3$), 3.25 (2H, d, J 9 Hz, CH$_2$CH), ca. 3.4 (1H, m, CH.SEt). 3.53 (1H, dd, J 8.5 and 3 Hz, CHCH.CH), 4.12 (1H, dt, J 3 and 9 Hz, CH.CH$_2$), 5.30 and 5.53 (each 1H, d, J 14 Hz ArCH$_2$), 5.95 (1H, d, J 13.5Hz, CH=CH.S), 7.14 (1H, dd, J 10 and 13.5 Hz, CH=CH.NH), 7.75 and 8.21 (each 2H, d, J 9 Hz, aromatic protons.

Further elution gave a product consisting of both p-nitrobenzyl (5R,6R)-3-[(E)-2-acetamidoethenylthio]-6-[(R)-1- ethylthioethyl]-7-oxo-1-azabicyclo[3.2.0]hept-2-ene-2-carboxylate and p-nitrobenzyl, (5R,6R)-3-[(E)-2-acetamido-etheneylthio]-6-[(S)-ethylthioethyl]-7-oxo-1-azabicyclo [3.2.0]hept-2-ene-carboxylate isomers (e51 and e50) (0.174 g). This was further chromatographed on silica gel to afford a pure sample of the more polar isomer as a pale-yellow foam; ν$_{max}$ (CHCl$_3$) 1780, 1700 and 1620 cm$^{-1}$. δ(DMF-d$_7$) 1.19 (3H, t, J 7 Hz, CH$_3$CH$_2$), 1.31 (3H, d, J 6.5 Hz, CH$_3$CH), 1.98 (3H, s, CH$_3$CO), 2.61 (1H, q, J 7 Hz, CH$_2$CH$_3$), 3.24 (2H, d, J 9 Hz, CH$_2$CH), ca. 3.4 (1H, m, CH.SEt), 3.75 (1H, dd, J 3 and 6 Hz, CHCHCH), 4.15 (1H, dt, J 3 and 9 Hz, CHCH$_2$), 5.29 and 5.53 (each 1H, d, J 14 Hz, CH$_2$Ar), 5.95 (1H, d, J 13.5 Hz, CH=CH.S), 7.14 (1H, dd, J 13.5 and 10.5 Hz, NHCH=CH), 7.75 and 8.20 (each 2H, d, J 9 Hz, aromatic protons) and 10.29 (1H, broad d, J 10.5 Hz, NH).

EXAMPLE 33

Sodium (5R,6R)-3-[(E)-2-acetamidoethenylthio]-6-(-1-ethylthioethyl)-7-oxo-1-azabicyclo[3.2.0]hept-2-ene carboxylate

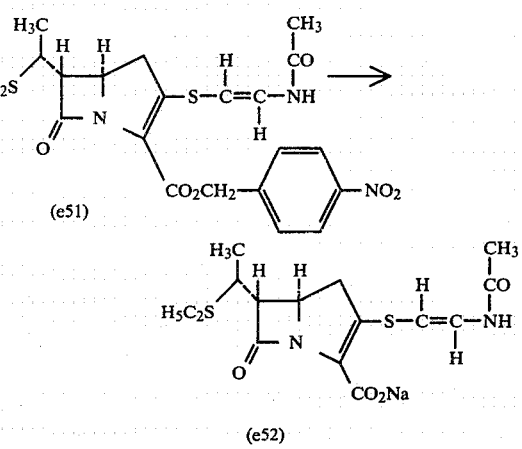

The ethylthio-derivative of Example 32 (least polar isomer) (98 mg) was added to 5% 'unreduced' Pd on C (0.150 g) which had been prehydrogenated for 0.5 hours in a mixture of dioxan (7.0 ml) and water (3.5 ml). The mixture was hydrogenated for a further 3.25 hours before adding a solution of sodium bicarbonate (17 mg) in water (1 ml). The mixture was filtered through celite washing well with water (5 ml) and dioxan (5 ml). The solution was concentrated by evaporation to a volume of about 10 ml and then was extracted with ethyl acetate (3×20 ml). The aqueous layer was evaporated in vacuo, and then evaporated down from ethanol (10 ml) and finally toluene (10 ml). Sodium (5R,6R)-3-[(E)-2-acetamidoethenylthio]-6-(-1-ethylthio-ethyl)-7-oxo-1-azabicyclo[3.2.0]hept2-ene-2-carboxylate (e52) was obtained as a yellow solid; ν$_{max}$ (EtOH) 308 and 228 nm. λ$_{max}$ (KBr) 1750 (β-lactam, 1670 (amide) and 1600 cm$^{-1}$ (broad-CO$_2$).

The sodium salt showed the following antibacterial spectrum when tested in a standard MIC test in DST agar+5% horse blood:

| | |
|---|---|
| Citrobacter freundii E8 | 3.1 |
| Enterobacter cloacae M 1 | 12.5 |
| E. coli 0111 | 3.1 |
| Klebsiella aerogenes A | 0.8 |
| Proteus mirabilis 0977 | 12.5 |
| Proteus morganii I 580 | 12.5 |
| Proteus rettgeri WM 16 | 6.25 |
| Proteus vulgaris WO 91 | 6.25 |
| Ps aeruginosa A | 100 |
| Salmonella typhimurium CT10 | 6.25 |

| | |
|---|---|
| *Serratia marcescens* US20 | 6.25 |
| *Shigella sonnei* MB 11967 | 3.1 |
| *Staph. aureus* Oxford | 0.8 |
| *Staph. aureus* Russell | 0.8 |
| *Staph. aureus* 1517 | 6.25 |
| *Strep. faecalis* I | 50 |

EXAMPLE 34

Benzyl (5R,6R)-3-[(E)-2-acetamidoethenylthio]-6-ethyl-7-oxo-1-azabicyclo[3.2.0]hept-2-ene-2-carboxylate

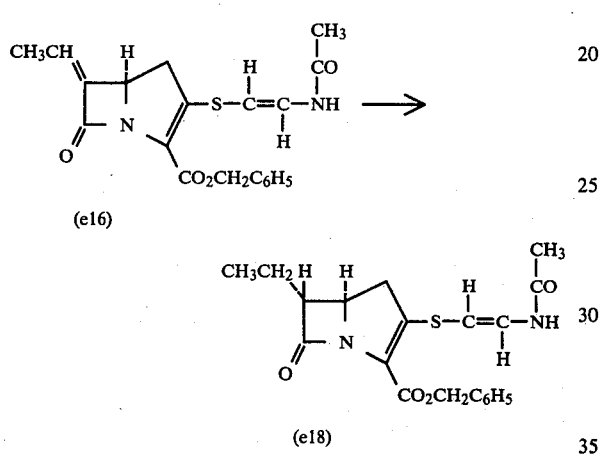

Benzyl (5R)-3-[(E)-2-acetamidoethenylthio]-6-ethylidene-7-oxo-1-azabicyclo[3.2.0]hept-2-ene-2-carboxylate (e16) (100 mg) was dissolved in a mixture of ethanol (2 ml) and pyridine (1 ml), and the solution was cooled to −5°. Sodium borohydride (9.9 mg) was added to the solution which was then stirred at −5° for 1.5 h. Ethyl acetate (20 ml) was added and the organic solution was successively washed with water (10 ml), pH 3 phosphate buffer (2×10 ml), dilute aqueous sodium bicarbonate solution (10 ml) and brine (10 ml). The dried (MgSO$_4$) organic solution was concentrated in vacuo and the residue was chromatographed on silica gel, employing a gradient elution of petroleum ether:ethyl acetate mixtures (3:7→1:9). The requisite fractions were combined and evaporated in vacuo to afford benzyl (5R6R)-3-[(E)-2-acetamidoethenylthio]-6-ethyl-7-oxo-1-azabicyclo [3.2.0]hept-2-ene-2-carboxylate (e18) (17 mg); $\lambda_{max}$ (EtOH) 325 and 228 nm., $\nu_{max}$ (CHCl$_3$) 1775, 1700 and 1625 cm$^{-1}$; δ(CDCl$_3$) 1.02 (3H, t, J 7 Hz, CH$_3$CH$_2$) 1.6–1.95 (2H, m, CH$_2$CH$_3$) 2.8–3.3 (3H, m, 4-CH$_2$ and 6-CH) 3.87 (1H, dt, J 3 and 9 Hz, 5-CH) 5.27 (2H, centre of AB with wings at 5.12 and 5.43 CH$_2$Ph) 5.85 (1H, d, J 13 Hz, =CH.S), 6.95–7.55 (6H, m, =CH.N and aromatic protons) and 7.80 (1H, br d, J 10 Hz, NH).

EXAMPLE 35 p-Nitrobenzyl (5R,6R)-3-[(E)-2-acetamidoethenylthio]-6-ethyl-7-oxo-1-azabicyclo[3.2.0]hept-2-ene-2-carboxylate

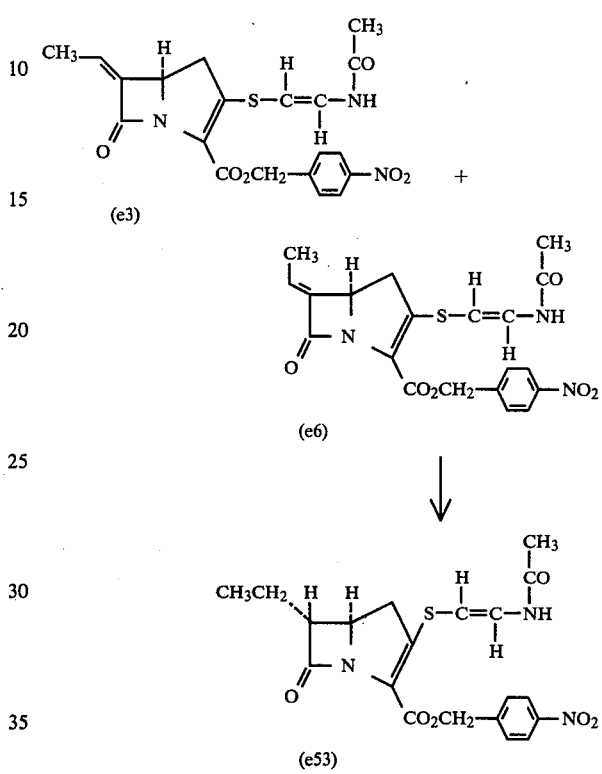

p-Nitrobenzyl (5R)-3-[(E)-2-acetamidoethenylthio]-6-ethylidene-7-oxo-1-azabicyclo[3.2.0]hept-2-ene-2-carboxylate (e3 and e6) (155 mg) was dissolved in tetrahydrofuran (10 ml). The solution was cooled to −10° and to it was added a solution of sodium borohydride (55 mg) in pH 7 buffer solution (0.5 ml). The solution was warmed to 5° and maintained at that temperature for 1.5 h. Ethyl acetate (30 ml) was added and the organic solution was washed with water (30 ml) and brine (20 ml). The solution was dried (MgSO$_4$) and evaporated in vacuo. The product was chromatographed on silica gel using petrol/ethylacetate mixtures (2:3→1.9) to elute.

The appropriate fractions were combined and evaporated in vacuo to afford p-nitrobenzyl (5R,6R)-3-[(E)-2-acetamidoethenylthio]-6-ethyl-7-oxo-1-azabicyclo[3.2.0]hept-2-ene-2-carboxylate (e53) (40 mg) as an oil; $\nu_{max}$ (EtOH) 325, 263 and 231 nm., $\nu$ max. (CHCl$_3$) 1775, 1700, and 1625 cm$^{-1}$., δ(CDCl$_3$) 1.03 (3H, t, J 7 Hz, CH$_3$CH$_2$) ca. 1.6–1.95 (2H, m, CH$_2$CH$_3$) 2.06 (3H, s, CH$_3$CO) 2.75–3.4 (3H, m, 4-CH$_2$ and 6-CH), 3.91 (1H, dt, J 3 and 9 Hz, 5-CH) 5.22 and 5.48 (each 1H, d, J 9 Hz, CH$_2$Ar) 5.88 (1H, d, J 14 Hz, =CH S) 7.20 (1H, dd, J 11 and 14 Hz, =CH—N) 7.63 and 8.19 (each 2H, d, J 8.5 Hz, aromatic protons) and 8.05 (1H, br d, J 11 Hz, NH) [Found: M+431.1179, C$_{20}$H$_{21}$N$_3$O$_6$S requires M+, 431.1150].

EXAMPLE 36

Sodium (5R,6R)-3-[(E)-2-acetamidoethenylthio]-6-ethyl-7-oxo-1-azabicyclo[3.2.0]hept-2-ene-2-carboxylate

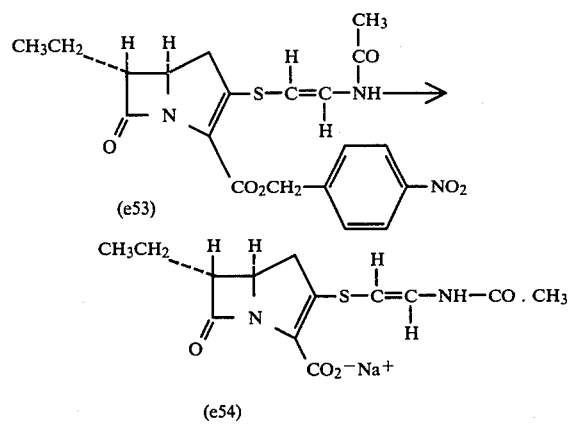

(e53)

(e54)

A solution of the ester from Example 35 (e53) (40 mg) in 20% aqueous dioxan (3 ml) was added to a mixture of 5% Pd on C and 20% aqueous dioxan (6 ml) which had been prehydrogenated at 20° and atmospheric pressure for 0.5 h. Hydrogenation was continued for 4 h and sodium bicarbonate (8 mg) was then added. The mixture was filtered over Hiflo, washing well with water, and the aqueous solution was concentrated in vacuo to a volume of 10 ml. The aqueous solution was washed with ethyl acetate (3×25 ml) and was then further concentrated to a volume of 3 ml. The solution was then chromatographed on a column (15×2.5 cm) of Biogel P2, eluting with deionised water. Fractions were monitored by UV and those having a chromophore at $\lambda_{max}$ (H$_2$O) 307 and 226 nm contained sodium (5R,6R)-3-[(E)-2-acetamidoethenylthio]-6-ethyl-7-oxo-1-azabicyclo[3.2.0]hept-2-ene-2-carboxylate (e54).

The minimum inhibitory concentrations (MIC) of the compound (e54) was determined using a standard DST agar+10% horse blood substrate. The tests used an undiluted inoculum of bacteria. The results are shown below.

| ORGANISM | MIC (μg/ml) |
|---|---|
| Citrobacter freundii E8 | 12.5 |
| Enterobacter cloacae N1 | 25 |
| Escherichia coli O111 | 3.1 |
| Escherichia coli JT 39 | 3.1 |
| Klebsiella aerogenes A | 3.1 |
| Proteus mirabilis C977 | 25 |
| Proteus morganii I580 | 25 |
| Proteus rettgeri WM16 | 25 |
| Proteus vulgaris WO91 | 25 |
| Pseudomonas aeruginosa A | >50 |
| Salmonella typhimurium CT10 | 3.1 |
| Serratia marcescens US20 | 12.5 |
| Shigella sonnei MB 11967 | 3.1 |
| Bacillus subtilis A | 0.8 |
| Staphylococcus aureus Oxford | 0.4 |
| Staphylococcus aureus Russell | 0.4 |
| Staphylococcus aureus 1517 | 12.5 |
| Streptococcus faecalis I | 25 |
| Streptococcus pneumoniae CN33 | 0.1 |
| Streptococcus pyogenes CN10 | 0.2 |
| E. coli ESS | 0.4 |

EXAMPLE 37

Sodium (5R,6R)-3-(2-acetamidoethylthio)-6-[(S)-1-sulphonatooxyethyl]-7-oxo-2-p-methoxycarbonylbenzyloxycarbonyl-1-azabicyclo-[3.2.0]hept-2-ene

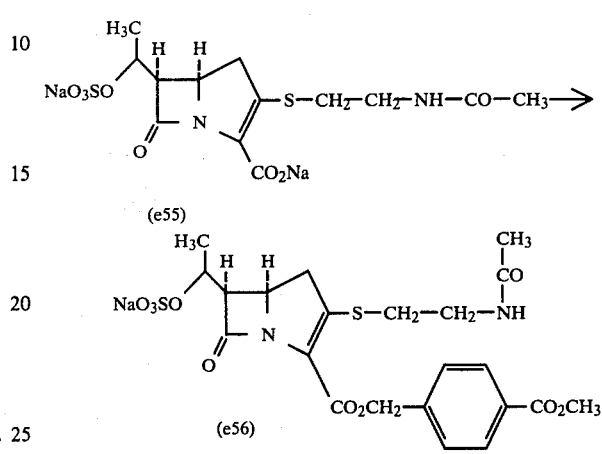

(e55)

(e56)

The di-salt (e55) (2.93 g) was suspended in DMF (50 ml) and treated with methyl 4-bromomehylbenzoate (4.5 g). After 3 h., the solvent was removed in vacuo and the residual oil was suspended in CHCl$_3$ (70 ml) and silica gel (20 g; 230–400 mesh) was added. The chloroform was removed in vacuo, and the residue was re-suspended in chloroform (30 ml) and loaded on a silica gel column (100 g; 2:1 mixture of 230–400 mesh and <230 mesh). The column was eluted with chloroform (200 ml), ethanol/chloroform (3:7, 100 ml), ethanol/chloroform (4:6, 500 ml) and ethanol/chloroform (1:1), to yield Sodium (5R,6R)-3-(2-acetamidoethylthio)-6-[(S)-1-sulphonatoxyethyl]-7-oxo-2-p-methoxycarbonylbenzyloxycarbonyl-1-azabicyclo[3.2.0]hept-2-ene (e56) (2.06 g). $\lambda_{max}$ (H$_2$O): 317 ($\epsilon$10100) and 234 ($\epsilon$15900) nm. $\nu$max (KBr): 1790, 1750, 1718, 1700, 1650 cm$^{-1}$. δ(DMSO-d$_6$): inter alia 1.38 (3H,d,J 6 Hz, C$\underline{H}_3$CH), 1.80 (3H,s,C$\underline{H}_3$CO), 3.83 (3H,s,CO$_2$C$\underline{H}_3$), 4.0–4.6 (2H,m,CH$_3$C$\underline{H}$ and C5-$\underline{H}$), 5.20 and 5.37 (2H, ABq, J 15 Hz, C$\underline{H}_2$Ar), 7.56 and 7.96 (each 2H, d,J 8 Hz,C$_6$$\underline{H}_4$), 8.1 (broad, N$\underline{H}$).

EXAMPLE 38 p-Methoxycarbonylbenzyl (5R)-3-(2-acetamidoethylthio)-6-[(E, Z)-ethylidene]-7-oxo-1-azabicyclo[3.2.0]hept-2-ene-2-carboxylate

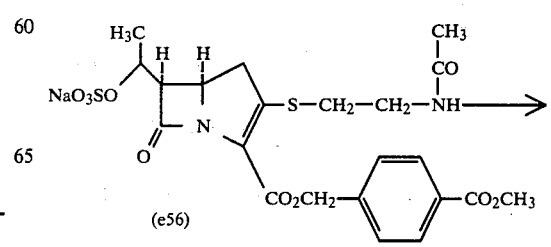

(e56)

-continued

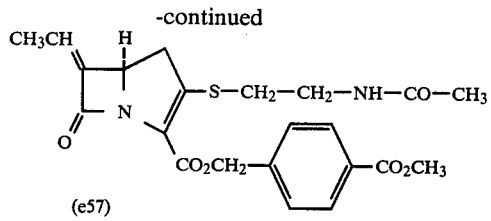
(e57)

The mono-ester (e56) (164 mg) in water (10 ml) was shaken with benzyldimethyl-n-hexadecylammonium chloride (115 mg) in $CH_2Cl_2$ (10 ml). The organic layer was separated, dried ($MgSO_4$) and evaporated in vacuo to leave the quaternary ammonium salt. This was redissolved in $CH_2Cl_2$ (4 ml), cooled in an ice bath and treated with 1,5-diazabicyclo[5.4.0]undec-5-ene (DBU) (90 mg) in $CH_2Cl_2$ (1 ml). The reaction mixture was stirred for 3 h., then washed with water (10 ml) and dilute brine (10 ml). The organic layer was dried ($MgSO_4$) and evaporated to leave a gum, which was chromatographed on silica gel (5 g, 230–400 mesh) eluting with $CHCl_3$ followed by $CHCl_3$/EtOH (95:5) to give p-methoxycarbonylbenzyl 3-(2-acetamidoethylthio)-6-[(E, Z)-ethylidene]-7-oxo-1-azabicyclo [3.2.0]hept-2-ene-2-carboxylate (e57) (22 mg). $\nu_{max}$ ($CH_2Cl_2$) 3450, 1767, 1720, 1687 cm$^{-1}$. $\delta$($CDCl_3$) 1.82 and 2.05 (total 3H, each d, J ca. 7.5 Hz, C$\underline{H}_3$CH, E and Z, ratio ca. 2:1), 1.94 (3H,s,C$\underline{H}_3$CO), 2.6–3.6 (6H,m,SC$\underline{H}_2$, C$\underline{H}_2$NH, 4-C$\underline{H}_2$),3.88 (3H,s,CO$_2$C$\underline{H}_3$), 4.5–4.9. (1H,m,C5-$\underline{H}$) 5.23 and 5.45 (2H, AB$_q$, J 15 Hz, C$\underline{H}_2$Ar), 5.95 and 6.41 (total 1H, each broad q, J ca 7.5 Hz, CH$_3$C$\underline{H}$, Z and E), 6.1 (1H, broad, N$\underline{H}$), 7.55 and 8.01 (each 2H, d, J 8 Hz, C$_6\underline{H}_4$).

EXAMPLE 39 p-Methoxycarbonylbenzyl (5R, 6S)-3-(2-acetamidoethylthio)-6-ethyl-7-oxo-1-azabicyclo[3.2.0]hept-2-ene-2-carboxylate

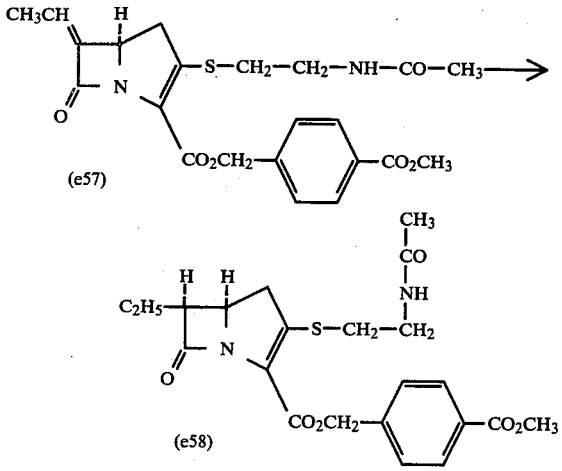

p-Methoxycarbonylbenzyl-3-(2-acetamidoethylthio)-6-[(E,Z)-ethyldiene]-7-oxo-1-azabicyclo[3.2.0]hept-2-ene-2-carboxylate (e57) (20 mg) in ethyl acetate (10 ml) was hydrogenated over $PtO_2$ (25 mg) for 18 h. a atmospheric pressure. The catalyst was filtered off and the filtrate was chromatographed on silica gel (5 g, 230–400 mesh), eluting with ethyl acetate/2% ethanol, and collecting 2 ml fractions. Fractions 31–39 were combined and evaporated in vacuo to yield p-methoxycarbonylbenzyl (5R,6S)-3-(2-acetamidoethylthio)-6-ethyl-7-oxo-1- azabicyclo [3.2.0]hept-2-ene-2-carboxylate (e58) (6.6 mg). $\lambda$max (EtOH) 317 and 233 nm $\nu$max ($CH_2Cl_2$) 3450, 1780, 1720, 1680 cm$^{-1}$ $\delta$($CDCl_3$) 1.05 (3H, t, J ca. 7 Hz, C$\underline{H}_3$CH$_2$), 1.5–1.8 (2H, m, CH$_3$C$\underline{H}_2$), 1.96 (3H, s, CH$_3$CO), 2.8–3.7 (7H, m, SC$\underline{H}_2$, C$\underline{H}_2$NH, 4-C$\underline{H}_2$, C6-$\underline{H}$) 3.90 (3H, s, CO$_2$CH$_3$), 4.0–4.5 (1H, m, C5-$\underline{H}$). 5.16 and 5.42 (2H, AB$_q$, J ca. 14 Hz, C$\underline{H}_2$Ar), 5.8 (1H, broad s, NH), 7.50 and 8.00 (each 2H, d, J 8 Hz, C$_6\underline{H}_4$). Found: M$^+$ 446.1539; $C_{22}H_{26}N_2O_6S$ requires M$^+$ 446.1509.

EXAMPLE 40 p-Methoxycarbonylbenzyl (5R,6R)-3-(2-acetamidoethylthio)-6-[(S) -1-ethoxysulphonyloxyethyl]-7-oxo-1-azabicyclo-[3.2.0]hept-2-ene-2-carboxylate

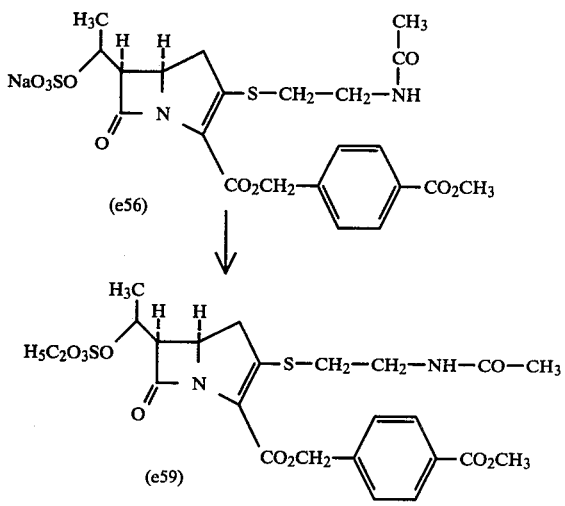

Method I

Sodium (5R,6R)-3-(2-acetamidoethylthio)-6-[(S)-1-sulphonatooxyethyl]-7-oxo-2-p-methoxycarbonylbenzyloxycarbonyl-1-azabicyclo[3.2.0]hept-2-ene (e56) (50 mg) was suspended in dry $CH_2Cl_2$ (2 ml) and treated with $Et_3OBF_4$ in $CH_2Cl_2$ (100 mg/ml; 0.19 ml). The mixture was stirred for 0.75 h. then washed with water, dried ($MgSO_4$) and evaporated to yield p-methoxycarbonylbenzyl (5R,6R)-3-(2-acetamidoethylthio)-6-[(S)-1-ethoxysulphonyloxyethyl]-7-oxo-1-azabicyclo[3.2.0-]hept-2-ene-2-carboxylate (e59).

Method II

Sodium (5R,6R)-3-(2-acetamidoethylthio)-6-[(S)-1-sulphonatooxyethyl]-7-oxo-2-p-methoxycarbonylbenzyloxycarbonyl-1-azabicyclo[3.2.0]hept-2-ene (e56) (50 mg) in $H_2O$ (5 ml) was shaken with (n-$C_{16}H_{33}$) ($C_6H_5CH_2$) ($CH_3$)$_2$ N$^+$Cl$^-$ (40 mg) in $CH_2Cl_2$ (10 ml). The organic layer was separated, dried ($MgSO_4$) and evaporated to yield the quaternary ammonium salt. This was taken up in dry $CH_2Cl_2$ and treated with $Et_3OBF_4$ in $CH_2Cl_2$ (100 mg/ml, 0.19 ml). After 0.5 h., a further 0.05 ml of $Et_3OBF_4$ solution was added. After 5 min., the solution was washed with water dried ($MgSO_4$) and evaporated to leave p-methoxycarbonylbenzyl (5R,6R)-3-(2-acetamidoethylthio)-6-[(S)-1-ethoxysulphonyloxyethyl]-7-oxo-1-azabicyclo[3.2.0]hept-2-ene-2-carboxylate (e59), contaminated with the quaternary ammonium tetrafluoroborate.

EXAMPLE 41 p-Methoxycarbonylbenzyl (5R)-3-(2-acetamidoethylthio)-6-[(E)-ethylidene)-7-oxo-1-azabicyclo[3.2.0]hept-2-ene-2-carboxylate

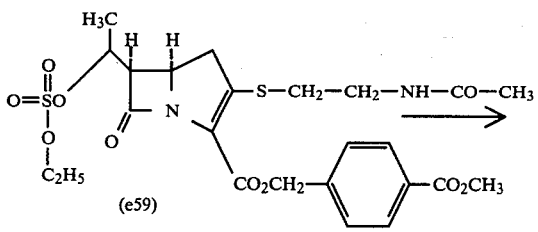
(e59)

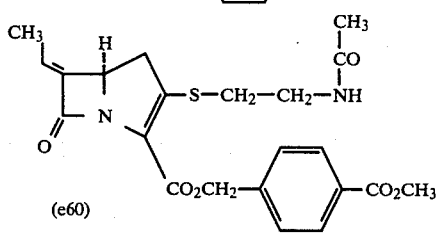
(e60)

p-Methoxycarbonylbenzyl (5R,6R)-3-(2-acetamidoethylthio)-6-[(S)-1-ethoxysulphonyloxyethyl]-7-oxo-1-azabicyclo [3.2.0]hept-2-ene-2-carboxylate from Example 40, Method II, was taken up in DMF (2 ml) and treated with powdered K$_2$CO$_3$(50 mg). The mixture was stirred for 1.5 h, then the solvent was evaporated in vacuo and the residue was dissolved in ethyl acetate (10 ml) and water (10 ml) and shaken. The ethyl acetate layer was separated, washed with water (3×10 ml) then brine, dried (MgSO$_4$) and evaporated in vacuo. The residue was chromatographed on silica gel (3 g, 230-400 mesh), eluting with ethyl acetate/4% ethanol, to give, after evaporation of the solvent, p-methoxycarbonylbenzyl (5R)-3-(2-acetamidoethylthio)-6-[(E)-ethylidene)]-7-oxo-1-azabicyclo[3.2.0]hept-2-ene-2-carboxylate (e60) (8.2 mg). δ(CDCl$_3$) 1.89 (3H, d, J 7 Hz, CH$_3$CH), 1.95 (3H, s, CH$_3$CO), 2.7-3.7 (6H, m, SCH$_2$, CH$_2$NH, 4-CH$_2$ ), 3.90 (3H, s, CO$_2$CH$_3$), 4.75 (1H, broad t, J ca. 9 Hz, 5-CH), 5.22 and 5.43 (2H, ABq, J ca. 14 Hz, CH$_2$Ar), 5.8 (1H, broad, NH), 6.40 (1H, dq, J ca. 1 and 7 Hz, CH$_3$CH) 7.52 and 8.00 (each 2H, d, J 8 Hz, C$_6$H$_4$).

EXAMPLE 42

Benzyl (5R)-3-[(Z)-2-acetamidoethenylthio]-6-[(EZ)-ethylidene]-7-oxo-1-azabicyclo[3.2.0]hept-2-ene-2-carboxylate

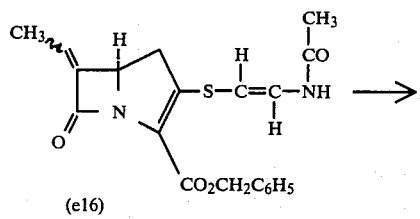
(e16)

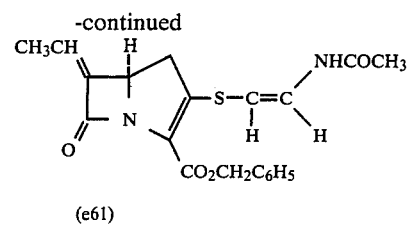
(e61)

A solution of benzyl (5R)-3-[(E)-2-acetamidoethenylthio-6-ethylidene-7-oxo-1-azabicyclo[3.2.0]hept-2-ene-2-carboxylate [40 mg of an approximately 1:1 mixture of (E)- and (Z)-ethylidene isomers] in 20% aqueous acetonitrile (0.5 ml) was stirred with mercuric chloride (27 mg) at room temperature for 5 min. The solution was diluted with ethyl acetate and the organic phase was washed twice with aqueous sodium bicarbonate solution and brine. The solution was dried (MgSO$_4$) and concentrated in vacuo. The residue was chromatographed on silica gel, eluting with petroleum ether (60°-80°)/ethyl acetate (1:4) to afford benzyl (5R)-3-[(Z)-2-acetamidoethenylthio)-6-[(EZ)-ethylidene]-7-oxo-1-azabicyclo[3.2.0]hept-2-ene-2-carboxylate (e61) (approximately 1:1 mixture of isomers) (15 mg) as a gum; λ$_{max.}$ (EtOH) 312 and 223 nm; ν$_{max}$ (CHCl$_3$) 3410, 1770, 1700 and 1630 cm$^{-1}$; δ(CDCl$_3$) 1.78 and 2.03 [3H, each d, J 7 Hz,CH$_3$CH for (6E) and (6Z)-isomers, respectively], 2.07 (3H, s, CH$_3$CO) 2.75–3.30 (2H, m, 4-CH$_2$), 4.50–4.80 (1H, m, 5-CH), 5.05–5.47 (3H, m, CH$_2$ Ph and SCH=), 5.91 and 6.38 [1H, each dq, J ca 1 and 7 Hz, CH=CH$_3$ for (6Z)- and (6E)-isomers, respectively], 7.15–7.6 (6H, m, C$_6$H$_5$ and =CHN) and 7.94 (1H, br, d, NH).

EXAMPLE 43

Benzyl (5R,6R)-3-[(Z)-2-acetamidoethenylthio]-6-ethyl-7-oxo-1-azabicyclo[3.2.0]hept-2-ene-2-carboxylate

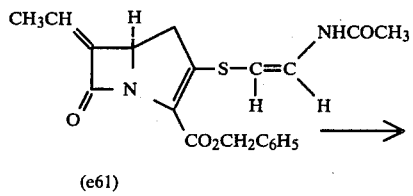
(e61)

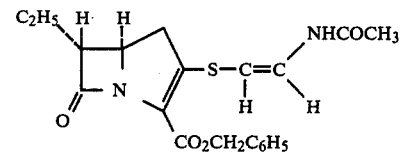
(e62)

To a solution of benzyl (5R)-3-[(Z)-2-acetamidoethenylthio]-6-[(EZ)-ethylidene]-7-oxo-1-azabicyclo [3.2.0]hept-2-ene-2-carboxylate (e61) (25 mg) in THF (1 ml) at −5° was added a solution of sodium borohydride (9 mg) in aqueous pH 7 buffer solution (0.1 ml). The mixture was allowed to warm to 5° C. and then was left to stand for 0.5 h. Ethyl acetate (20 ml) was added and the organic solution was washed with water and brine. Evaporation of the dried (MgSO$_4$) solution gave a residue which was chromatographed on silica gel using petroleum ether (60°-80°)/ethyl acetate (2:3) to elute. The first eluted component was benzyl (5R,6R)-3-[(Z)-

2-acetamidoethenylthio]-6-ethyl-7-oxo-1-azabicyclo[3.2.0]hept-2-ene-2-carboxylate (e62) (3 mg); λmax. (EtOH) 324 nm; ν$_{max}$. (CHCl$_3$) 3410, 1775, 1700 and 1630 cm.

EXAMPLE 44

Sodium (5R,6S)-3-(2-acetamidoethylthio)--6-ethyl-7-oxo-1-azabicyclo[3.2.0]-hept-2-ene-2-carboxylate

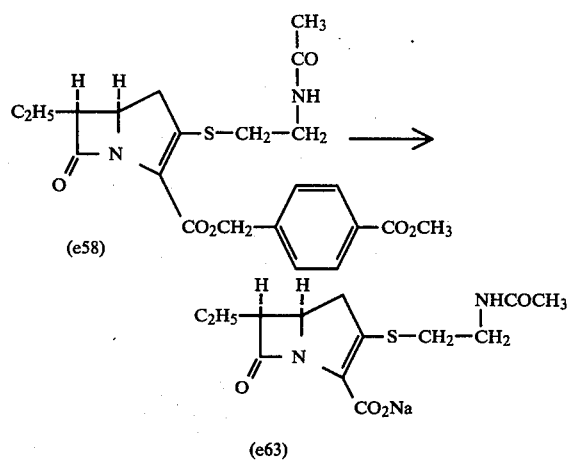

p-Methoxycarbonylbenzyl (5R,6S)-3-(2-acetamidoethylthio)-6-ethyl-7-oxo-1-azabicyclo[3.2.0]hept-2-ene-2-carboxylate (e58) (18 mg) was added to the cathodic compartment of an H-type divided two-compartment electrochemical cell, with a mercury cathode and a platinum anode. The cell contained degassed 0.1 M n-Bu$_4$NI in dimethylformamide as electrolyte. The volume of the catholyte was about 15 ml [glacial acetic acid (about 10 mg) added] and the volume of the anolyte was about 8 ml. A potentiostat was employed to fix the potential of the cathode at −1.9 V with respect to the standard calomel electrode, and the initial current, about 56 mA, fell to about 15 mA after about 15 min. The catholyte was removed from the cell and the solvent was evaporated in vacuo. The residue was taken up in CH$_2$Cl$_2$ (10 ml) and washed with water (10 ml). The aqueous phase was separated and washed with CH$_2$Cl$_2$. The aqueous phase, containing the tetrabutylammonium salt corresponding to (e63) was passed through an Amberlite IR 120 (Na form) column (17×1 cm) and the eluate was reduced to low volume by evaporation in vacuo. The residue was passed through a Biogel P-2 column, to yield fractions containing sodium (5R,6S)-3-(2-acetamidoethylthio)-6-ethyl-7-oxo-1-azabicyclo[3.2.0]hept-2-ene-2-carboxylate (e63) having λ$_{max}$ 298 nm. The minimum inhibitory concentrations (MIC) of this compound was determined using a standard DST agar+10% horse blood substrate.

The results are shown below.

| ORGANISM | MIC (μg/ml) |
| --- | --- |
| Citrobacter freundii E8 | 2.5 |
| Enterobactor cloacae N1 | 20 |
| Escherichia coli 0111 | 2.5 |
| Escherichia coli JT 39 | 10 |
| Klebsiella aerogenes A | 1.2 |
| Proteus mirabilis C977 | 10 |
| Proteus morganii I580 | 40 |
| Proteus rettgeri WM16 | 10 |
| Proteus vulgaris W091 | 5.0 |
| Pseudomonas aeruginosa A | >40 |
| Salmonella typhimurium CT10 | 2.5 |
| Serratia marcescens US20 | 10 |
| Shigella sonnei MB 11967 | 2.5 |
| Bacillus subtilis A | — |
| Staphylococcus aureus Oxford | 0.6 |
| Staphylococcus aureus Russell | 0.6 |
| Staphylococcus aureus 1517 | 10 |
| Streptococcus faecalis I | 40 |
| Streptococcus pneumoniae CN33 | NG |
| Streptococcus pyogenes CN10 | 0.1 |
| E. coli ESS | 1.2 |

EXAMPLE 45 tert-Butyldiphenylsilyl (5R,6S)-3-[(E)-2-acetamidoethenylthio]-6-[(1S)-1-hydroxyethyl]-7-oxo-1-azabicyclo[3.2.0]hept-2-ene-2-carboxylate

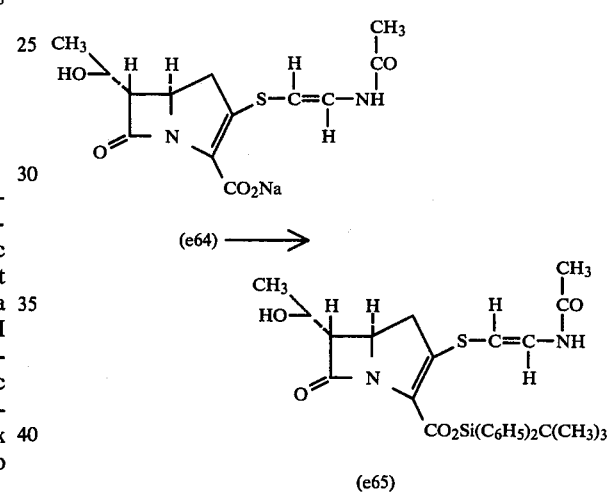

Method I

Sodium (5R,6S)-3-[(E)-2-acetamidoethenylthio]-6-[(S)-1-hydroxyethyl]-7-oxo-1-azabicyclo[3.2.0]hept-2-ene-2-carboxylate (e64) (50 mg, 50% pure material) in dry tetrahydrofuran (THF) (5 ml) containing 15-crown-5 crown ether (2 drops) and 3 Å molecular sieves was treated with tert-butylchlorodiphenylsilane (80 mg). After stirring at r.t. for 20 hr., the THF was evaporated in vacuo and the mixture loaded onto a silica gel column (10 g) and the column eluted with chloroform (10 ml) followed by a chloroform/ethanol mixture (4:1). The fractions containing the ester were combined and evaporated to give tert-Butyldiphenylsilyl (5R,6S)-3-[(E)-2-acetamidoethenylthio]-6-[(S)-1-hydroxyethyl]-7-oxo-1-azabicyclo[3.2.0]hept-2-ene-2-carboxylate (e65) as an oil (20 mg), νmax (CH$_2$Cl$_2$) 1785, 1700, 1685, 1625 cm$^{-1}$. δ(CDCl$_3$) 1.13 (9H,s,C(C$\underline{H}_3$)$_3$), 1.27 (3H,d,J 6 Hz, C$\underline{H}_3$CH), 1.77 (3H,s,C$\underline{H}_3$CO), 2.7–3.2 (2H,m, 4—C$\underline{H}_2$), 3.22 (1H, m, sharpens to dd on D$_2$O exchange, J$_1$ approx. 5 Hz, J$_2$ approx. 3 Hz, 6—C$\underline{H}$), 3.6 (1H, broad, exchanges D$_2$O, O$\underline{H}$), 3.9–4.3 (2H,m, 5—C$\underline{H}$, 8—C$\underline{H}$), 5.60 (1H,d,J 14 Hz, S C$\underline{H}$=), 7.02 (1H,dd,J$_1$ 14 Hz, J$_2$ 10 Hz,d,J 14 Hz on D$_2$O exchange, CH=C$\underline{H}$ NH), 7.3–7.8 (10H, Ar—$\underline{H}$), 8.34 (1H, broad d, exchange D$_2$O, N$\underline{H}$)

p.p.m. The UV spectrum showed a maximum at about 328 nm.

Method II

The sodium salt (e64) (50 mg; 50% pure) in N,N-dimethylformamide (DMF) (2 ml) was stirred with 3 Å molecular sieves (200 mg) for ¾ hr. tert-Butylchlorodiphenylsilane (50 mg) was then added and the mixture was stirred for 15 min. Most of the DMF was then removed by evaporation in vacuo. Ethyl acetate was added, the mixture was filtered through celite and the resultant solution was washed with dilute aqueous $NaHCO_3$ followed by water. The ethyl acetate was dried ($MgSO_4$), evaporated in vacuo to give the crude ester. Chromatography on silica gel yielded pure tert-Butyldiphenylsilyl (5R,6S)-3-[(E)-2-acetamidoethenylthio]-6-[(1S)-1-hydroxyethyl]-7-oxo-1-azabicyclo[3.2.0-]hept-2-ene-2-carboxylate (e65).

Method III

The sodium salt (e64) (50 mg, 50% pure) in acetonitrile (3 ml) was stirred with 3 Å molecular sieves (150 mg) and 15-crown-5 crown ether (2 drops) for 1 hr. tert-Butylchorodiphenylsilane (about 40 mg) was added and stirring was continued for 1 hr. The reaction mixture was worked up as in method I to give tert-Butyldiphenylsilyl (5R,6S)-3-[(E)-2-acetamidoethenylthio]-6-[(1S)-1-hydroxyethyl]-7-oxo-1-azabicyclo[3.2.0]hept-2-ene-2-carboxylate (e65) (13 mg).

EXAMPLE 46 tert-Butyldiphenylsilyl (5R,6S)-3-[(E)-2-acetamidoethenylthio]-6-[(1S)-1-methylsulphonyloxyethyl]-7-oxo-1-azabicyclo[3.2.0-]hept-2-ene-2-carboxylate

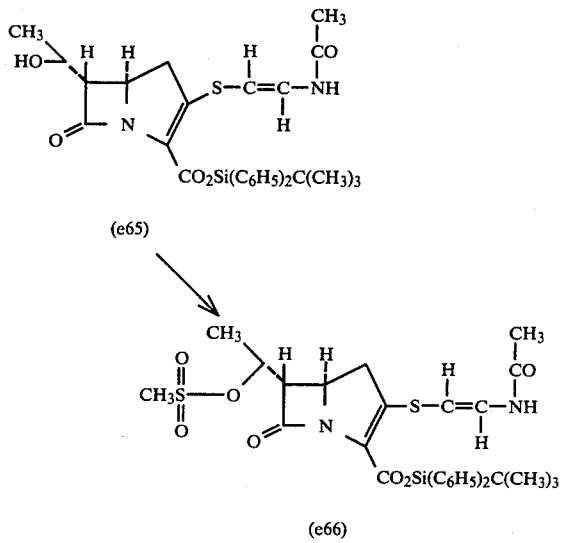

tert-Butyldiphenylsilyl (5R,6S)-3-[(E)-2-acetamidoethenylthio]-6-[(1S)-1-hydroxyethyl]-7-oxo-1-azabicyclo[3.2.0]hept-2-ene-2-carboxylate (e65) (45 mg) in $CH_2Cl_2$ (1 ml) was cooled to $-20°$ C. and treated with a solution of triethylamine in $CH_2Cl_2$ (0.13 ml, 100 mg/ml) followed by a solution of methane sulphonyl chloride in $CH_2Cl_2$ (0.11 ml, 100 mg/ml). The mixture was stirred whilst maintaining the temperature between $-20°$ C. and $0°$ C. for 6 hr. The reaction mixture was then diluted with $CH_2Cl_2$, washed with water and then with brine, dried ($MgSO_4$) and evaporated in vacuo. The residue was chromatographed on a silica gel column (3-4 g, 230-400 mesh ASTM) to give tert-Butyldiphenylsilyl (5R,6S)-3-[(E)-2-acetamidoethenylthio]-6-[(1S)-1-methylsulphonyloxyethyl]-7-oxo-1-azabicyclo[3.2.0]hept-2-ene-2-carboxylate (e66) (20 mg), νmax 3440, 1785, 1700, 1685($sh$), 1625 cm$^{-1}$. δ($CDCl_3$) 1.12 [9H,s,C($CH_3$)$_3$], 1.54 (3H,d,J Ca 6 Hz, $CH_3$CH), 1.84 (3H,s,CO$CH_3$), 3.00 (5H, s superposed on m, $CH_3SO_3$, 4—$CH_2$), 3.4-3.6 (1H,m,dd,J 3 and 5 Hz on $D_2O$ exchange, 6—$CH$), 4.0-4.3 (1H,m,5—$CH$), 4.9-5.3 (1H,m,8—$CH$), 5.64 (1H,d,J 14 Hz, $SCH$=CH), 7.08 (1H,dd,J 14 and 10 Hz, d, J 14 Hz on $D_2O$ exchange, $CH$ NH), 7.2-7.8 (10 H,m, ($C_6H_5$)$_2$), 7.90 (1H,d,J 10 Hz, exchanges $D_2O$, N$H$)ppm.

EXAMPLE 47 tert-Butyldiphenylsilyl (5R)-3-[(E)-2-acetamidoethenylthio]-6-[(Z)-ethylidene]-7-oxo-1-azabicyclo[3.2.0 hept-2-ene-2-carboxylate

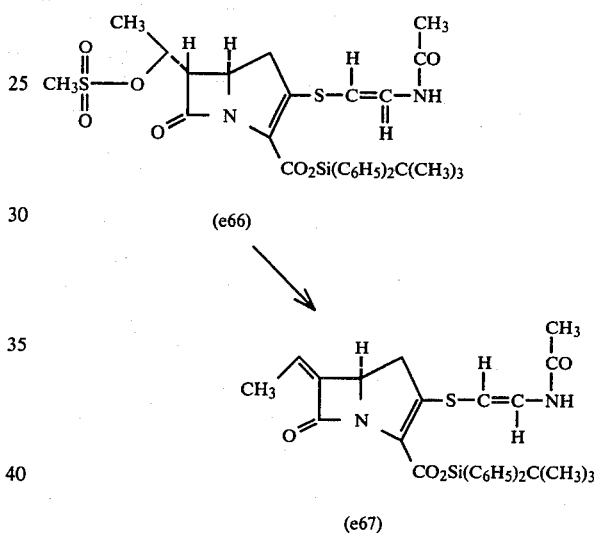

Method I tert-Butyldiphenylsilyl (5R,6S)-3-[(E)-2-acetamidoethenylthio]-6-[(1S)-1-methylsulphonyloxyethyl]-7-oxo-1-azabicyclo[3.2.0]hept-2-ene-2-carboxylate (20 mg) in dichloromethane (1 ml) was treated with 1,5-diazabicyclo[5.4.0]undec-5-ene (0.05 ml of a 100 mg/ml solution in $CH_2Cl_2$) at room temperature for 20 min. The dichloromethane solution was diluted, washed with water, dried ($MgSO_4$) and evaporated in vacuo to give tert-Butyldiphenylsilyl (5R)-3-[(E)-2-acetamidoethenylthio]-6-[(Z)-ethylidene]-7-oxo-1-azabicyclo[3.2.0]hept-2-ene-2-carboxylate (e67) (6.8 mg). νmax 1770, 1700, 1675, 1640, 1620 cm$^{-1}$. δ($CDCl_3$+$D_2O$) 1.11[9H,s,C($CH_3$)$_3$], 1.85 (3H,s,$CH_3$CO), 2.05 (3H,d,J approx. 7 Hz, $CH_3$CH), 3.7-3.3 (2H,m, 4—$CH_2$), 4.4-4.7 (1H,m, 5—$CH$), 5.65 (1H,d,J 14 Hz, $SCH$=CH), 5.83 (1H, broadened q, J ca 7 Hz, $CH_3CH$), 7.00 (1H,d,J 14 Hz $CH$NH), 7.2-7.8 (10H,m,Ar—H).

Method 2

The mesylate (e66) (150 mg) was prepared from the hydroxy compound (290 mg) as described in Example 46 and was converted to the ethylidene compound as in Method I. Chromatography on silica gel (8 g 230-400 mesh ASTM) using gradient elution from 50% ethyl acetate/cyclohexane to neat ethyl acetate gave the ethylidene compound (e67) (21 mg).

EXAMPLE 48

Tert-Butyldiphenylsilyl (5R,6R)-3-[(E)-2-acetamidoethenylthio]-6-[sodium (S)-1-sulphonatooxyethyl]-7-oxo-1-azabicyclo[3.2.0]-hept-2-ene-2-carboxylate

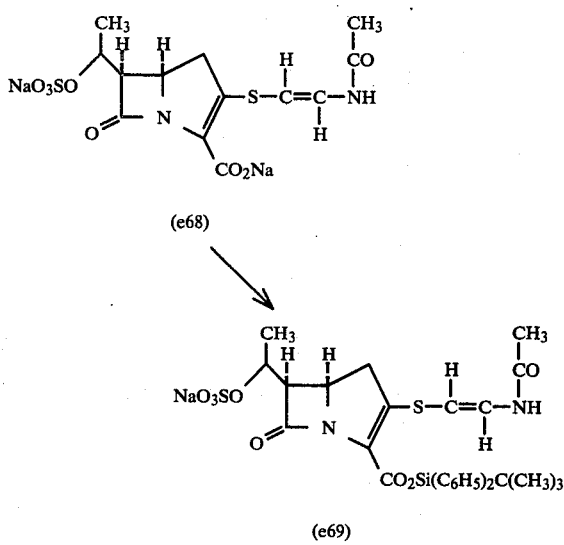

The disodium salt (e68) (200 mg) in N,N-dimethylformamide (DMF) (2 ml) was treated with tert-butylchlorodiphenylsilane (133 mg) in DMF (1 ml). After 30 min, the DMF was evaporated in vacuo and the residue was loaded onto a silica gel column (18 g) and eluted with CHCl₃/C₂H₅OH (3:2). Relevant fractions were combined and evaporated in vacuo, toluene was added to the residue and evaporated to leave tert-butyldiphenylsilyl (5R, 6R)-3-[(E)-2-acetamidoethenylthio]-6-[sodium (S)-1-sulphonatoxyethyl]-7-oxo-1-azabicyclo[3.2.0]-hept-2-ene-2-carboxylate (e69) as a solid (40 mg). $\nu$max (KBr) 1770, 1670, 1520 cm$^{-1}$. $\lambda$max (EtOH) 328 (13,200), 218 (26,000) nm.

EXAMPLE 49

The sodium salt of (5R,6R)-3-[(E)-2-acetamidoethenylthio]-6-[(1S)-1-hydroxysulphonyloxyethyl]-2-p-methoxycarbonylbenzyloxy-carbonyl-7-oxo-1-azabicyclo-[3.2.0]hept-2-ene

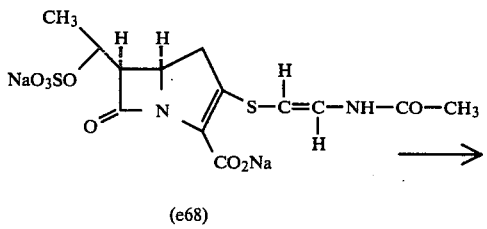

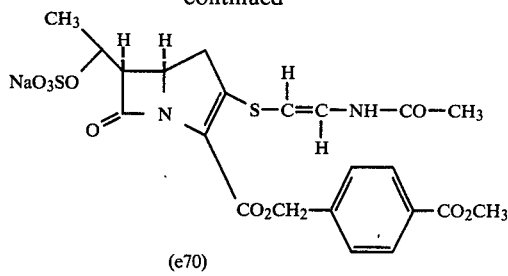

The disodium salt (e68) (3.50 g) in N,N-dimethylformamide (DMF) (30 ml) was treated with methyl 4-bromomethylbenzoate (5.5 g; 3 eq.). After 2½ hr the DMF was removed in vacuo and the residue suspended in chloroform (100 ml) and loaded onto a silica gel column (90 g). The column was then eluted with chloroform/ethanol mixtures; 65:35 (400 ml); 60:40 (400 ml) and finally 40:60. Fractions containing the ester were combined and the solvents removed in vacuo to give the sodium salt of (5R, 6R)-3-[(E)-2-acetamidoethenyl-thio]-6-[(1S)-1-hydroxysulphonyloxyethyl]-2-p-methoxycarbonylbenzyloxycarbonyl-7-oxo-1-azabicyclo-[3.2.0]hept-2-ene (e70) (2.5 g); $\nu$max (KBr) 1770, 1715–1690, 1620, 1280 cm$^{-1}$. The ultraviolet absorption spectrum showed maxima at 323 and 233 nm.

EXAMPLE 50 p-Methoxycarbonylbenzyl-3-[(E)-2-acetamidoethenyl-thio]-6-(EZ)ethylidene-7-oxo-1-azabicyclo[3.2.0]hept-2-ene-2-carboxylate

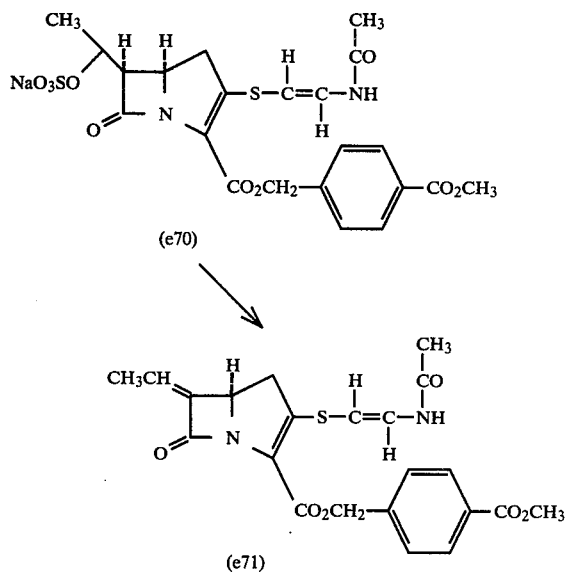

Method I

The sodium salt of (5R,6R)-3-[(E)-2-acetamidoethenylthio]-6-[(1S)-1-hydroxysulphonyloxyethyl]-2-p-methoxycarbonylbenzyloxycarbonyl-7-oxo-1-azabicyclo[3.2.0]hept-2-ene (e70) (340 mg) in DMF (6 ml) and THF (6 ml) was cooled to about 4$^c$ (ice bath), 3 Å molecular sieves (about 300 mg) were added and the mixture was stirred for 15 min. Potassium hydride 24% dispersion in oil, 109 mg) in suspension in THF (2 ml) was added and the mixture stirred for a further 12 mins.

Ethyl acetate and dilute brine were added and the layers were separated. The ethyl acetate layer was washed with water (3×) and then with brine, and then dried (MgSO₄) and evaporated in vacuo. The residue was chromatographed on silica gel (18 g) eluting with dichloromethane (10 ml) then with ethyl acetate (100 ml) and then with ethyl acetate containing 4% of ethanol to give p-methoxycarbonylbenzyl 3-[(E)-2-acetamidoethenylthio]-6-(E,Z)ethylidene-7-oxo-1-azabicyclo[3.2.0-]hept-2-ene-2-carboxylate. (e71) (17 mg), λmax (EtOH) 310 (12,900) 231 (36,800) nm. νmax(CH₂Cl₂) 1765, 1715, 1700, 1620 cm⁻¹. (M⁺ m/e 442.1185; C₂₂H₂₂N₂O₆S requires m/e 442.1196). The n.m.r. spectrum indicated that the product was a mixture of E and Z ethylidene isomers.

Method 2

The ester (e70) (560 mg) in dry DMF (10 ml) and dry THF (10 ml) was cooled (icebath) and stirred with 3 A molecular sieves. The cooled mixture was then treated with sodium hydride (38 mg, 50% dispersion in oil) suspended in dry THF (2 ml). The mixture was stirred in the cold for 1 hr. and then at room temperature for 2.75 hr. Ethyl acetate (about 150 ml) and saturated brine (50 ml) and water (50 ml) were added and the mixture was worked up by a similar route to that in method I to give the ethylidene derivative (e71) (71 mg).

Method 3

The ester (e70) (100 mg) in water (10 ml) was treated with one equivalent of benzyldimethyl-n-hexadecylammonium chloride in dichloromethane (10 ml). After shaking, the CH₂Cl₂ layer was separated and dried (MgSO₄) and evaporated to dryness to give the monoquaternary ammonium salt of the ester. This was taken up in dichloromethane (4 ml) and treated with tetramethylguanidine in CH₂Cl₂ (0.2 ml, 100 mg/ml solution). The mixture was stirred in the cold (icebath) for 15 min and then at r.t. After 2.5 hr, a further aliquot of the tetramethylguanidine solution (0.2 ml) was added and stirring was continued for a further 1 hr. The reaction mixture was worked up by washing with water, drying the CH₂Cl₂ solution (MgSO₄), evaporation and chromatography as in method I to give the ethylidene compound (e71) (18 mg).

Method 4

The ester (e70) (500 mg) in DMF (7 ml) was warmed to 70° C. in the presence of powdered K₂CO₃ (750 mg). After 4 hr., t.l.c. indicated that the reduction had proceeded almost to completion. Ethyl acetate (50 ml) and water (20 ml) were added, and after separation, the aqueous layer was re-extracted with ethyl acetate. The ethyl acetate layers were combined, washed with water (3×20 ml) brine (10 ml), dried (MgSO₄) and evaporated. The residue was chromatographed on silica gel in a similar way to that described in Method I to give the ethylidene compound (e71) (67 mg).

EXAMPLE 51 p-Methoxycarbonylbenzyl (5R,6S)-3-[(E)-2-acetamidoethenylthio]-6-ethyl-7-oxo-1-azabicyclo[3.2.0]hept-2-ene-2-carboxylate

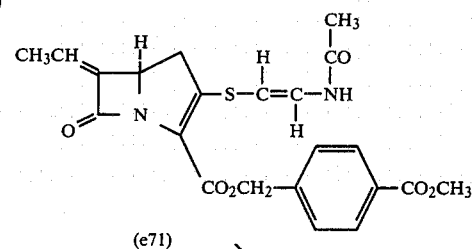

(e71)

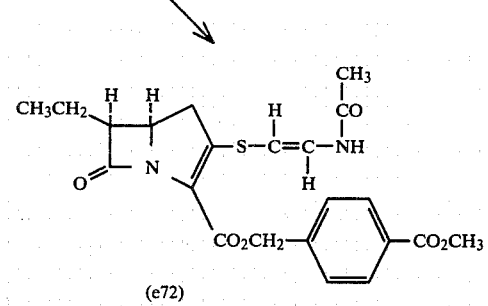

(e72)

p-Methoxycarbonylbenzyl (5R,)-3-[(E)-2-actamidoethenylthio]-6-(EZ)ethylidene-7-oxo-1-azabicyclo[3.2.0-]hept-2-ene carboxylate (e71) (107 mg) in ethyl acetate (25 ml) was hydrogenated at atmospheric pressure over PtO₂(150 mg) for 3 hr. More PtO₂(60 mg) was then added and hydrogenation continued for a further 18 hr. The catalyst was filtered off, the ethyl acetate was evaporated and the residue was chromatographed on silica gel (6 g) eluting with ethyl acetate to give p-Methoxycarbonylbenzyl (5R, 6S)-3-[(E)-2-acetamidoethenylthio]-6-ethyl-7-oxo-1-azabicyclo[3.2.0]hept-2-ene-2-carboxylate (e72) (13.8 mg). νmax (CH₂Cl₂)1787, 1720, 1710(sh), 1625 cm⁻¹. δ(CDCl₃) 0.98 (3H,t,J 7 Hz, CH₃CH₂), 1.5–1.9 (2H,m,CH₃CH₂CH), 2.03 (3H,s,CH₃CO), 2.90 (2H,d,J 9 Hz, 4—CH₂), 3.4–3.7 (1H,m,6—CH), 3.87 (3H,s,CH₃O), 4.0–4.4 (1H,d t,J 6 and 9 Hz, 5—CH), 5.20 and 5.40 (2H, ABq., J 16 Hz, CO₂CH₂), 5.88 (1H,d,J 15 Hz, S.CH═CH), 7.21 (1H,dd,J 15 and 10 Hz, CH═CH.NH), 7.49 and 8.00 (each 2H,d, J 8 Hz, C₆H₄), 7.86 (1H, broad d, J 10 Hz, CH.NH). The U.V. spectrum showed peaks at 325 and 236 nm. The n.m.r. spectrum indicated that a trace of the 5R,6R isomer was also present.

EXAMPLE 52

Sodium (5R,6S)-3-[(E)-2-acetamidoethenylthio]-6-ethyl-7-oxo-1-azabicyclo[3.2.0]hept-2-ene-2-carboxylate

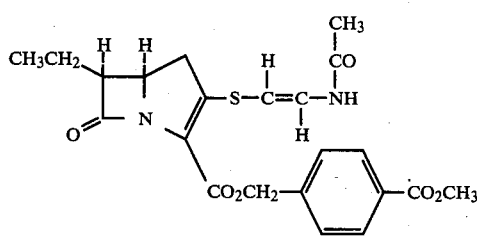

(e72)

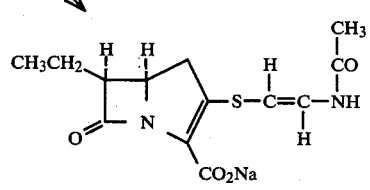

(e73)

p-Methoxycarbonylbenzyl (5R,6S)-3-[(E)-2-acetamido-ethenylthio]-6-ethyl-7-oxo-1-azabicyclo[3.2.0]hept-2-ene-2-carboxylate (e72) (64 mg) in solution in 0.1 M (n-$C_4H_9$)$_4$NBF$_4$ in dry DMF was added to the cathodic compartment of a divided cylindrical electrochemical cell, with a mercury cathode and platinum anode. The volume of electrolyte in the cathodic compartment was about 25 ml, and in the anodic compartment about 10 ml. Acetic acid (12 mg) was added to the cathodic compartment and ethanol (250 mg) was added to the anodic compartment. The cell was degassed by passing argon for 30 min. The potentiostat was engaged to maintain the potential of the cathode at $-1.9$ V w.r.t. standard calomel electrode. The initial current (40 mA) fell to about 5 mA after 25 min. The solvent was removed from the catholyte by evaporation in vacuo and the residual oil was taken up in $CH_2Cl_2$ (20 ml) and extracted with water (15 ml) containing sodium tetrafluoroborate (100 mg). The aqueous extract was washed with $CH_2Cl_2$ and then passed down an Amberlite 1R 120 column (1×20 cm) in the sodium form. The volume of the eluate was reduced to about 5 ml by evaporation in vacuo and loaded onto a Biogel P-2 column (18×3 cm). Elution with water yielded fractions containing sodium (5R,6S)-3-[(E)-2-acetamidoethenylthio]-6-ethyl-7-oxo-1-azabicyclo[3.2.0]hept-2-ene-2-carboxylate (e73) $\lambda_{max}$ 308 nm. The minimum inhibitory concentrations (MIC) of this compound was determined using a standard DST agar+10% horse blood substrate.

The results are shown below.

| ORGANISM | MIC (μg/ml) |
|---|---|
| *Citrobacter freundii* E8 | 2.5 |
| *Enterobactor cloacae* N1 | 2.5 |
| *Escherichia coli* 0111 | 2.5 |
| *Escherichia coli* JT 39 | 10 |
| *Klebsiella aerogenes* A | 2.5 |
| *Proteus mirabilis* C977 | 10 |
| *Proteus morganii* I580 | 5.0 |
| *Proteus rettgeri* WM16 | 10 |
| *Proteus vulgaris* W091 | 10 |
| *Pseudomonas aeruginosa* A | >40 |
| *Salmonella typhimurium* CT10 | 1.2 |
| *Serratia marcescens* US20 | 5.0 |
| *Shigella sonnei* MB 11967 | 2.5 |
| *Bacillus subtilis* A | 1.2 |
| *Staphylococcus aureus* Oxford | 0.6 |
| *Staphylococcus aureus* Russell | 2.5 |
| *Staphylococcus aureus* 1517 | >40 |
| *Streptococcus faecalis* I | 40 |
| *Streptococcus pneumoniae* CN33 | ≦0.1 |
| *Streptococcus pyogenes* CN10 | NG |
| *E. coli* ESS | 0.3 |

EXAMPLE 53

Cleavage of the tert-Butyldiphenylsilyl Ester Grouping

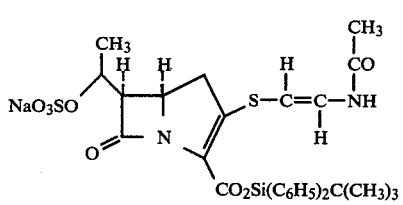

(e69)

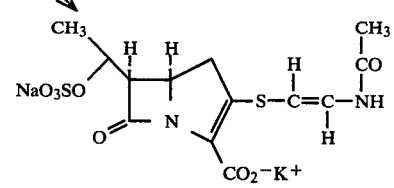

(e74)

Method I tert-Butyldiphenylsilyl (5R,6R)-3-[(E)-2-acetamidoethenylthio]-6-[sodium (S)-1-sulphonatooxyethyl]-7-oxo-1-azabicyclo[3.2.0]-hept-2-ene-2-carboxylate (e69) (17.8 mg) in N,N-dimethylformamide (0.5 ml) was treated with a few crystals of 18-crown-6 crown ether, followed by anhydrous potassium fluoride (3 mg). After 5 hr. the solvent was removed in vacuo and ethyl acetate (2 ml) and water (2 ml) were added to the residue. After partitioning, the aqueous layer was loaded onto Biogel P-2 (13×2.3 cm column) and eluted with deionised water, the pH of which had been adjusted to 7 by addition of very dilute NaHCO$_3$ solution. Fractions containing the salt were combined and evaporated in vacuo to low volume, ethanol was added and evaporated in vacuo (3×), then toluene was added and evaporated in vacuo to leave the di-salt (e74) as a solid (3 mg).

Method 2

The ester (e69) was dissolved in water. H.p.l.c. of the solution [Waters $C_{18}$ Microbondapack column eluting with aqueous NH$_4$H$_2$PO$_4$ (5.75 g/l) with 5% CH$_3$CN, pH adjusted to 6.8 with NH$_4$OH] demonstrated that hydrolysis of the ester had occurred.

EXAMPLE 54 p-Nitrobenzyl
(5R,6E)-3-(2-acetamidoethylthio)-6-ethylidene-7-oxo-1-azabicyclo[3.2.0]hept-2-ene-2-carboxylate and
p-Nitrobenzyl
(5R,6Z)-3-(2-acetamidoethylthio)-6-ethylidene-7-oxo-1-azabicyclo[3.2.0]hept-2-ene-2-carboxylate

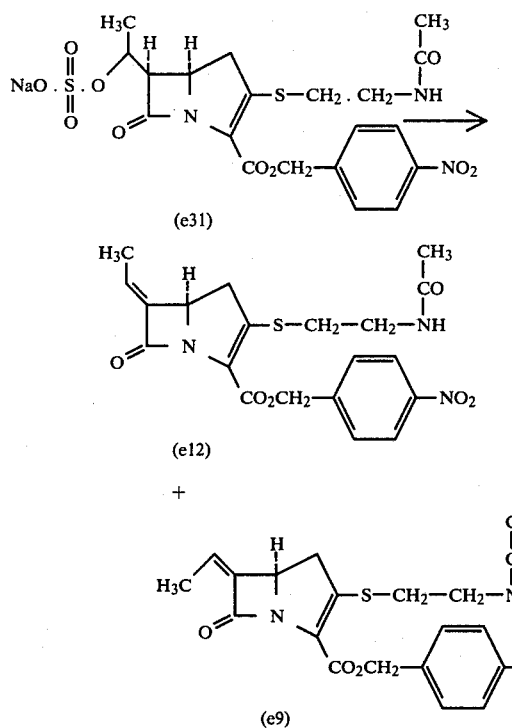

A solution of the mono-ester, mono-salt (e31) (0.8 g of 80% pure material) in water (50 ml) was shaken with a solution of cetylbenzyldimethyl-ammonium chloride (0.46 g) in chloroform (50 ml). The aqueous layer was re-extracted with chloroform (10 ml) and the combined organic phases were dried (MgSO₄) and evaporated in vacuo.

The resulting quaternary ammonium salt was dissolved in dichloromethane (50 ml) and the solution was cooled to −30°. 1,5-Diazabicyclo[5.4.0]undec-5-ene (DBU) (0.25 g) was added to the solution which was then kept at 0° for 4.5 hr. The solution was then washed with brine and dried (MgSO₄). Evaporation of the solution in vacuo afforded a gum which was chromatographed on silica gel, using ethyl acetate followed by 20% ethanol in ethyl acetate to elute, to afford a mixture of E- and Z-ethylidene derivatives (e12) and (e9) (0.103 g) (about 1:1); $\nu_{max}$ (KBr) 1765, 1700, 1655 and 1635 cm$^{-1}$.

EXAMPLE 55 p-Bromobenzyl
(5R,6Z)-3-(2-acetamidoethylthio)-6-ethylidene-7-oxo-1-azabicyclo[3.2.0]hept-2-ene-2-carboxylate and
p-bromobenzyl
(5R,6E)-3-(2-acetamidoethylthio)-6-ethylidene-7-oxo-1-azabicyclo[3.2.0]hept-2-ene-2-carboxylate

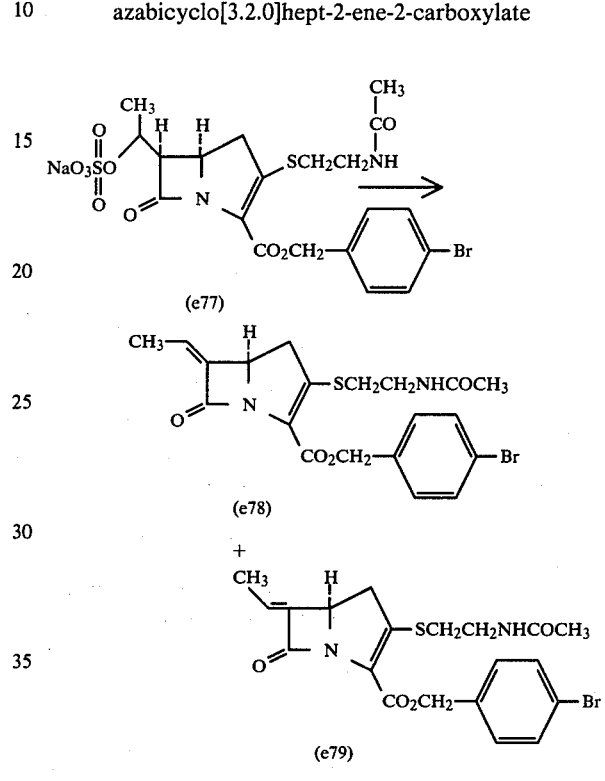

A solution of the mono-ester (e77) (1.15 g, about 60% pure) in water (30 ml) was shaken with a solution of cetylbenzyldimethylammonium chloride (0.39 g) in dichloromethane (30 ml). The organic layer was dried (MgSO₄) and evaporated in vacuo to afford a foam (881 mg).

The product was dissolved in dichloromethane (25 ml) and to the cooled (0°) solution was added DBU (0.202 g). After standing at 0° for 4 h the solution was washed with water and brine, dried (MgSO₄) and concentrated in vacuo. Chromatography of the residue on silica gel using neat CHCl₃ grinding to 10% ethanol in CHCl₃ to elute afforded the title esters (e78 and e79) (81 mg) as a mixture of Z- and E-isomers (ca. 1:1); $\nu_{max}$ (CHCl₃) 3460, 1770, 1700, and 1670 cm$^{-1}$; δ(CDCl₃) 1.81 and 2.04 (total 3H, each d, J 7 Hz, C$\underline{H}$₃CH for E- and Z-isomers respectively), 1.94 (3H, s, C$\underline{H}$₃CO), 2.80–3.55 (6H, m, NC$\underline{H}$₂C$\underline{H}$₂S and 4-C$\underline{H}$₂), 4.70 (1H, m, 5-C$\underline{H}$), 5.12 and 5.33 (each 1H, d, J 13 Hz, CO₂CH₂), 5.95 (approx. 0.5H, br q, J 7 Hz, CH₃C$\underline{H}$ for Z-isomer), ca. 6.25 (1H, br, NH), 6.40 (approx. 0.5H, q d, J 7 and 1 Hz, CH₃C$\underline{H}$ for E-isomer) and 7.25–7.55 (4H, m, C₆$\underline{H}$₄).

EXAMPLE 56

Phthalidyl
(5R)-3-[(E)-2-acetamidoethenylthio]-6-(Z)-ethylidene-7-oxo-1-azabicyclo[3.2.0]hept-2-ene-2-carboxylate

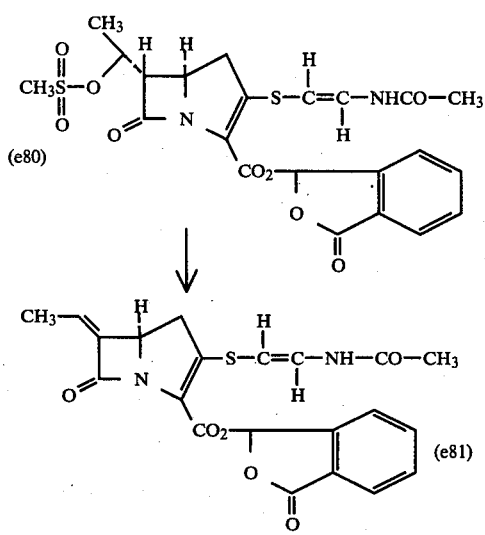

A solution of the mesylate (e80) (350 mg) in DMF (5 ml) was stirred vigorously with anhydrous $K_2CO_3$ (277 mg) for 1 h. The mixture was filtered and the filtrate was evaporated in vacuo. The residue was chromatographed on silica gel using a gradient elution of $CHCl_3$ to 10% ethanol in $CHCl_3$ to elute. The ethylidene phthalidyl ester (e81) was obtained as a pale yellow solid (110 mg); $\lambda_{max}$ (EtOH) 336, 272 and 229 nm; $\nu_{max}$ (Kbr) 1760–1785 (br), 1700 and 1620 cm$^{-1}$; $\delta[(CD_3)_2SO]$ approx. 1.95 (6H, br, C$\underline{H}_3$CH and C$\underline{H}_3$CO), approx. 3.1 (2H, m, 4-C$\underline{H}_2$), 4.66 (1H, br t, J 9 Hz, 5-C$\underline{H}$), 5.86 (1H, d, J 14 Hz, =C$\underline{H}$S), 6.10 (1H, br q, J 7 Hz, $CH_3C\underline{H}$:), approx. 6.85–7.25 (1H, m, =C$\underline{H}$N), approx. 7.57–8.00 (5H, m, phthalidyl protons).

EXAMPLE 57

Benzyl
(5R)-3-[(E)-2-acetamidoethenylthio]-6-(Z)-ethylidene-7-oxo-1-azabicyclo[3.2.0]hept-2-ene-2-carboxylate

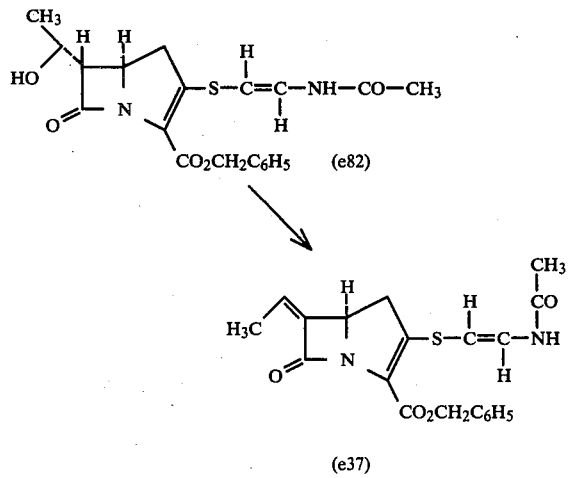

The ester (e82) (50 mg) was dissolved in THF (3 ml) and triphenylphosphine (Ph$_3$P) (49 mg) was added. The solution was cooled to 0° and diethylazodicarboxylate (DEAD) (32 mg) was added with stirring. The solution was allowed to warm to room temperature and stirring was continued for 1 h after which more $(C_6H_5)_3P$ (50 mg) and DEAD (32 mg) were added. After a further 15 min the solution was evaporated and the residue was partitioned between ethyl acetate and water. The organic layer was washed with brine, then dried (MgSO$_4$) and evaporated in vacuo, and the residue chromatographed on silica gel using a gradient elution of $CHCl_3$ to 10% ethanol in $CHCl_3$.

The (Z)-isomer (e37) was obtained as a foam (28 mg); $\nu_{max}$ (CHCl$_3$) 1765, 1700 and 1625 cm$^{-1}$.

EXAMPLE 58

Benzyl
(5R)-3-[(E)-2-acetamidoethenylthio]-6-ethylidene-7-oxo-1-azabicyclo[3.2.0]hept-2-ene-2-carboxylate

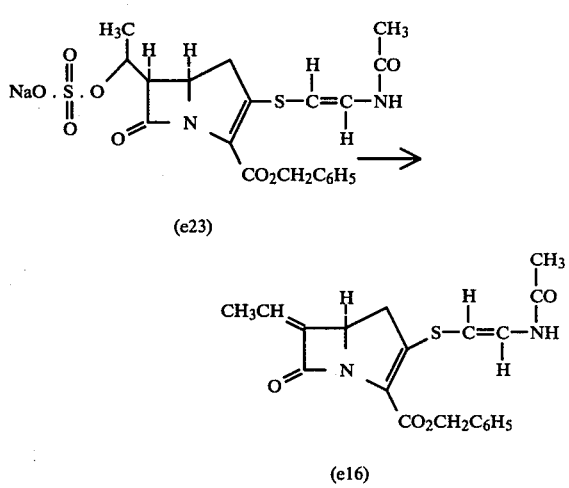

A solution of the benzyl ester (e23) (1.17 g) in water (50 ml) was shaken with a solution of cetylbenzyldimethylammonium chloride (0.9 g) in dichloromethane (50 ml). The organic layer was dried (MgSO$_4$) and evaporated in vacuo to afford the quaternary ammonium salt as a foam (1.8 g).

The salt was dissolved in dichloromethane (40 ml) and the solution was cooled to 0° before adding DBU (0.6 g). After 4 h at 0° the solution was washed with brine. The organic layer was dried (MgSO$_4$) and evaporated in vacuo. Chromatography on silica gel, using a gradient elution from ethylacetate/petroleum ether (4:1) to ethyl acetate, afforded the ethylidene derivative (e16) as a mixture of E- and Z-isomers (0.345 g).

EXAMPLE 59 p-Nitrobenzyl (5R)-3-[(E)-2-acetamidoethenylthio]-6-ethylidene-7-oxo-1-azabicyclo[3.2.0]hept-2-ene-2-carboxylate

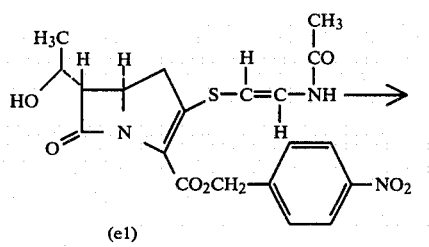
(e1)

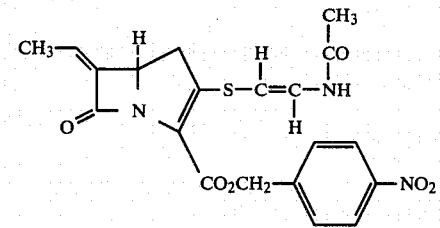
(e3)

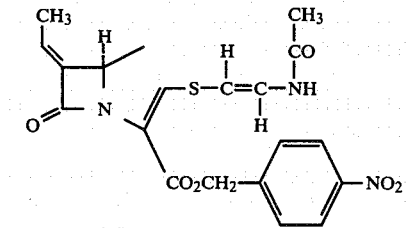
(e6)

To a suspension of the ester (e1) (50 mg) in THF (2 ml) was added tri-n-butylphosphine (45 mg). Diethylazodicarboxylate (39 mg) was added with stirring, and stirring was continued until all the material had gone into solution (5 min). The solution was diluted with ethyl acetate and water and the organic layer was washed with water (×2) and brine. Evaporation of the dried (MgSO4) organic solution afforded a product which was chromatographed on silica gel using a gradient elution of 20% petrol in ethyl acetate to ethyl acetate. The ethylidene derivative was obtained as a mixture of (E)- and (Z)-isomers (e6 and e3) (about 2:3) (31 mg).

EXAMPLE 60 p-Nitrobenzyl (5R)-3-[(E)-2-acetamidoethenylthio]-6-(Z)-ethylidene-7-oxo-1-azabicyclo[3.2.0]hept-2-ene-2-carboxylate

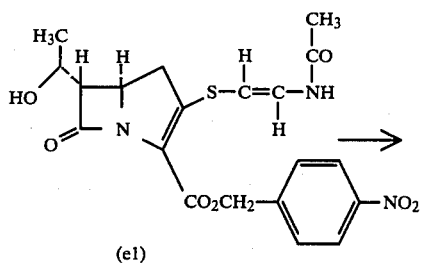
(e1)

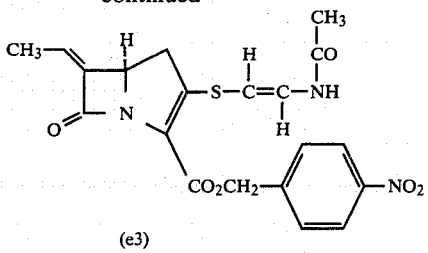
(e3)

To a suspension of the ester (e1) (1 g) in THF (30 ml) was added triphenylphosphine (1.17 g). The mixture was cooled to 0° and to it was added dropwise with stirring a solution of diethylazodicarboxylate (DEAD) (0.78 g) in THF (5 ml). The solution was allowed to warm to room temperature for 30 min, after which it was again cooled to 0° and further quantities of (C6H5)3P (0.3 g) and DEAD (0.2 g) were added. After another 10 min at room temperature the solution was evaporated in vacuo and the residue was partitioned between ethyl acetate (70 ml) and water (50 ml). The organic phase was washed with water (50 ml) and brine (30 ml), then dried (MgSO4) and evaporated in vacuo. The product was chromatographed on silica gel using a gradient elution of 20% petroleum ether in ethyl acetate to 5% ethanol in ethyl acetate. Fractions containing the product were combined and concentrated in vacuo. Crystallisation from ethyl acetate-ether afforded the (Z)-isomer (e3) as a pale yellow solid (0.81 g).

EXAMPLE 61

Sodium (5R,6S)-3-[(E)-2-acetamidoethenylthio]-6-[(S)-1-methyl-sulphonyloxyethyl]-7-oxo-1-azabicyclo[3.2.0]hept-2-carboxylate

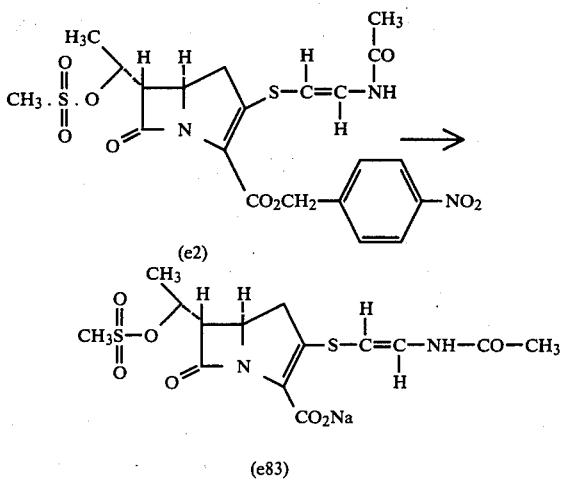
(e83)

A solution of the mesylate (e2) (50 mg) in 40% aqueous dioxan (2 ml) was added to a mixture of 5% Pd on C (75 mg) and 40% aqueous dioxan (5 ml) which had previously been pre-hydrogenated for 0.5 h. Hydrogenation of the mixture was then continued for 3 h at room temperature and atmospheric pressure. The mixture was filtered through Celite and NaHCO3 (9 mg) was added. The solution was concentrated in vacuo, and the aqueous layer washed with ethyl acetate (3×25 ml). The aqueous solution was chromatographed on Biogel P2 using water to elute. The fractions contining a u.v. chromophore at λmax. 305 nm were combined and evaporated down, using ethanol to azeotrope out water and toluene to azeotrope out ethanol, to afford the title salt (e83) as a cream-coloured solid (31 mg); λmax (H$_2$O) 305 and 228 nm; νmax (KBr) 1765, 1670 and 1620 cm$^{-1}$.

EXAMPLE 62

Sodium (5R,6R)-3-[(E)-2-acetamidoethenylthio]-6-[(S)-1-methylsulphonyloxyethyl]-7-oxo-1-azabicyclo[3.2.0-]hept-2-ene-2-carboxylate

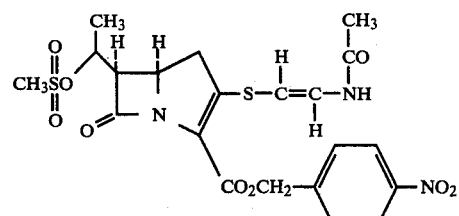

(e5)

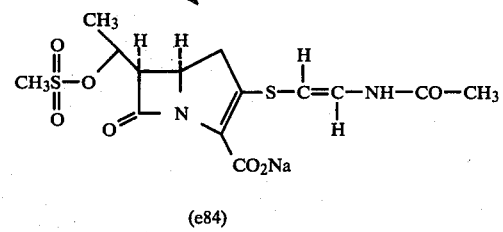

(e84)

The ester (e5) (90 mg) was hydrogenolysed as described in Example 61, using 5% Pd on C (100 mg) and 40% aqueous dioxan (10 ml).

The title salt (e 84) was obtained in aqueous solution after chromatography on Biogel P2. This solution was divided into two equal parts; one of these portions was evaporated in vacuo as in Example 61 to afford the salt (e84) as an amorphous solid (14 mg); λmax (H$_2$O) 306 and 228 nm; νmax (KBr) 1750, 1670 and 1615 nm.

EXAMPLE 63

Phthalidyl (5R,6S)-3-[(E)-2-acetamidoethenylthio]-6-[(S)-1-methylsulphonyloxyethyl]-7-oxo-1-azabicyclo[3.2.0-]hept-2-ene-2-carboxylate

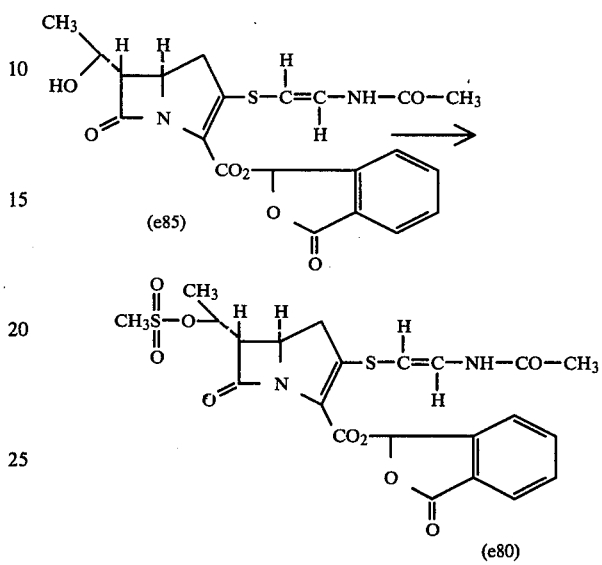

Triethylamine (34 mg) was added to a suspension of the ester (e85) (50 mg) in methylene chloride (2 ml). The mixture was cooled to −5° before adding a solution of mesyl chloride (25.7 mg) in methylene chloride (0.87 ml) dropwise over 2 min. Stirring was continued at −5° until the starting ester had completely dissolved (10 min) and a further quantity (15 ml) of methylene chloride was then added. The organic solution was washed with cold water (20 ml), cold pH3 phosphate buffer (2×15 ml) and cold aqueous NaHCO$_3$ solution (20 ml). It was then dried (MgSO$_4$) and evaporated in vacuo. Trituration of the residue with ether afforded the mesylate (e 80) as a yellow solid (32 mg); λ$_{max}$ (C$_2$H$_5$OH) 332 (12,450) and 230 nm (20,800); ν$_{max}$ (CHCl$_3$) 1785, 1705 and 1625 cm$^{-1}$.

EXAMPLE 64 p-Bromobenzyl (5R,6S)-3-(2-acetamidoethylthio)-6-ethyl-7-oxo-1-azabicyclo[3.2.0]hept-2-ene-2-carboxylate

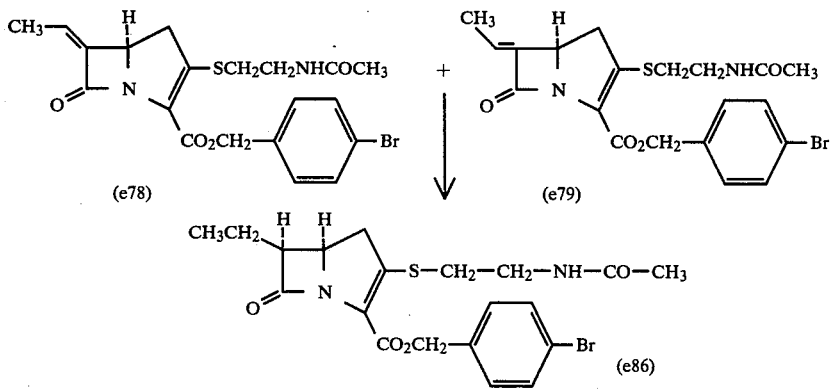

A solution of the Z- and E- ethylidene derivatives (e78 and e79) (80 mg) in ethyl acetate (10 ml) was hydrogenated at atmospheric pressure and room temperature in the presence of platinum oxide catalyst (80 mg) for 23 h. The mixture was filtered through Celite and the solution was concentrated in vacuo. The product was chromatographed on a short silica column using ethyl acetate as eluant. The (5R,6S) derivative (e86) was obtained as a gum (17 mg); $\lambda_{max}$ (EtOH) 316 nm; $\nu_{max}$ (CHCl$_3$) 3460, 1780 and 1700–1670 (br) cm$^{-1}$; $\delta$(CDCl$_3$) 1.03 (3H, t, J 7 Hz, C$\underline{H}_3$CH$_2$), approximately 1.67 (2H, m, C$\underline{H}_2$CH$_3$), 1.97 (3H, s, C$\underline{H}_3$CO), approx. 2.8–3.7 (7H, m, SC$\underline{H}_2$C$\underline{H}_2$N, 4-C$\underline{H}_2$ and 6-C$\underline{H}$), 4.25 (1H, dt, J 6 and 9 Hz, 5-C$\underline{H}$), 5.09 and 5.30 (each 1H, d, J 14 Hz, CO$_2$C$\underline{H}_2$), 5.90 (1H, br, N$\underline{H}$), 7.28 and 7.47 (each 2H, d, J 9 Hz, C$_6\underline{H}_4$). [M$^+$, 466(+468)].

The product contained a trace of the corresponding (5R,6R)-isomer.

EXAMPLE 65 p-Nitrobenzyl (5R,6R)-3-(2-acetamidoethylthio)-6-ethyl-7-oxo-1-azabicyclo[3.2.0]hept-2-ene-2-carboxylate

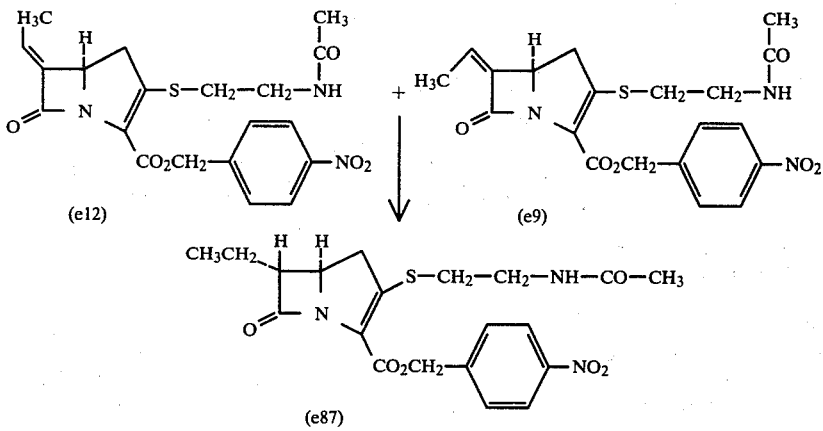

A mixture of E- and Z- ethylidene derivatives (e12 and e9) (200 mg) were suspended in THF (10 ml) and water (ca.1 ml) was added until a solution was formed. The solution was cooled in an ice-salt bath and solid NaBH$_4$ (70 mg) was added with stirring. After 30 min, ethyl acetate (50 ml) was added and the solution was washed with water and brine, before drying (MgSO$_4$) and evaporating the solvent in vacuo.

The product was chromatographed on silica gel, using a gradient elution from ethyl acetate to 10% ethanol in ethyl acetate, to afford the title compound (e87) as a yellow solid (60 mg); $\lambda$max (EtOH) 317 (12,300) and 266 nm (11,200); $\nu_{max}$(KBr) 1790 sh, 1780, 1700 sh, 1695 and 1630 cm$^{-1}$; (CHCl$_3$) 1775, 1700 and 1670 cm$^{-1}$; $\delta$[(CD$_3$)$_2$ NCDO]1.02 (3H, t, J 7 Hz, C$\underline{H}_3$CH$_2$) ca. 1.63–2.00 (2H, m, C$\underline{H}_2$CH$_3$), 1.88 (3H, s, C$\underline{H}_3$CO), ca. 3.0–3.6 (7H, m, SC$\underline{H}_2$C$\underline{H}_2$N, 4-C$\underline{H}_2$ and 6-C$\underline{H}$), 4.03 (1H, dt, J 2.5 and 8.5 Hz, 5-C$\underline{H}$), 5.32 and 5.57 (each 1H, d, J 14 Hz, CO$_2$C$\underline{H}_2$), 7.82 and 8.27 (each 2H, d, J 9 Hz, C$_6\underline{H}_4$) 8.10 (1H, br, N$\underline{H}$) [M$^+$, 433.1312. C$_{20}$H$_{23}$N$_3$O$_6$S requires M, 433.1305].

The product contained a trace of the corresponding (5R,6S)-isomer.

EXAMPLE 66

Sodium (5R,6R)-3-(2-acetamidoethylthio)-6-ethyl-7-oxo-1-azabicyclo[3.2.0]hept-2-ene-2-carboxylate

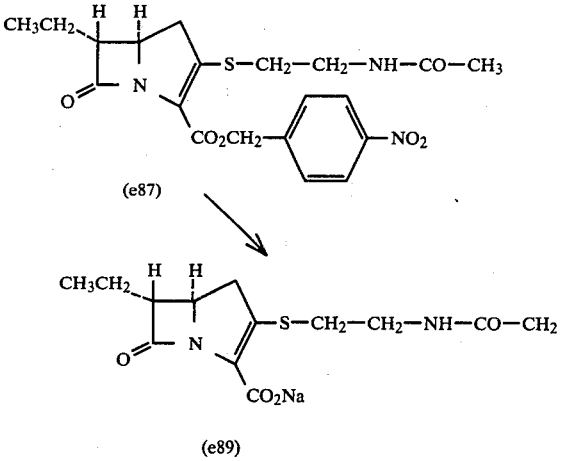

The ester (e87) (65 mg) was dissolved in 20% aqueous dioxan (2 ml) and the solution was added to a mixture of 5% Pd on C (80 mg) in aqueous dioxan (8 ml) which had been prehydrogenated for 0.5 h. Hydrogenation was continued for 2 h at atmospheric pressure and room temperature before adding a further quantity of catalyst (30 mg) and hydrogenating for 1 h more. A solution of NaHCO$_3$ (5 mg) in water (2 ml) was then added and the mixture was filtered through Celite, washing well with water. The solution was concentrated in vacuo to about 10 ml and was then washed with ethyl acetate (3×50 ml). The aqueous layer was concentrated in vacuo to about 5 ml and then loaded onto a column (15×2.5 cm) of Biogel P2. Elution with deionised water gave several fractions containing the title salt (e89) detected by u.v.; $\lambda_{max}$ (H$_2$O) 299 nm.

EXAMPLE 67 p-Nitrobenzyl
(5R,6R)-3-[(E)-2-acetamidoethenylthio]-6-(1-methoxycarbonylmethylthioethyl)-7-oxo-1-azabicyclo[3.2.0-]hept-2-ene-2-carboxylate

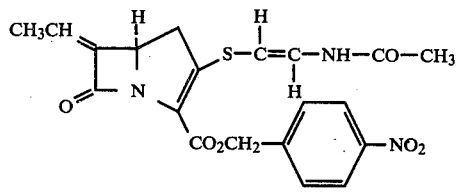

(e88) ⟶

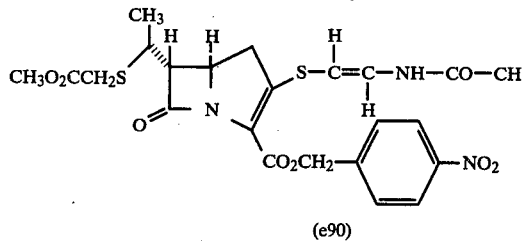

(e90)

A solution of the ethylidene derivative (e88) (180 mg) in DMF (5 ml) was cooled to −30° C. Anhydrous K$_2$CO$_3$ (29 mg) was added with vigorous stirring followed by methyl 2-mercaptoacetate (42 mg). After stirring for 15 min at −30° C. the solution was diluted with ethyl acetate (30 ml) and the organic solution was washed with water (×3) and brine. Evaporation of the dried (MgSO$_4$) organic solution afforded a gum which was chromatographed on a column of silica gel, employing a gradient elution of petroleum ether/ethyl acetate (2:3) to ethyl acetate. After discarding several fractions containing non-β-lactam products, other fractions containing impure thioether (e 90) were combined and concentrated in vacuo. The crude product was re-chromatographed using the same solvent system to afford substantially pure thioether (e 90) (19 mg) as a mixture of diastereoisomers; λ$_{max}$ (EtOH) 325 nm; ν$_{max}$ (CHCl$_3$) 1780, 1730, 1700 and 1625 cm$^{-1}$ δ(CDCl$_3$) approx 1.30–1.60 (3H, m, C$\underline{H}_3$CH), 2.09 (3H, s, C$\underline{H}_3$CO), approx 2.85–3.55 (6H, m, 4-C$\underline{H}_2$, 6-C$\underline{H}$, C$\underline{H}$SC$\underline{H}_2$), 3.75 (3H, s, C$\underline{H}_3$O$_2$C), 4.12 (1H, m, 5-C$\underline{H}$), 5.35 (2H, centre of AB, CO$_2$C$\underline{H}_2$), 5.86 (1H, d, J 13.5 Hz, =CHS), 7.22 (1H, m, =C$\underline{H}$N), approx 7.5 (1H, N$\underline{H}$), 7.63 and 8.22 (each 2H, d, J 8.5 Hz, aromatic protons).

EXAMPLE 68

Benzyl
(5R,6R)-3-[(E)-2-acetamidoethenylthio]-6-[(R)-1-phenylthioethyl]-7-oxo-1-azabicyclo[3.2.0]hept-2-ene-2-carboxylate

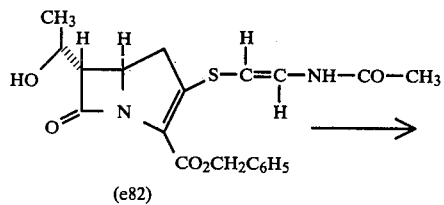

(e82)

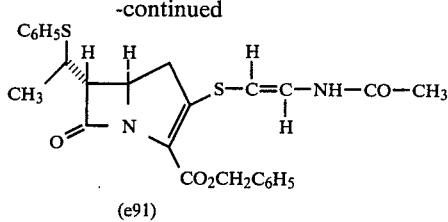

(e91)

Phenylthiosuccinimide (31 mg) and tri-n-butylphosphine (30 mg) were dissolved in THF (3 ml). After stirring for 5 min at r.t. the alcohol (e 82) (50 mg) was added in one portion. After stirring for 4 hr at room temperature the solution was diluted with ethyl acetate (25 ml) and washed with water and brine. Evaporation of the dried (MgSO$_4$) solution gave a residue which was chromatographed on silica gel using a gradient elution of petroleum ether/ethyl acetate (1:1 to 3:7). The title compound (e 91) was obtained as a gum (8 mg); λ$_{max}$ (EtOH) 325 nm; ν$_{max}$ (CHCl$_3$) 1775, 1700 and 1620 cm$^{-1}$. δ(CDCl$_3$) 1.44 (3H, d, J 6.5 Hz, C$\underline{H}_3$CH), 2.06 (3H, s, CH$_3$CO), 2.85–3.20 (3H, m, 4-C$\underline{H}_2$ and 6-C$\underline{H}$), approx. 3.4 (1H, m, CH$_3$C$\underline{H}$), 3.93 (1H, dt, J 3 and 9 Hz, 5-C$\underline{H}$), 5.24 (2H, centre of AB, wings at 5.07 and 5.40, CO$_2$C$\underline{H}_2$), 5.82 (1H, d, J 13.5 Hz, SC$\underline{H}$=) and 7.0–7.5 (12H, m, C$_6$$\underline{H}_5$CH$_2$, C$_6$$\underline{H}_5$S, =C$\underline{H}$.N$\underline{H}$).

EXAMPLE 69 p-Nitrobenzyl
(5R,6R)-3-(2-acetamidoethylthio)-6-(1-ethylthioethyl)-7-oxo-1-azabicyclo[3.2.0]hept-2-ene-2-carboxylate

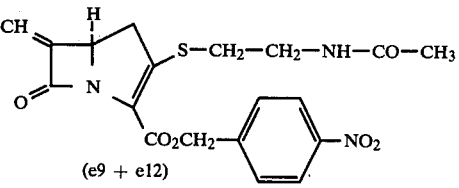

(e9 + e12)

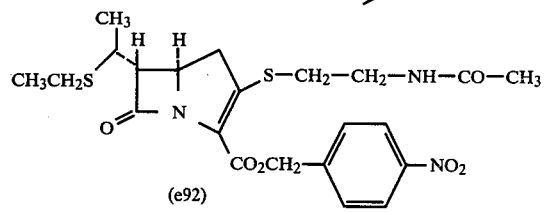

(e92)

A solution of the ethylidene derivatives (e 9+e 12 ) (200 mg) in DMF (4 ml) was cooled to −30° C. and anhydrous K$_2$CO$_3$ (32 mg) was added. To the vigorously stirred mixture was added ethanethiol (26 mg), and stirring at −30° C. was continued for 1 hr. Ethyl acetate (30 ml) was added and the organic solution was washed with water (×4) and brine, then dried (MgSO$_4$) and evaporated in vacuo. The residue was chromatographed on silica gel using a gradient elution of ethyl acetate/petroleum ether (7:3) to ethanol/ethyl acetate (5:95). The title compound (e 92) was obtained as a foam (58 mg); λ$_{max}$ (EtOH) 320 and 267 nm; ν$_{max}$ (CHCl$_3$) 1775, 1770 and 1670 cm$^{-1}$; δ(CDCl$_3$) 1.26 (3H, t, J 7.5 Hz, CH$_3$CH$_2$), ca 1.25–1.50 (3H, m, C$\underline{H}_3$CH), 1.97 (3H, s, C$\underline{H}_3$CO), 2.59 (2H, q, J 7.5 Hz, SC$\underline{H}_2$CH$_3$), 2.85–3.6 (8H, m, 4-C$\underline{H}_2$, NC$\underline{H}_2$C$\underline{H}_2$S, 6-C$\underline{H}$, and CH$_3$C$\underline{H}$), 4.15

(br t, J approx 8 Hz, 5-C$\underline{H}$), 5.20 and 5.49 (each 1H, d, J 14 Hz, CO$_2$CH$_2$), 6.05 (1H, br, N$\underline{H}$), 7.63 and 8.15 (each 2H, d, J 9 Hz, C$_6$$\underline{H}$$_4$).

EXAMPLE 70 p-Nitrobenzyl (5R,6R)-3-[(E)-2-actamidoethenylthio]-6-(1-benzylthioethyl)-7-oxo-1-azabicyclo[3.2.0]hept-2-ene-2-carboxylate

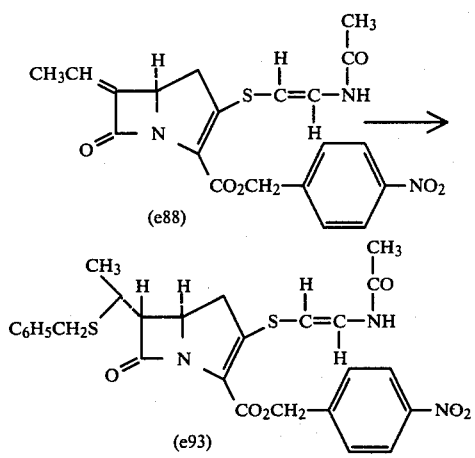

The ethylidene derivative (e88) (320 mg) was dissolved in DMF and the solution was cooled to −25°. Anhydrous K$_2$CO$_3$ (52 mg) was added followed by benzyl mercaptan (83 mg) with vigorous stirring. Stirring was continued at −20° for 25 min and the solution was then diluted with ethyl acetate (35 ml) and washed with water, aqueous NaHCO$_3$ solution, more water (×2) and brine. Evaporation of the dried (MgSO$_4$) organic solution gave a residue which was chromatographed on silica gel using a gradient elution of petroleum ether/ethyl acetate (3:2) to ethyl acetate. Early fractions containing the title thioether (e93) were evaporated in vacuo and the residue was crystallised from ethyl acetate/ether to afford a single isomer of the thioether (e93) (45 mg); λ$_{max}$(EtOH) 327 (13,200) and 261 nm (13,800); ν$_{max}$ (KBr) 1775, 1700, 1685 and 1620 cm$^{-1}$; δ[(CD$_3$)$_2$NCDO]1.40 (3H, d, J 7 Hz, C$\underline{H}$$_3$CH), 3.15 (2H, d, J 9 Hz, 4-C$\underline{H}$$_2$), approx. 3.15 (1H, m, CH$_3$C$\underline{H}$S), 3.52 (1H, dd, J 3 and 9 Hz, 6-C$\underline{H}$), 3.89 (2H, s, C$\underline{H}$$_2$S), 4.05 (1H, dt, J 3 and 9 Hz, 5-C$\underline{H}$), 5.32 and 5.56 [each 1H, d, J 14 Hz, CO$_2$C$\underline{H}$$_2$], 5.97 (1H, d, J 13.5 Hz, =C$\underline{H}$.S), 7.05–7.55 (6H, m, C$_6$$\underline{H}$$_5$ and =C$\underline{H}$.N), 7.79 and 8.24 [each 2H, d, J 9 Hz, C$_6$$\underline{H}$$_4$] and 11.2 (1H, brd, J 11 Hz, NH). [M+, 553.1297. C$_{27}$H$_{27}$N$_3$O$_6$S$_2$ requires M, 553.1339].

Intermediate fractions containing the product were combined and evaporated to afford a mixture of the two diastereoisomers of compound (e93) (approx. 1:1) (42 mg) and later fractions afforded a mixture (approx. 2:3) (37 mg) that was enriched in the more polar isomer of the title compound; ν$_{max}$. (CHCl$_3$) 1778, 1700 and 1625 cm$^{-1}$; δ[(CD$_3$)$_2$NCDO] as described for the least polar isomer except for extra signals at 1.29 (d, J 7 Hz, C$\underline{H}$$_3$CH), 3.76 (dd, J3 and 6 Hz, 6-C$\underline{H}$) and approx 4.15 (m, 5-C$\underline{H}$).

EXAMPLE 71

Sodium (5R,6R)-3-[(E)-2-acetamidoethenylthio]-6-(1-benzylthioethyl)-7-oxo-1-azabicyclo[3.2.0]hept-2-ene-2-carboxylate

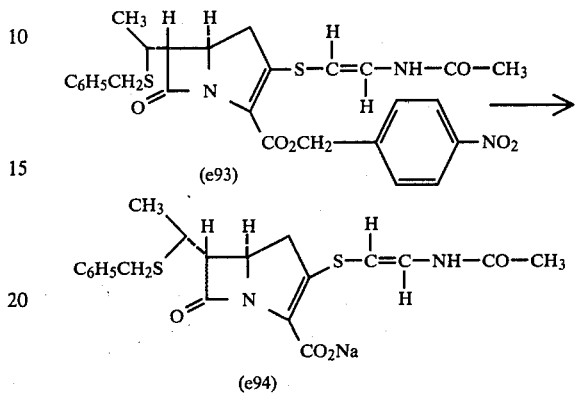

The least polar crystalline isomer of the ester (e93) (40 mg) obtained in Example 70 was added to a mixture of 5% Pd on C (60 mg) in 20% aqueous dioxan (5 ml) which had been prehydrogenated for 0.5 h. Hydrogenation was continued for 4 h and the mixture was filtered through Celite after adding NaHCO$_3$ (7 mg) and water (10 ml). The solution was concentrated to a volume of about 10 ml and was then washed with ethyl acetate (3×30 ml). The aqueous solution was concentrated to about 5 ml and then loaded onto a column (10×2.5 cm) of Biogel P2. Elution with water afforded fractions containing the title sodium salt (e94) as identified by the characteristic u.v. chromophore; λ$_{max}$. (H$_2$O) 309 nm. The minimum inhibitory concentratitons (MIC) of this compound was determined using a standard DST agar+10% horse blood substrate.

The results are shown below.

| ORGANISM | MIC (μg/ml) |
|---|---|
| Citrobacter freundii E8 | 6.2 |
| Enterobactor cloacae N1 | 3.1 |
| Escherichia coli 0111 | 3.1 |
| Escherichia coli JT 39 | 3.1 |
| Klebsiella aerogenes A | 3.1 |
| Proteus mirabilis C977 | 12.5 |
| Proteus morganii I580 | 6.2 |
| Proteus rettgeri WM16 | 6.2 |
| Proteus vulgaris WO91 | 6.2 |
| Pseudomonas aeruginosa A | 50 |
| Salmonella typhimurium CT10 | 1.6 |
| Serratia marcescens US20 | 6.2 |
| Shigella sonnei MB 11967 | 1.6 |
| Bacillus subtilis A | 1.6 |
| Staphylococcus aureus Oxford | 0.4 |
| Staphylococcus aureus Russell | 0.8 |
| Staphylococcus aureus 1517 | 50 |
| Streptococcus faecalis I | 25 |
| Streptococcus pneumoniae CN33 | 0.2 |
| Streptococcus pyogenes CN10 | 0.4 |
| E. coli ESS | 0.4 |

EXAMPLE 72 p-Nitrobenzyl (5R,6R)-3-[(E)-2-acetamidoethenylthio]-6-(1-allylthioethyl)-7-oxo-1-azabicyclo[3.2.0]hept-2-ene-2-carboxylate

EXAMPLE 73

Sodium (5R,6R)-3-[(E)-2-acetamidoethenylthio]-6-(1-allylthioethyl)-7-oxo-1-azabicyclo[3.2.0]hept-2-ene-2-carboxylate

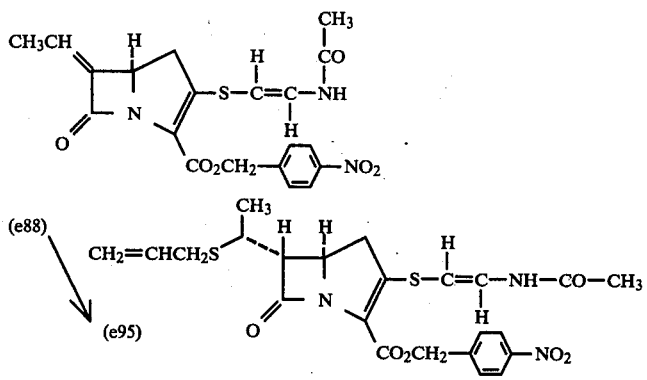

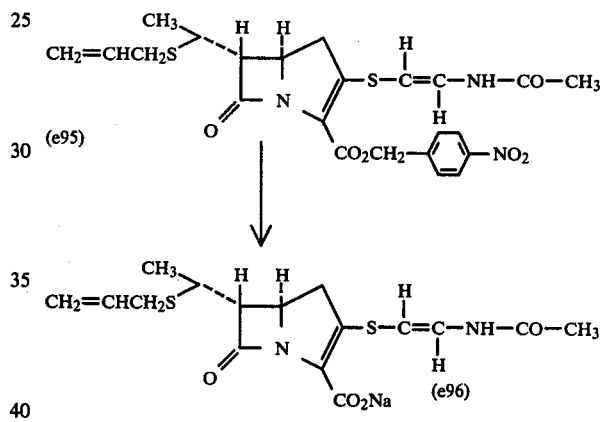

A solution of the ethylidene derivative (e88) (350 mg) in DMF (8 ml) was treated with anhydrous K$_2$CO$_3$ (56 mg) and allyl mercaptan (60 mg) at −20° with vigorous stirring for 20 min. Ethyl acetate (40 ml) was added and the solution was washed with water (4×50 ml) and brine (20 ml), before drying (MgSO$_4$) and evaporating in vacuo. The crude product was chromatographed on silica gel using petroleum ether-ethyl acetate mixtures (from 3:2 to 1:9) as eluant.

Early fractions contained mainly the least polar isomer of the title thioether (e95) which was obtained as a foam (43 mg); $\nu_{max}$. 3430, 1775, 1700 and 1620 cm$^{-1}$; $\lambda_{max}$(EtOH) 327 nm; δ(CDCl$_3$) 1.45 (3H, CH$_3$CH), 2.06 (3H,s,CH$_3$CO), 2.9–3.3 (6H,m,CH$_2$S, 4-CH$_2$, 6-CH and CH$_3$CHS), 4.10 (3H, br t, J 9 Hz), approx. 5.08 (2H, br d, allyl-CH$_2$=) 5.22 and 5.48 (each 1H, d, J 14, CO$_2$CH$_2$), approx. 5.6–6.0 (1H, m, allyl-CH), 5.87 (1H, d, J 13.5 Hz, =CH.S), 7.22 (1H, dd, J 13.5 and 10 Hz, =CHN), 7.63 and 8.19 (each 2H, d, J 9 Hz, C$_6$H$_4$) and 7.83 (1H, br d, J 10 Hz, NH).

The remaining fractions containing the product were combined and evaporated in vacuo to afford a gum (117 mg) which consisted of a mixture of the two diastereoisomers of (e95); i.r., u.v. and n.m.r. spectra as described for least polar isomer except for extra signals in the n.m.r. spectrum at δ(CDCl$_3$) 1.37 (d, J 7 Hz, CH$_3$CH) and 3.45 (m, 5-CH).

The diastereoisomeric ester (e95) (120 mg) was hydrogenolysed with 5% Pd on C (150 mg) in 20% aqueous dioxan (12 ml) in the manner described in Example 71. Work-up and chromatography on Biogel P2 afforded the title sodium salt (e96); $\lambda_{max}$. (H$_2$O) 309 and 227 nm.

The minimum inhibitory concentrations (MIC) of this compound was determined using a standard DST agar+10% horse blood substrate.

The results are shown below.

| ORGANISM | MIC (µg/ml) |
|---|---|
| *Citrobacter freundii* E8 | 50 |
| *Enterobactor cloacae* N1 | 25 |
| *Escherichia coli* 0111 | 50 |
| *Escherichia coli* JT 39 | 25 |
| *Klebsiella aerogenes* A | 6.2 |
| *Proteus mirabilis* C977 | 100 |
| *Proteus morganii* 1580 | 50 |
| *Proteus rettgeri* WM16 | 50 |
| *Proteus vulgaris* W091 | 25 |
| *Pseudomonas aeruginosa* A | >100 |
| *Salmonella typhimurium* CT10 | 25 |
| *Serratia marcescens* US20 | 50 |
| *Shigella sonnei* MB 11967 | 25 |
| *Bacillus subtilis* A | 1.6 |
| *Staphylococcus aureus* Oxford | 0.8 |
| *Staphylococcus aureus* Russell | 1.6 |
| *Staphylococcus aureus* 1517 | 12.5 |
| *Streptococcus faecalis* I | 50 |

-continued

| ORGANISM | MIC (μg/ml) |
|---|---|
| Streptococcus pneumoniae CN33 | ≤0.2 |
| Streptococcus pyogenes CN10 | 0.4 |
| E. coli ESS | 1.6 |

EXAMPLE 74 p-Nitrobenzyl
(5R,6R)-3-[(E)-2-acetamidoethenylthio]-6-[1-(2-acetamidoethylthio)ethyl]-7-oxo-1-azabicyclo[3.2.0-]hept-2-ene-2-carboxylate

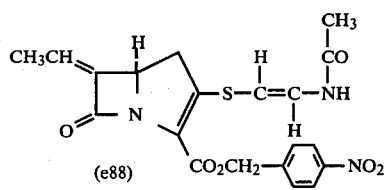

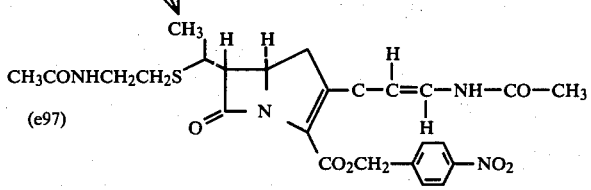

The ethylidene derivative (e88) (200 mg) was dissolved in DMF (4 ml) and the solution was cooled to −25°. Anhydrous $K_2CO_3$ (32 mg) was added with vigorous stirring, followed by 2-acetamidoethylthiol (55 mg). Stirring was continued at −20° for 20 min and the mixture was diluted with ethyl acetate (50 ml). The solution was washed with water (4×30 ml) and brine (20 ml), then dried ($MgSO_4$) and evaporated in vacuo. The residue was chromatographed on silica gel using a gradient elution from chloroform to 20% EtOH in $CHCl_3$, to afford the title thioether (e97) as a foam (106 mg). Trituration of the product with ether gave a pale-yellow solid which consisted of a diastereoisomeric mixture (approx. 1:1) of the thioether derivative (e97); λmax. (EtOH) 327 (14,600) and 263 nm (17,200); $\nu_{max}$. (KBr) 1775, 1695, 1650 and 1620 cm$^{-1}$; δ[$(CD_3)_2NCDO+D_2O$] approx. 1.39 (3H, m, C$\underline{H}_3$CH), 1.95 and 2.07 (each 3H, s, C$\underline{H}_3$CO), 2.6–3.85 (8H, m, 4-C$\underline{H}_2$, NC$\underline{H}_2$C$\underline{H}_2$S, 6-C$\underline{H}$ and $CH_3$C$\underline{H}$), approx. 4.2 (1H, m, 5-C$\underline{H}$), 5.32 and 5.57 (each 1H, d, J 14 Hz, $CO_2C\underline{H}_2$), 6.07 (1H, d, J 13.5 Hz, =C$\underline{H}$.S), 7.19 (1H, d, J 13.5 Hz, =C$\underline{H}$N), 7.81 and 8.26 (each d, J 9 Hz, $C_6\underline{H}_4$). [M+, 548.1395. $C_{24}H_{28}N_4O_7S_2$ requires 548.1396].

EXAMPLE 75

Sodium
(5R,6R)-3-[(E)-2-acetamidoethenylthio]-6-[1-(2-acetamidoethylthio)ethyl]-7-oxo-1-azabicyclo[3.2.0-]hept-2-ene-2-carboxylate

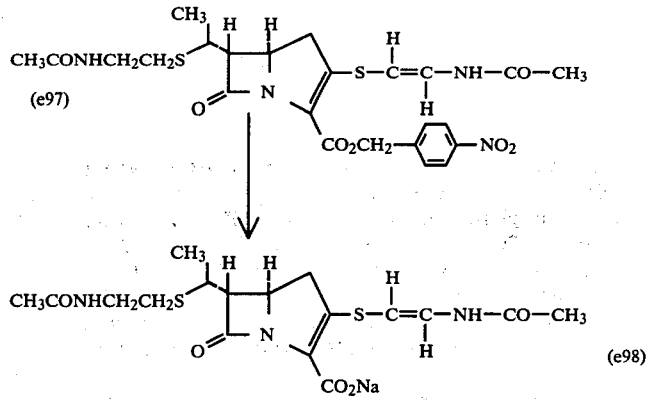

The ester (e97) (60 mg) was hydrogenolysed with 5% Pd on C (90 mg) in 20% aqueous dioxan (10 ml) as described in Example 71. Chromatography of the crude product on Biogel P2 afforded several fractions containing the desired sodium salt (e98) in aqueous solution; $\lambda_{max}$ ($H_2O$) 309 and 228 nm.

The minimum inhibitory concentrations (MIC) of this compound was determined using a standard DST agar +10% horse blood substrate.

The results are shown below.

| ORGANISM | MIC (μg/ml) |
|---|---|
| Citrobacter freundii E8 | 5.0 |
| Enterobactor cloacae N1 | 5.0 |

-continued

| ORGANISM | MIC (µg/ml) |
|---|---|
| *Escherichia coli* 0111 | 5.0 |
| *Escherichia coli* JT 39 | 5.0 |
| *Klebsiella aerogenes* A | 5.0 |
| *Proteus mirabilis* C977 | 12.5 |
| *Proteus morganii* 1580 | 25 |
| *Proteus rettgeri* WM16 | 12.5 |
| *Proteus vulgaris* WO91 | 12.5 |
| *Pseudomonas aeruginosa* A | >50 |
| *Salmonella typhimurium* CT10 | 2.5 |
| *Serratia marcescens* US20 | 12.5 |
| *Shigella sonnei* MB 11967 | 5.0 |
| *Bacillus subtilis* A | 2.5 |
| *Staphylococcus aureus* Oxford | 1.2 |
| *Staphylococcus aureus* Russell | 2.5 |
| *Staphylococcus aureus* 1517 | 12.5 |
| *Streptococcus faecalis* I | 50 |
| *Streptococcus pneumoniae* CN33 | 0.2 |
| *Streptococcus pyogenes* CN10 | 0.5 |
| *E. coli* ESS | 1.2 |

EXAMPLE 76 p-Nitrobenzyl
(5R,6R)-3-[(E)-2-acetamidoethenylthio]-6-[1-(2-p-nitrobenzyloxycarbonylaminoethylthio)ethyl]-7-oxo-1-azabicyclo[3.2.0]hept-2-ene-2-carboxylate

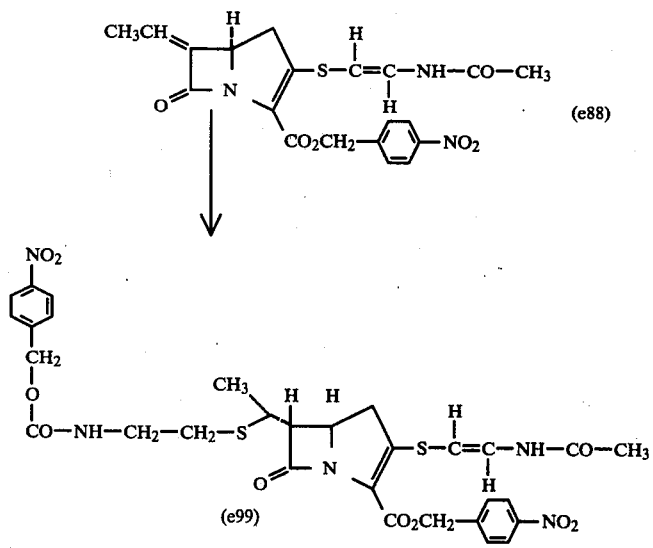

A solution of the ethylidene derivative (e88) (320 mg) in DMF (7 ml) was cooled to −20° and anhydrous $K_2CO_3$ (52 mg) was added. 2-p-nitrobenzyloxycarbonylaminoethylthiol (191 mg) was added with efficient stirring, and the mixture was stirred at −20° for 20 min. Ethyl acetate (40 ml) was added and the solution was washed with water (3×50 ml) and brine (20 ml), then dried ($MgSO_4$) and evaporated in vacuo. The residue was chromatographed on silica gel using a gradient elution of petroleum ether-ethyl acetate 2:3 to ethyl acetate. Fractions containing the product (identified by t.l.c.) were combined and evaporated in vacuo to afford the title compound (e99) as a foam (169 mg); $\lambda_{max}$ (EtOH) 326 and 265 nm; $\nu_{max}$ ($CHCl_3$) 1775, 1720 sh, 1700 and 1620 cm$^{-1}$; $\delta[(CD_3)_2CO]$ inter alia 1.42 (3H, d, J 6.5 Hz, C$\underline{H}_3$CH), 1.97 (3H, s, C$\underline{H}_3$CO), 2.65–2.9 (m, C$\underline{H}_2$S), approx. 3.05–3.5 (m, 4-C$\underline{H}_2$, C$\underline{H}_2$N, 6-C$\underline{H}$ and C$\underline{H}$CH$_3$), 4.15 (approx. dt, J approx. 3 and 9 Hz, 5-C$\underline{H}$), 5.02 (2H, s, C$\underline{H}_2$OCO), 5.27 and 5.53 (each 1H, d, J 14 Hz, C$\underline{H}_2$OCO), 5.95 (1H, d, J 14 Hz, =C$\underline{H}$S), approx. 6.6 (1H, br, CH$_2$N$\underline{H}$), 7.21 (1H, dd, J 11 and 14 Hz, =C$\underline{H}$N), 7.55–7.9 and 8.22 (8H, m, aromatic protons).

EXAMPLE 77 p-Nitrobenzyl
(5R,6R)-3-[(E)-2-acetamidoethenylthio]-6-[(R)-1-methylthioethyl]-7-oxo-1-azabicyclo[3.2.0]hept-2-ene-2-carboxylate and p-nitrobenzyl
(5R,6R)-3-[(E)-2-acetamidoethenylthio]-6-[(S)-1-methylthioethyl]-7-oxo-1-azabicyclo[3.2.0]hept-2-ene-2-carboxylate

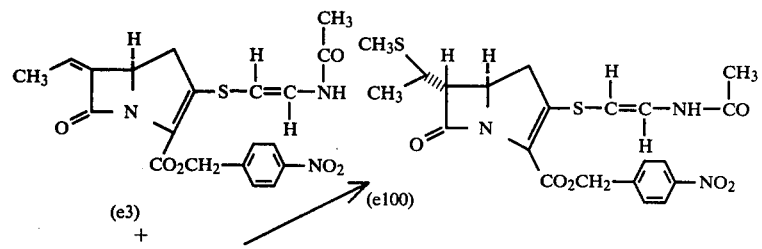

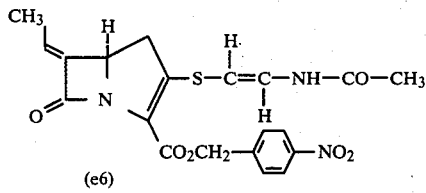

(e6)

A solution of the ethylidene derivatives (e3 and e6) (500 mg) in DMF (9 ml) was cooled to −20°. Anhydrous $K_2CO_3$ (80 mg) was added followed by solution of methyl mercaptan (53 mg) in DMF (0.6 ml) with vigorous stirring. Stirring was continued at −20° for 20 min. before adding ethyl acetate (50 ml). The solution was washed with dilute $NaHCO_3$ solution (30 ml), water (5×40 ml) and brine (20 ml) before drying ($MgSO_4$) and evaporating in vacuo. The residue was chromatographed on a column of silica gel using a gradient elution of petroleum ether/ethyl acetate mixtures (3:2 to 1:9).

Early fractions containing the product were combined and evaporated in vacuo to afford the least polar isomer of the title ester (e100) as a crystalline solid; $\lambda_{max}$. (EtOH) 327, 264 and 232 mm; $\delta$(DMF-d7) 1.40 (3H, d, J 6.5 Hz, C$\underline{H}_3$CH), 2.02 (3H, s, C$\underline{H}_3$CO), 2.13 (3H,s,C$\underline{H}_3$S), approx. 3.2 (1H,m,CH$_3$C$\underline{H}$), 3.28 (2H, d, J 9 Hz, 4-C$\underline{H}_2$), 3.58 (1H, dd, J 3 and 9 Hz, 6-C$\underline{H}$), 4.15 (1H, dt, J 3 and 9 Hz, 5-C$\underline{H}$), 5.33 and 5.58 (each 1H, d, J 14 Hz, $CO_2C\underline{H}_2$), 5.98 (1H, d, J 13.5 Hz, =C$\underline{H}$S), 7.21 (1H, dd, J 13.5 and 10 Hz, =C$\underline{H}$.N), 7.82 and 8.27 (each 2H, d, J 9 Hz, $C_6\underline{H}_4$) and 10.38 (1H, br d, J 10 Hz, N$\underline{H}$).

The main bulk of the fractions were combined and evaporated in vacuo to afford a white solid which was triturated with ethyl acetate/ether and filtered. The solid consisted of a mixture (approx. 1:1) of the 6-[(R)-methylthioethyl] and 6-[(S)-methylthioethyl] derivatives (e100) (199 mg); $\lambda_{max}$. (EtOH) 327, 264 and 232 nm; $\nu_{max}$.(KBr) 1778, 1700 br 1675 and 1625 cm$^{-1}$; $\delta$(DMF-d7) as described previously for the least polar isomer plus the following signals corresponding to the more polar isomer; 1.32 (3H, d, J 6 Hz, C$\underline{H}_3$CH), 2.17 (3H,s, C$\underline{H}_3$S) and 3.79 (1H, dd, J 3 and 6 Hz, 6-C$\underline{H}$).

The last few fractions contained the more polar isomer only. If desired, further quantities of each of the single isomers (e100) may be obtained by rechromatography of the isomeric mixture.

EXAMPLE 78

Sodium (5R,6R)-3-[(E)-2-acetamidoethenylthio]-6-(1-methylthioethyl)-7-oxo-1-azabicyclo[3.2.0]hept-2-ene-2-carboxylate

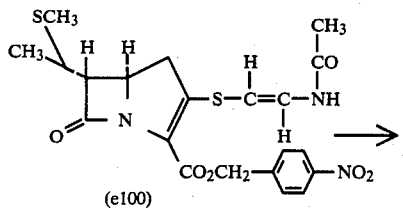

(e100)

(e101)

A. A mixture of 5% Pd on C (40 mg) and 30% aqueous dioxan (3 ml) was hydrogenated at room temperature and atmospheric pressure for 0.5 h. A solution of the least polar isomer of the methylthioderivative (e100) (25 mg) in 30% aqueous dioxan (2 ml) was added to the hydrogenation vessel, and hydrogenation was continued for a further 4 h. A solution of $NaHCO_3$ (5 mg) in water (2 ml) was added to the mixture which was filtered through Celite, washing with water. The solution was concentrated in vacuo to approximately 10 ml, and then washed with ethyl acetate (3×25 ml), before concentrating to approximately 3 ml. The aqueous solution was chromatographed on a column of Biogel P2 (2.5×15 cm), and fractions were monitored by u.v. Those which showed chromophores at both $\lambda_{max}$. 309 and 228 nm contained a single isomer of the title sodium salt (e101) (5 mg).

B. An isomeric mixture (approx. 1:1) of the thioether derivatives (e100) (85 mg) was hydrogenated with 5% Pd on C catalyst (130 mg) in 30% aqueous dioxan (10 ml) exactly as described in section A, using 16 mg of $NaHCO_3$ during work-up. After Biogel P2 chromatography, fractions containing the product were combined and concentrated in vacuo using ethanol to azeotrope out water, and toluene to similarly remove ethanol. The title salt (e101), a mixture of two diastereoisomers, was obtained as an off-white solid (30 mg); $\lambda_{max}$. ($H_2O$) 309 and 228 nm; $\nu_{max}$. (KBr) 1755, 1675 and 1620 cm$^{-1}$.

The minimum inhibitory concentrations (MIC) of this compound was determined using a standard DST agar+10% horse blood substrate. The tests used an undiluted inoculum of bacteria. The results are shown below.

| ORGANISM | MIC (μg/ml) |
| --- | --- |
| *Citrobacter freundii* E8 | 5.0 |
| *Enterobactor cloacae* N1 | 2.5 |
| *Escherichia coli* 0111 | 2.5 |
| *Escherichia coli* JT 39 | 2.5 |
| *Klebsiella aerogenes* A | 2.5 |
| *Proteus mirabilis* C977 | 12.5 |
| *Proteus morganii* 1580 | 12.5 |
| *Proteus rettgeri* WM16 | 5.0 |
| *Proteus vulgaris* WO91 | 5.0 |
| *Pseudomonas aeruginosa* A | 50 |
| *Salmonella typhimurium* CT10 | 1.2 |
| *Serratia marcescens* US20 | 5.0 |
| *Shigella sonnei* MB 11967 | 1.2 |
| *Bacillus subtilis* A | 1.2 |

| ORGANISM | MIC (μg/ml) |
|---|---|
| *Staphylococcus aureus* Oxford | 0.5 |
| *Staphylococcus aureus* Russell | 0.5 |
| *Staphylococcus aureus* 1517 | 12.5 |
| *Streptococcus faecalis* I | 12.5 |
| *Streptococcus pneumoniae* CN33 | 0.1 |
| *Streptococcus pyogenes* CN10 | 0.2 |
| *E. Coli* ESS | 1.2 |

EXAMPLE 79 p-Nitrobenzyl (5R,6R)-3-[(E)-2-acetamidoethenylthio]-6-[(R)-1-phenylthioethyl]-7-oxo-1-azabicyclo[3.2.0]hept-2-ene-2-carboxylate

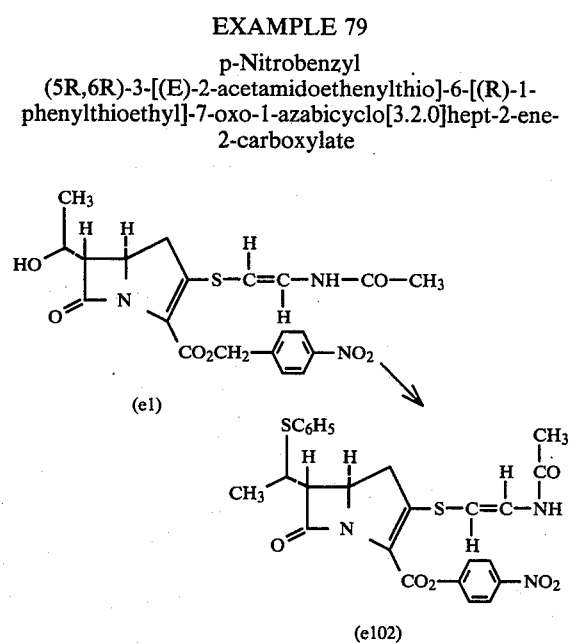

p-Nitrobenzyl (5R,6S)-3-[(E)-2-acetamidoethenylthio]-6-[(S)-1-hydroxyethyl]-7-oxo-1-azabicyclo[3.2.0]hept-2-ene-2-carboxylate (e1) (100 mg) in tetrahydrofuran (THF) (5 ml) was treated with N-phenylthiosuccinimide (43 mg) in THF (1 ml) followed by tri-n-butylphosphine (45 mg). After 1 hr. the solution was added to a solution of tri-n-butylphosphine (45 mg) in THF (4 ml) which had been treated with N-phenylthiosuccinimide (45 mg) in THF (1 ml) for 5 min. After a further 1 hr. the reaction mixture was added to tri-n-butylphosphine (150 mg) in THF (4 ml) which had been treated with N-phenylthiosuccinimide (145 mg) in THF (1 ml) and stirring was continued for 3 hr. T.l.c. on silica gel using ethyl acetate elution indicated the formation of a KMnO₄ positive zone with $R_f$ slightly less than the sulphenimide/phosphine complex. The THF was evaporated in vacuo, and ethyl acetate (100 ml) and water (100 ml) were added. The ethyl acetate layer was then washed with approx. 5% aqueous NaHCO₃ (20 ml), then with water, then dried (MgSO₄) and evaporated in vacuo. The residue was chromatographed on silica gel (230-400 mesh ASTM) (approx. 20 g) eluting with ethyl acetate/cyclohexane mixtures; 1:1 (50 ml); followed by 3:1. This gave the product, containing a contaminant (28 mg). The mixture was rechromatographed on silica gel, eluting with ethyl acetate/cyclohexane mixtures; 1:1 (50 ml), followed by 6:4, to give p-nitrobenzyl (5R,6R)-3-[(E)-2-acetamidoethenylthio]-6-[(R)-1-phenylthioethyl]-7-oxo-1-azabicyclo[3.2.0]hept-2-ene-2-carboxylate (e102) (22 mg) as a single isomer. $\lambda_{max}$ (EtOH) 327, 263 nm; $\nu_{max}$ (CHCl₃) 1780, 1710, 1625 cm⁻¹; δ(CDCl₃+D₂O) 1.46 (3H, d, J 6 Hz), 2.07 (3H, s), 2.7-3.7 (4H, m), 3.8-4.2 (1H,m), 5.19 and 5.46 (2H, ABq, J 14 Hz), 5.84 (1H, d, J 14 Hz), 7.0-7.2 (8H,m), 8.20 (2H, d, J 9 Hz).

EXAMPLE 80 p-Nitrobenzyl (5R,6S)-3-(2-acetamidoethylthio)-6-[(R)-1-phenylthioethyl]-7-oxo-1-azabicyclo[3.2.0]hept-2-ene-2-carboxylate

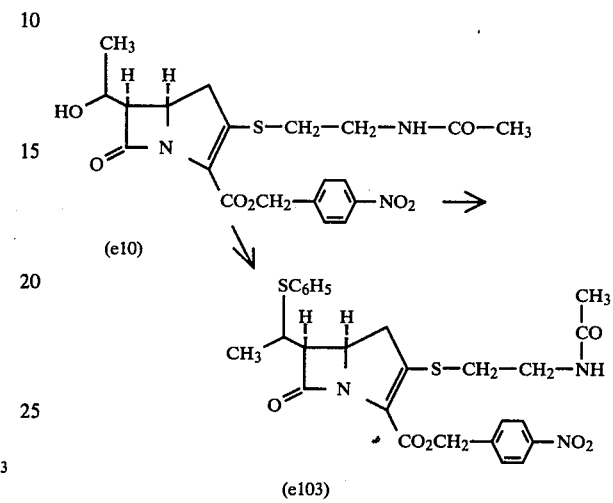

p-Nitrobenzyl (5R,6R)-3-(2-acetamidoethylthio)-6-[(S)-1-hydroxyethyl]-7-oxo-1-azabicyclo[3.2.0]hept-2-ene-2-carboxylate (e10) (100 mg) in suspension in tetrahydrofuran (THF) (5 ml) was added to tri-n-butylphosphine (240 mg) in THF (5 ml) which had been pretreated with N-phenylthiosuccinimide (240 mg) in THF (2 ml) for 5 min. After stirring at room temperature for 2.5 hr., the THF was evaporated in vacuo, ethyl acetate (50 ml) was added and the solution washed with water (2×50 ml), saturated aqueous NaHCO₃ (2×50 ml), water (2×25 ml) and then with brine (25 ml). After drying (MgSO₄), the ethyl acetate was evaporated in vacuo and the residue chromatographed on silica gel (12 g) eluting with ethyl acetate/cyclohexane mixtures; 1:1 (50 ml), 6:4 (50 ml), 7:3 (50 ml), 8:2 (50 ml) and finally with ethyl acetate; this gave the thioether contaminated by by-products of the reaction, so it was rechromatographed on silica gel to give p-nitrobenzyl (5R, 6S)-3-(2-acetamidoethylthio)-6-[(R)-1-phenylthioethyl]-7-oxo-1-azabicyclo[3.2.0]hept-2-ene-2-carboxylate (e 103) (11 mg). $\lambda_{max}$ (EtOH) 318, 264 nm; $\nu_{max}$ (CHCl₃) 1780, 1700, 1665 cm⁻¹.

EXAMPLE 81

Sodium (5R,6S)-3-(2-acetamidoethylthio)-6-[(R)-1-phenylthioethyl]-7-oxo-1-azabicyclo[3.2.0]hept-2-ene-2-carboxylate

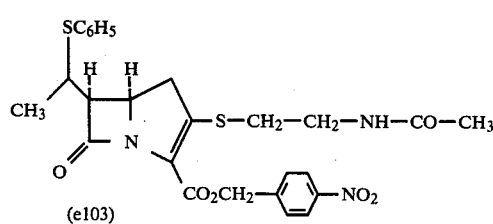

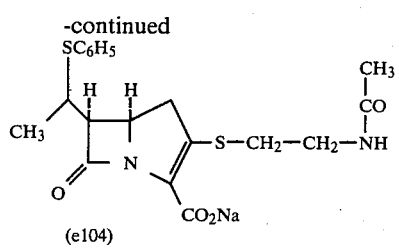

(e104)

p-Nitrobenzyl (5R,6S)-3-(2-acetamidoethylthio)-6-[(R)-1-phenylthioethyl]-7-oxo-1-azabicyclo[3.2.0]-hept-2-ene-2-carboxylate (e 103) (10 mg) in a mixture of dioxan and water (7:3, 5 ml) was added to 5% palladium on carbon catalyst which had been prehydrogenated for 30 min. in a mixture of dioxan and water (7:3, 5 ml). The mixture was hydrogenated at slightly super-atmospheric pressure for 4 hr., when sodium hydrogen carbonate (1.9 mg) was added to the mixture. The catalyst was filtered off and washed with water (5 ml). The filtrate was evaporated in vacuo to remove most of the dioxan and the resultant mixture was diluted with water to 25 ml and extracted with ethyl acetate. The aqueous extract was washed with ethyl acetate. The u.v. spectrum of the aqueous layer showed a maximum of about 300 nm, indicating the presence of the sodium salt. The volume of the aqueous solution was reduced to about 1 ml, loaded onto a Biogel P-2 column and eluted with water to give sodium (5R,6S)-3-(2-acetamidoethylthio)-6-[(R)-1-phenylthioethyl]-7-oxo-1-azabicyclo[3.2.0-]hept-2-ene-2-carboxylate (e 104).

EXAMPLE 82

Sodium (5R,6R)-3-[(E)-2-acetamidoethenylthio]-6-ethyl-7-oxo-1-azabicyclo[3.2.0]hept-2-ene-2-carboxylate

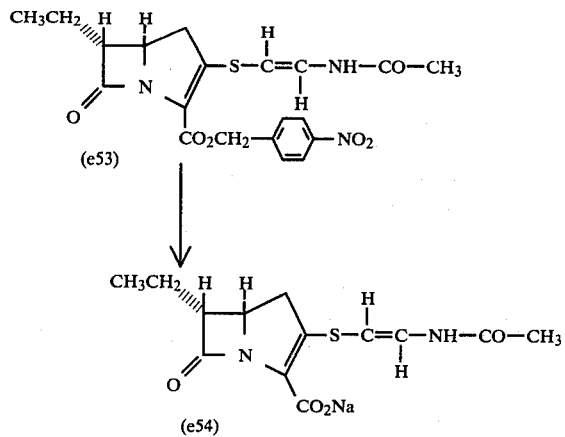

A solution of the ester (e53) (235 mg) in dioxan (5 ml) was added to a mixture of 5% Pd-C in 30% aqueous dioxan (20 ml) which had been prehydrogenated for 0.5 h. Hydrogenation was continued at ambient pressure and temperature for a further 4 h. A solution of NaHCO₃ (46 mg) in water (5 ml) was added to the mixture, which was then filtered through Celite, washing with water (10 ml). The solution was concentrated in vacuo to a volume of about 25 ml and was then washed with ethyl acetate (3×50 ml) before concentrating further to about 5 ml. The aqueous solution was introduced onto a column of Biogel P2 (20×3.5 cm) which was then eluted with water. Fractions were monitored by uv and those containing the product were combined and evaporated in vacuo. Ethanol (20 ml) was added and the solution was again evaporated in vacuo and the process repeated to remove the last traces of water. Toluene (2×20 ml) was added and evaporation in vacuo continued until the sodium salt (e 54) was obtained as a buff-coloured solid (62 mg); $\lambda_{max.}$ (H$_2$O) 307 and 228 nm. $\nu_{max.}$ (KBr) 1755, 1675 and 1620 cm$^{-1}$.

We claim:

1. A compound of the formula (I):

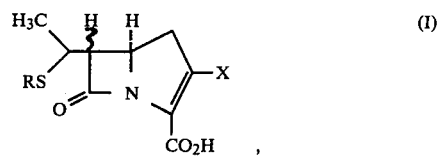

a pharmaceutically acceptable salt thereof, or an ester which is convertible by chemical or biological means to the corresponding acid or salt thereof wherein X is SCH$_2$CH$_2$NH$_2$ or YNH.CO.CH$_3$ wherein Y is SCH$_2$CH$_2$, trans SO—CH=CH or cis or trans S—CH=CH and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, alkanoyloxy, lower alkyl esterified carboxyl, carboxyl, amino or lower alkylamide, or R is 2-benzyloxycarbonylaminoethyl, 2-p-nitrobenzyloxycarbonylaminoethyl, 2-p-methoxybenzyloxycarbonylaminoethyl, benzyloxycarbonylmethyl or p-nitrobenzyloxycarbonylmethyl.

2. The compound of the formula (II):

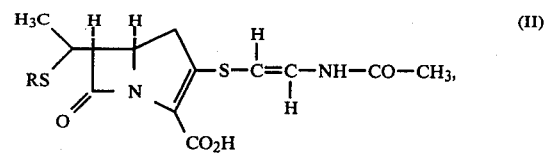

a pharmaceutically acceptable salt thereof, or an ester which is convertible by chemical or biological means to the corresponding acid or salt thereof wherein R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

3. The compound of the formula (III):

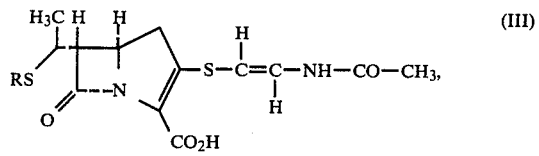

a pharmaceutically acceptable salt thereof, or an ester which is convertible by chemical or biological means to the corresponding acid or salt thereof wherein R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

4. The compound of the formula (IV):

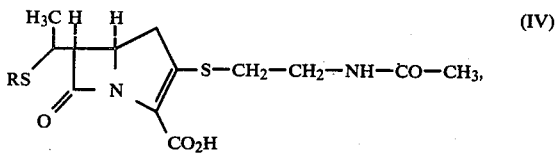
(IV)

a pharmaceutically acceptable salt thereof, or an ester which is convertible by chemical or biological means to the corresponding acid or salt thereof wherein R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

5. The compound of the formula (V):

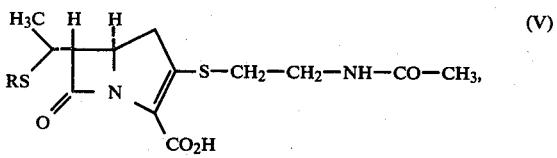
(V)

a pharmaceutically acceptable salt thereof, or an ester which is convertible by chemical or biological means to the corresponding acid or salt thereof wherein R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

6. The compound of the formula (VI):

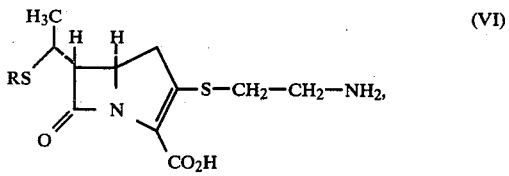
(VI)

a pharmaceutically acceptable salt thereof, or an ester which is convertible by chemical or biological means to the corresponding acid or salt thereof wherein R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

7. A compound according to claim 1 which has the 8S configuration.

8. A compound according to claim 1 which has the 8R configuration.

9. A compound according to claim 1 which is a mixture of 8R and 8S forms.

10. A compound according to claim 1 wherein R is methyl, ethyl, n-propyl, n-butyl, benzyl, 2-phenylethyl, phenyl, p-methylphenyl, p-methoxyphenyl, p-chlorophenyl, methoxycarbonylmethyl or ethoxycarbonylmethyl.

11. A compound according to claim 1 wherein R is 2-aminoethyl, 2-benzoyloxycarbonylaminoethyl, 2-p-nitrobenzyloxycarbonylaminoethyl, 2-p-methoxybenzoyloxycarbonylaminoethyl, allyl, p-nitrobenzyl, p-chlorobenzyl, p-bromobenzyl, p-methoxybenzyl, p-methylbenzyl, 2-acetamidoethyl, benzyloxycarbonylmethyl, p-nitrobenzyloxycarbonylmethyl, 2-methoxyethyl or 2-acetoxyethyl.

12. A compound according to claim 1 wherein R is methyl, ethyl, benzyl or phenyl.

13. A compound according to claim 1 in the form of the free acid or a pharmaceutically acceptable salt.

14. A compound according to claim 1 in the form of an ester.

15. A compound according to claim 14 which is a p-nitrobenzyl ester.

16. A compound according to claim 2 which has the 8S configuration.

17. A compound according to claim 3 which has the 8S configuration.

18. A compound according to claim 4 which has the 8S configuration.

19. A compound according to claim 5 which has the 8S configuration.

20. A compound according to claim 6 which has the 8S configuration.

21. A compound according to claim 2 which has the 8R configuration.

22. A compound according to claim 3 which has the 8R configuration.

23. A compound according to claim 4 which has the 8R configuration.

24. A compound according to claim 5 which has the 8R configuration.

25. A compound according to claim 6 which has the 8R configuration.

26. A compound according to claim 2 which is a mixture of 8R and 8S forms.

27. A compound according to claim 3 which is a mixture of 8R and 8S forms.

28. A compound according to claim 4 which is a mixture of 8R and 8S forms.

29. A compound according to claim 5 which is a mixture of 8R and 8S forms.

30. A compound according to claim 6 which is a mixture of 8R and 8S forms.

31. A pharmaceutical composition useful for treating bacterial infections in humans and animals which comprises an antibacterially effective amount of a compound of the formula (I):

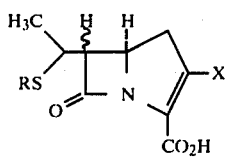

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido, in combination with a pharmaceutically acceptable carrier, or R is 2-benzyloxycarbonylaminoethyl, 2-p-nitrobenzyloxycarbonylaminoethyl, 2-p-methoxybenzyloxycarbonylamino, benzyloxycarbonylmethyl or p-nitrobenzyloxycarbonylmethyl.

32. A composition according to claim 31 wherein the compound is of the formula (II):

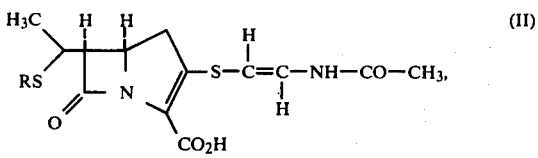

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{—}CH=CH$ or cis or trans $S\text{—}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido, in combination with a pharmaceutically acceptable carrier.

33. A composition according to claim 31 wherein the compound is of the formula (III):

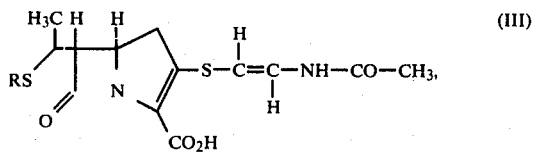

a pharmaceutically acceptable salt thereof or an in vivo hydrozylable ester thereof, wherein X is $SCH_2C_2NH_2$ or $YNH.CO.CH_3$ wherein Y is $SCH_2CH_2$, trans $SO\text{—}CH=CH$ or cis or trans $S\text{-}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido, in combination with a pharmaceutically acceptable carrier.

34. A composition according to claim 31 wherein the compound is of the formula (IV):

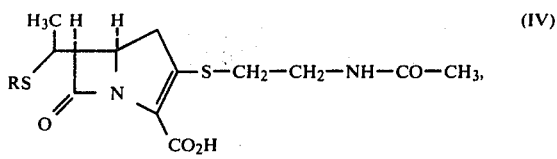

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido, in combination with a pharmaceutically acceptable carrier.

35. A composition according to claim 31 wherein the compound is of the formula (V):

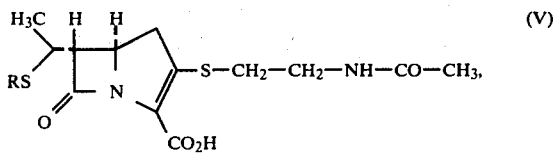

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido, in combination with a pharmaceutically acceptable carrier.

36. A compound according to claim 31 wherein the compound is of the formula (VI):

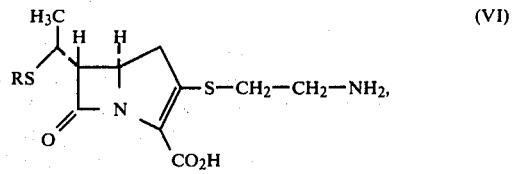

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}$ CH≡CH and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido, in combination with a pharmaceutically acceptable carrier.

37. A composition according to claim 31 wherein the compound has the 8S configuration.

38. A composition according to claim 31 wherein the compound has the 8R configuration.

39. A composition according to claim 31 wherein the compound is a mixture of 8R and 8S isomers.

40. A composition according to claim 31 wherein R is a methyl, ethyl, n-propyl, n-butyl, benzyl, 2-phenylethyl, phenyl, p-methylphenyl, p-methoxyphenyl, p-chlorophenyl, methoxycarbonylmethyl or ethoxycarbonylmethyl.

41. A composition according to claim 31 wherein R is 2-aminoethyl, 2-benzyloxycarbonylaminoethyl, 2-p-nitrobenzyloxycarbonylaminoethyl, 2-p-methoxybenzyloxycarbonylaminoethyl, allyl, p-nitrobenzyl, p-chlorobenzyl, p-bromobenzyl, p-methoxybenzyl, p-methylbenzyl, 2-acetaminoethyl, benzyloxycarbonylmethyl, p-nitrobenzyloxycarbonylmethyl, 2-methoxyethyl or 2-acetoxyethyl.

42. A composition according to claim 31 wherein R is methyl, ethyl, benzyl or phenyl.

43. A composition according to claim 31 wherein the compound is in the form of a free acid or pharmaceutically acceptable salt.

44. A composition according to claim 31 wherein the compound is in the form of an in vivo hydrolyzable ester.

45. A composition according to claim 44 wherein the ester is a p-nitrobenzyl ester.

46. A composition according to claim 32 wherein the compound has the 8S configuration.

47. A composition according to claim 33 wherein the compound has the 8S configuration.

48. A composition according to claim 34 wherein the compound has the 8s configuration.

49. A composition according to claim 35 wherein the compound has the 8S configuration.

50. A composition according to claim 36 wherein the compound has the 8S configuration.

51. A composition according to claim 32 wherein the compound has the 8R configuration.

52. A composition according to claim 33 wherein the compound has the 8R configuration.

53. A composition according to claim 34 wherein the compound has the 8R configuration.

54. A composition according to claim 35 wherein the compound has the 8R configuration.

55. A composition according to claim 36 wherein the compound has the 8R configuration.

56. A composition according to claim 32 wherein the compound is a mixture of 8R and 8S forms.

57. A composition according to claim 33 wherein the compound is a mixture of 8R and 8S forms.

58. A composition according to claim 34 wherein the compound is a mixture of 8R and 8S forms.

59. A composition according to claim 35 wherein the compound is a mixture of 8R and 8S forms.

60. A composition according to claim 36 wherein the compound is a mixture of 8R and 8S forms.

61. A method of treating bacterial infections in humans and animals which comprises administering to a human or animal in need thereof an antibacterially effective amount of a compound of the formula (I):

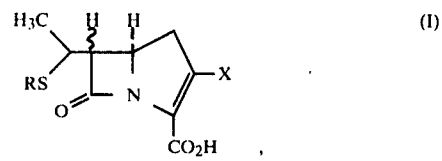

a pharmaceutically acceptable salt thereof or an in vivo hydroxylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido or R is 2-benzyloxycarbonylaminoethyl, 2-p-nitrobenzyloxycarbonylaminoethyl, 2-p-methoxybenzyloxycarbonylaminoethyl, benzyloxycarbonylmethyl or p-nitrobenzyloxycarbonylmethyl.

62. A method according to claim 61 wherein the compound is of the formula (II):

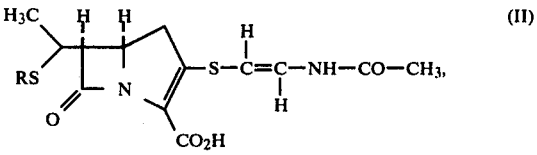

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}CH=CH$ and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

63. A method according to claim 61 wherein the compound is of the formula (III):

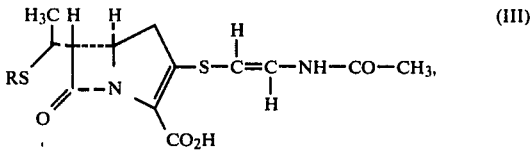

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans $SO\text{-}CH=CH$ or cis or trans $S\text{-}$ CH=CH and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

64. A method according to claim 61 wherein the compound is of the formula (IV):

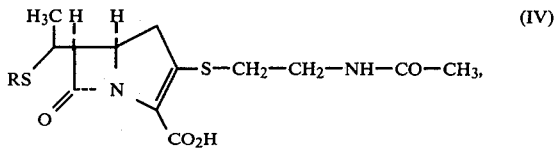

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans SO-CH=CH or cis or trans S-CH=CH and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

65. A method according to claim 61 wherein the compound is of the formula (V):

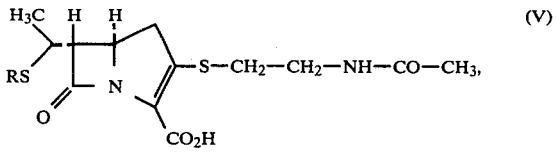

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans SO-CH=CH or cis or trans S-CH=CH and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

66. A method according to claim 61 wherein the compound is of the formula (VI):

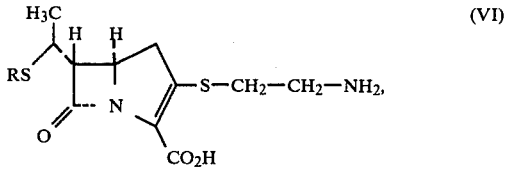

a pharmaceutically acceptable salt thereof or an in vivo hydrozylable ester thereof, wherein X is $SCH_2CH_2NH_2$ or $YNH.CO.CH_3$ wherein Y is $SCH_2CH_2$, trans SO-CH=CH or cis or trans S-

CH=CH and R is lower alkyl, phenyl unsubstituted or substituted by nitro, fluoro, chloro, bromo, lower alkyl or lower alkyloxy, lower alkyl substituted by phenyl which phenyl moiety is itself unsubstituted or substituted by nitro, fluoro, chloro, bromo, lower alkyl or lower alkyloxy, lower alkenyl or lower alkyl substituted by lower alkoxy, lower alkanoyloxy, lower alkyl esterified carboxyl, carboxyl, amino or lower alkylamido.

67. A method according to claim 61 wherein the compound has the 8S configuration.

68. A method according to claim 61 wherein the compound has the 8R configuration.

69. A method according to claim 61 wherein the compound is a mixture of 8R and 8S isomers.

70. A method according to claim 61 wherein R is a methyl, ethyl, n-propyl, n-butyl, benzyl, 2-phenylethyl, phenyl, p-methylphenyl, p-methoxyphenyl, p-chlorophenyl, methoxycarbonylmethyl or ethoxycarbonylmethyl.

71. A method according to claim 61 wherein R is 2-aminoethyl, 2-benzyloxycarbonylaminoethyl, 2-p-nitrobenzyloxycarbonylaminoethyl, 2-p-methoxybenzyloxycarbonylaminoethyl, allyl, p-nitrobenzyl, p-chlorobenzyl, p-bromobenzyl, p-methoxybenzyl, p-methylbenzyl, 2-acetaminoethyl, benzyloxycarbonylmethyl, p-nitrobenzyloxycarbonylmethyl, 2-methoxyethyl or 2-acetoxyethyl.

72. A method according to claim 61 wherein R is methyl, ethyl, benzyl or phenyl.

73. A method according to claim 61 wherein the compound is in the form of a free acid or pharmaceutically acceptable salt.

74. A method according to claim 61 wherein the compound is in the form of an in vivo hydrolyzable ester.

75. A method according to claim 74 wherein the ester is a p-nitrobenzyl ester.

76. A method according to claim 62 wherein the compound has the 8S configuration.

77. A method according to claim 63 wherein the compound has the 8S configuration.

78. A method according to claim 64 wherein the compound has the 8S configuration.

79. A method according to claim 65 wherein the compound has the 8S configuration.

80. A method according to claim 66 wherein the compound has the 8S configuration.

81. A method according to claim 62 wherein the compound has the 8R configuration.

82. A method according to claim 63 wherein the compound has the 8R configuration.

83. A method according to claim 64 wherein the compound has the 8R configuration.

84. A method according to claim 65 wherein the compound has the 8R configuration.

85. A method according to claim 66 wherein the compound has the 8R configuration.

86. A method according to claim 62 wherein the compound is a mixture of 8R and 8S forms.

87. A method according to claim 63 wherein the compound is a mixture of 8R and 8S forms.

88. A method according to claim 64 wherein the compound is a mixture of 8R and 8S forms.

89. A method according to claim 65 wherein the compound is a mixture of 8R and 8S forms.

90. A method according to claim 66 wherein the compound is a mixture of 8R and 8S forms.

* * * * *